United States Patent
Ketterer et al.

(10) Patent No.: US 10,780,054 B2
(45) Date of Patent: Sep. 22, 2020

(54) LYOPHILIZATION OF RNA

(71) Applicant: CureVac Real Estate GmbH, Tübingen (DE)

(72) Inventors: Thomas Ketterer, Gomaringen (DE); Thorsten Mutzke, Reutlingen (DE); Michael Wiggenhorn, Munich (DE); Frank Schaubhut, Germering (DE); Florian Von Der Mülbe, Stuttgart (DE)

(73) Assignee: CureVac Real Estate GmbH, Tübingen (DE)

( * ) Notice: Subject to any disclaimer, the term of this patent is extended or adjusted under 35 U.S.C. 154(b) by 0 days.

(21) Appl. No.: 15/566,980

(22) PCT Filed: Apr. 15, 2016

(86) PCT No.: PCT/EP2016/000622
§ 371 (c)(1),
(2) Date: Oct. 16, 2017

(87) PCT Pub. No.: WO2016/165831
PCT Pub. Date: Oct. 20, 2016

(65) Prior Publication Data
US 2018/0243219 A1 Aug. 30, 2018

(30) Foreign Application Priority Data
Apr. 17, 2015 (WO) .................. PCT/EP2015/000818

(51) Int. Cl.
| | | |
|---|---|---|
| C07H 21/04 | (2006.01) |
| A61K 9/19 | (2006.01) |
| A61K 31/7105 | (2006.01) |
| C12Q 1/6806 | (2018.01) |
| A61K 47/64 | (2017.01) |
| A61K 47/54 | (2017.01) |
| C12N 15/10 | (2006.01) |

(52) U.S. Cl.
CPC ............ *A61K 9/19* (2013.01); *A61K 31/7105* (2013.01); *A61K 47/549* (2017.08); *A61K 47/64* (2017.08); *C12Q 1/6806* (2013.01); *C12N 15/1003* (2013.01)

(58) Field of Classification Search
None
See application file for complete search history.

(56) References Cited

U.S. PATENT DOCUMENTS

| | | |
|---|---|---|
| 2005/0032730 A1 | 2/2005 | Von der Mulbe et al. |
| 2005/0059624 A1 | 3/2005 | Hoerr et al. |
| 2005/0250723 A1 | 11/2005 | Hoerr et al. |
| 2006/0188490 A1 | 8/2006 | Hoerr et al. |
| 2008/0025944 A1 | 1/2008 | Hoerr et al. |
| 2008/0267873 A1 | 10/2008 | Hoerr et al. |
| 2009/0324584 A1 | 12/2009 | Hoerr et al. |
| 2010/0048883 A1 | 2/2010 | Ketterer et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0053829 A1 | 3/2011 | Baumhof et al. |
| 2011/0182941 A1 | 7/2011 | Depaz et al. |
| 2011/0250225 A1 | 10/2011 | Fotin-Mleczek et al. |
| 2012/0021043 A1 | 1/2012 | Kramps et al. |
| 2012/0258046 A1 | 10/2012 | Mutzke |
| 2013/0129754 A1 | 5/2013 | Thess et al. |
| 2013/0142818 A1 | 6/2013 | Baumhof et al. |
| 2013/0259879 A1 | 10/2013 | Baumhof et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0165006 A1 | 6/2015 | Thess et al. |

(Continued)

FOREIGN PATENT DOCUMENTS

| | | |
|---|---|---|
| WO | WO 2011-069586 | 6/2011 |
| WO | WO 2012/170889 | 12/2012 |

(Continued)

OTHER PUBLICATIONS

Fonte et al. (Journal of Controlled Release 225 (2016) 75-86) 2016.*
International Preliminary Report on Patentability issued in corresponding PCT Application No. PCT/EP2016/000622, dated Oct. 17, 2017.
International Search Report and Written Opinion issued in corresponding PCT Application No. PCT/EP2016/000622, dated Jun. 15, 2016.
Jones et al., "Long-term storage of DNA-free RNA for use in vaccine studies," *Biotechniques*, 43(5):675-681, 2007.
Kasper et al., "Formulation development of lyophilized, long-term stable siRNA/oligoaminoamide polyplexes," *Eur. J. Pharm. Biopharm.*, 85(2):294-305, 2013.

(Continued)

*Primary Examiner* — Kimberly Chong
(74) *Attorney, Agent, or Firm* — Parker Highlander PLLC

(57) ABSTRACT

The present invention is directed to the field of RNA formulation, in particular to lyophilization of RNA. The invention provides a method for lyophilization of RNA. The present invention further concerns a lyophilized composition obtainable by the inventive method, a pharmaceutical composition, a vaccine and a kit or kit of parts. Moreover, the present invention provides a novel use of a lyoprotectant for lyophilizing RNA, the use of the inventive method in the manufacture of a medicament as well as the first and second medical use of the composition obtainable by the inventive method, the pharmaceutical composition, the vaccine or the kit or kit of parts according to the invention.

17 Claims, 11 Drawing Sheets

Specification includes a Sequence Listing.

(56) References Cited

U.S. PATENT DOCUMENTS

| | | |
|---|---|---|
| 2015/0184195 A1 | 7/2015 | Thess et al. |
| 2015/0218554 A1 | 8/2015 | Thess |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | Von Der Mulbe et al. |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |

FOREIGN PATENT DOCUMENTS

| | | |
|---|---|---|
| WO | WO 2016-107877 | 7/2016 |
| WO | WO 2016-165825 | 10/2016 |
| WO | WO 2016-174227 | 11/2016 |
| WO | WO 2016-174271 | 11/2016 |
| WO | WO 2016-184575 | 11/2016 |
| WO | WO 2016-184576 | 11/2016 |
| WO | WO 2016-184822 | 11/2016 |
| WO | WO 2016-193206 | 12/2016 |
| WO | WO 2016-193226 | 12/2016 |
| WO | WO 2016-203025 | 12/2016 |
| WO | WO 2017-001058 | 1/2017 |
| WO | WO 2017-009376 | 1/2017 |
| WO | WO 2017-021546 | 2/2017 |
| WO | WO 2017-025120 | 2/2017 |
| WO | WO 2017-025447 | 2/2017 |
| WO | WO 2017-036580 | 3/2017 |

OTHER PUBLICATIONS

Meister et al., "Freeze-Dry Microscopy: Impact of Nucleation Temperature and Excipient Concentration on Collapse Temperature Data", 10(2):582-588, 2009.

Operating Manual Freeze Dryer ALPHA 1-4 LSC/ALPHA 2-4 LSC, Version 04.2003, 2003.

Yadava et al, "Effect of Lyophilization and Freeze-thawing on the Stability of siRNA-liposome Complexes", *AAPS PharmSciTech.*, 9(2):335-341, 2008.

\* cited by examiner

PpLuc(GC)-muag-A64-C30 (SEQ ID NO: 1)

GGGAGAAAGCUUGAGGAUGGAGGACGCCAAGAACAUCAAGAAGGGCCCGGCGCCCUUCUACCCGCUGG
AGGACGGGACCGCCGGCGAGCAGCUCCACAAGGCCAUGAAGCGGUACGCCCUGGUGCCGGGCACGAUC
GCCUUCACCGACGCCCACAUCGAGGUCGACAUCACCUACGCGGAGUACUUCGAGAUGAGCGUGCGCCU
GGCCGAGGCCAUGAAGCGGUACGGCCUGAACACCAACCACCGGAUCGUGGUGUGCUCGGAGAACAGCC
UGCAGUUCUUCAUGCCGGUGCUGGGCGCCCUCUUCAUCGGCGUGGCCGUCGCCCCGGCGAACGACAUC
UACAACGAGCGGGAGCUGCUGAACAGCAUGGGGAUCAGCCAGCCGACCGUGGUGUUCGUGAGCAAGAA
GGGCCUGCAGAAGAUCCUGAACGUGCAGAAGAAGCUGCCCAUCAUCCAGAAGAUCAUCAUCAUGGACA
GCAAGACCGACUACCAGGGCUUCCAGUCGAUGUACACGUUCGUGACCAGCCACCUCCGCCGGGCUUC
AACGAGUACGACUUCGUCCCGGAGAGCUUCGACCGGGACAAGACCAUCGCCCUGAUCAUGAACAGCAG
CGGCAGCACCGGCCUGCCGAAGGGGGUGGCCCUGCCGCACCGGACCGCCUGCGUGCGCUUCUCGCACG
CCCGGGACCCCAUCUUCGGCAACCAGAUCAUCCCGGACACCGCCAUCCUGAGCGUGGUGCCGUUCCAC
CACGGCUUCGGCAUGUUCACGACCCUGGGCUACCUCAUCUGCGGCUUCCGGGUGGUCCUGAUGUACCG
GUUCGAGGAGGAGCUGUUCCUGCGGAGCCUGCAGGACUACAAGAUCCAGAGCGCGCUGCUCGUGCCGA
CCCUGUUCAGCUUCUUCGCCAAGAGCACCCUGAUCGACAAGUACGACCUGUCGAACCUGCACGAGAUC
GCCAGCGGGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGGGACGACA
AGCCGGGCGCCGUGGGCAAGGUGGUCCCGUUCUUCGAGGCCAAGGUGGUGGACCUGGACACCGGCAAG
ACCCUGGGCGUGAACCAGCGGGGCGAGCUGUGCGUGCGGGGCCGAUGAUCAUGAGCGGCUACGUGAA
CAACCCGGAGGCCACCAACGCCCUCAUCGACAAGGACGGCUGGCUGCACAGCGGCGACAUCGCCUACU
GGGACGAGGACGAGCACUUCUUCAUCGUCGACCGGCUGAAGUCGCUGAUCAAGUACAAGGGCUACCAG
GUGGCGCCGGCCGAGCUGGAGAGCAUCCUGCUCCAGCACCCCAACAUCUUCGACGCCGGCGUGGCCGG
GCUGCCGGACGACGACGCCGGCGAGCUGCCGGCCGCGGUGGUGGUGCUGGAGCACGGCAAGACCAUGA
CGGAGAAGGAGAUCGUCGACUACGUGGCCAGCCAGGUGACCACCGCCAAGAAGCUGCGGGGCGGCGUG
GUGUUCGUGGACGAGGUCCCGAAGGGCCUGACCGGGAAGCUCGACGCCCGGAAGAUCCGCGAGAUCCU
GAUCAAGGCCAAGAAGGGCGGCAAGAUCGCCGUGUAAGACUAGUUAUAAGACUGACUAGCCCGAUGGG
CCUCCCAACGGGCCCUCCUCCCCUCCUUGCACCGAGAUUAAUAAAAAAAAAAAAAAAAAAAAAAAAAA
AAAAAAAAAAAAAAAAAAAAAAAAAAAAAAAAAAAUGCAUCCCCCCCCCCCCCCCCCCCCCCCC
CCCCCUCUAG

Fig. 1

HA(GC)-muag-A64-C30-histone stem-loop (SEQ ID NO: 2)

GGGAGAAAGCUUACCAUGAAGGCCAUCCUGGUGGUCCUCCUGUACACCUUCGCCACCGCGAACGCCGA
CACGCUGUGCAUCGGCUACCACGCCAACAACAGCACCGACACCGUGGACACCGUGCUCGAGAAGAACG
UCACGGUGACCCACUCCGUGAACCUGCUGGAGGACAAGCACAACGGGAAGCUCUGCAAGCUGCGGGGC
GUCGCCCCGCUGCACCUCGGGAAGUGCAACAUCGCCGGCUGGAUCCUGGGGAACCCGGAGUGCGAGAG
CCUGUCCACCGCGAGCUCCUGGAGCUACAUCGUGGAGACCUCCAGCUCCGACAACGGCACGUGCUACC
CCGGCGACUUCAUCGACUACGAGGAGCUCCGCGAGCAGCUGAGCUCCGUGAGCUCCUUCGAGCGGUUC
GAGAUCUUCCCCAAGACCAGCUCCUGGCCCAACCACGACAGCAACAAGGGGGUCACCGCCGCCUGCCC
GCACGCCGGCGCGAAGUCCUUCUACAAGAACCUGAUCUGGCUCGUGAAGAAGGGGAACAGCUACCCCA
AGCUGUCCAAGAGCUACAUCAACGACAAGGGCAAGGAGGUGCUGGUCCUCUGGGGGAUCCACCACCCC
AGCACCUCCGCCGACCAGCAGAGCCUGUACCAGAACGCCGACGCCUACGUGUUCGUGGGCUCCAGCCG
CUACUCCAAGAAGUUCAAGCCCGAGAUCGCCAUCCGGCCGAAGGUCCGCGACCAGGAGGGCCGGAUGA
ACUACUACUGGACGCUGGUGGAGCCCGGGGACAAGAUCACCUUCGAGGCGACCGGCAACCUCGUGGUC
CCCCGCUACGCCUUCGCCAUGGAGCGGAACGCCGGGAGCGGCAUCAUCUCCGACACCCCCGUGCA
CGACUGCAACACGACCUGCCAGACCCCGAAGGGCGCCAUCAACACCAGCCUGCCCUUCCAGAACAUCC
ACCCCAUCACGAUCGGGAAGUGCCCCAAGUACGUGAAGUCCACCAAGCUGCGCCUCGCGACCGGCCUG
CGGAACGUCCCGAGCAUCCAGUCCCGCGGGCUGUUCGGCGCCAUCGCCGGGUUCAUCGAGGGCGGCUG
GACCGGGAUGGUGGACGGCUGGUACGGGUACCACCACCAGAACGAGCAGGGCAGCGGGUACGCCGCCG
ACCUCAAGUCCACGCAGAACGCGAUCGACGAGAUCACCAACAAGGUGAACAGCGUCAUCGAGAAGAUG
AACACCCAGUUCACCGCCGUGGGCAAGGAGUUCAACCACCUGGAGAAGCGGAUCGAGAACCUGAACAA
GAAGGUCGACGACGGCUUCCUCGACAUCUGGACGUACAACGCCGAGCUGCUGGUGCUCCUGGAGAACG
AGCGCACCCUGGACUACCACGACUCCAACGUGAAGAACCUCUACGAGAAGGUCCGGAGCCAGCUGAAG
AACAACGCCAAGGAGAUCGGGAACGGCUGCUUCGAGUUCUACCACAAGUGCGACAACACCUGCAUGGA
GUCCGUGAAGAACGGGACCUACGACUACCCCAAGUACAGCGAGGAGGCCAAGCUGAACCGCGAGGAGA
UCGACGGCGUGAAGCUCGAGUCCACGCGGAUCUACCAGAUCCUGGCGAUCUACAGCACCGUCGCCAGC
UCCCUGGUGCUCGUGGUCAGCCUGGGGGCCAUCUCCUUCUGGAUGUGCAGCAACGGCUCCCUGCAGUG
CCGCAUCUGCAUCUGACCACUAGUUAUAAGACUGACUAGCCCGAUGGGCCUCCCAACGGGCCCUCCUC
CCCUCCUUGCACCGAGAUUAAUAAAAAAAAAAAAAAAAAAAAAAAAAAAAAAAAAAAAAAAAAAAAAA
AAAAAAAAAAAAAAAAAAAUGCAUCCCCCCCCCCCCCCCCCCCCCCCCCCCCCAAAGGCUCUUUUCA
GAGCCACCAGAAUU

Fig. 2

HsFOLH1 (GC)-muag-A64-C30-histone stem-loop (SEQ ID NO: 3)

GGGAGAAAGCTTACCATGTGGAACCTGCTCCACGAGACCGACAGCGCCGTGGCGACGGCCCGGCGCCC
GCGGTGGCTGTGCGCCGGCGCCCTGGTCCTGGCCGGGGGCTTCTTCCTGCTGGGCTTCCTGTTCGGCT
GGTTCATCAAGTCGAGCAACGAGGCCACCAACATCACCCCCAAGCACAACATGAAGGCCTTCCTCGAC
GAGCTGAAGGCCGAGAACATCAAGAAGTTCCTGTACAACTTCACCCAGATCCCCCACCTGGCCGGGAC
CGAGCAGAACTTCCAGCTGGCCAAGCAGATCCAGAGCCAGTGGAAGGAGTTCGGCCTGGACTCGGTGG
AGCTGGCGCACTACGACGTGCTGCTCAGCTACCCCAACAAGACCCACCCCAACTACATCAGCATCATC
AACGAGGACGGCAACGAGATCTTCAACACCAGCCTGTTCGAGCCCCGCCCCCGGCTACGAGAACGT
GTCGGACATCGTGCCCCCCTTCAGCGCCTTCAGCCCGCAGGGCATGCCCGAGGGGACCTGGTGTACG
TGAACTACGCCCGGACGGAGGACTTCTTCAAGCTGGAGCGCGACATGAAGATCAACTGCAGCGGCAAG
ATCGTGATCGCCCGGTACGGCAAGGTGTTCCGGGGCAACAAGGTGAAGAACGCCCAGCTGGCCGGGGC
CAAGGGCGTGATCCTGTACTCGGACCCCGCCGACTACTTCGCCCCCGGCGTGAAGAGCTACCCCGACG
GCTGGAACCTGCCCGGCGGGGCGTCCAGCGCGGCAACATCCTCAACCTGAACGGCGCCGGCGACCCG
CTGACCCCCGGGTACCCCGCGAACGAGTACGCCTACCGGCGGGGCATCGCCGAGGCCGTGGGCCTGCC
CAGCATCCCCGTGCACCCGATCGGCTACTACGACGCCCAGAAGCTGCTGGAGAAGATGGGCGGGAGCG
CCCCGCCCGACTCGAGCTGGCGGGGCAGCCTGAAGGTGCCCTACAACGTGGGCCCCGGCTTCACCGGG
AACTTCTCGACCCAGAAGGTGAAGATGCACATCCACAGCACCAACGAGGTGACCCGCATCTACAACGT
GATCGGCACCCTGCGGGGCGCCGTGGAGCCCGACCGGTACGTGATCCTCGGCGGGCACCGCGACAGCT
GGGTGTTCGGCGGCATCGACCCCAGAGCGGCGCCGCCGTGGTCCACGAGATCGTGCGGTCGTTCGGC
ACCCTGAAGAAGGAGGGGTGGCGGCCCCGCCGGACGATCCTGTTCGCCAGCTGGGACGCGGAGGAGTT
CGGCCTGCTGGGCAGCACCGAGTGGGCCGAGGAGAACAGCCGGCTGCTGCAGGAGCGGGGCGTGGCCT
ACATCAACGCCGACTCGAGCATCGAGGGCAACTACACCCTCCGCGTGGACTGCACCCCGCTGATGTAC
AGCCTGGTGCACAACCTGACCAAGGAGCTGAAGAGCCCCGACGAGGGGTTCGAGGGCAAGTCGCTGTA
CGAGAGCTGGACCAAGAAGAGCCCCTCGCCCGAGTTCAGCGGCATGCCCGGATCAGCAAGCTGGGCA
GCGGGAACGACTTCGAGGTGTTCTTCCAGCGGCTGGGCATCGCCTCGGGCCGCGCCCGGTACACCAAG
AACTGGGAGACGAACAAGTTCAGCGGCTACCCCTCTACCACAGCGTGTACGAGACCTACGAGCTGGT
GGAGAAGTTCTACGACCCCATGTTCAAGTACCACCTGACCGTGGCCCAGGTGCGGGGCGGGATGGTGT
TCGAGCTGGCCAACAGCATCGTGCTGCCCTTCGACTGCCGCGACTACGCCGTCGTGCTGCGGAAGTAC
GCCGACAAGATCTACTCGATCAGCATGAAGCACCCCAGGAGATGAAGACCTACAGCGTGAGCTTCGA
CTCGCTGTTCAGCGCGGTGAAGAACTTCACCGAGATCGCCAGCAAGTTCTCGGAGCGGCTCCAGGACT
TCGACAAGAGCAACCCGATCGTGCTGCGCATGATGAACGACCAGCTGATGTTCCTGGAGCGGGCCTTC
ATCGACCCCCTGGGCCTGCCCGACCGGCCCTTCTACCGGCACGTGATCTACGCCCCCAGCAGCCACAA
CAAGTACGCCGGCGAGTCGTTCCCGGGGATCTACGACGCCCTGTTCGACATCGAGAGCAAGGTGGACC
CCAGCAAGGCCTGGGGCGAGGTGAAGCGCCAGATCTACGTGGCCGCCTTCACCGTGCAGGCCGCGGCC
GAGACCCTGAGCGAGGTGGCCTGACCACTAGTTATAAGACTGACTAGCCCGATGGGCCTCCCAACGGG
CCCTCCTCCCTCCTTGCACCGAGATTAATAAAAAAAAAAAAAAAAAAAAAAAAAAAAAAAAAAAAAAA
AAAAAAAAAAAAAAAAAAAAAAAATATTCCCCCCCCCCCCCCCCCCCCCCCCCCCCCTCTAGACA
ATTGGAATT

Fig. 3

RAV-G(GC)-muag-A64-C30-histone stem-loop (SEQ ID NO:9)

GGGAGAAAGCUUACCAUGGUGCCCCAGGCCCUGCUCUUCGUCCCGCUGCUGGUGUUCCCC
CUCUGCUUCGGCAAGUUCCCCAUCUACACCAUCCCCGACAAGCUGGGGCCGUGGAGCCCC
AUCGACAUCCACCACCUGUCCUGCCCCAACAACCUCGUGGUCGAGGACGAGGGCUGCACC
AACCUGAGCGGGUUCUCCUACAUGGAGCUGAAGGUGGGCUACAUCAGCGCCAUCAAGAUG
AACGGGUUCACGUGCACCGGCGUGGUCACCGAGGCGGAGACCUACACGAACUUCGUGGGC
UACGUGACCACCACCUUCAAGCGGAAGCACUUCCGCCCCACGCCGGACGCCUGCCGGGCC
GCCUACAACUGGAAGAUGGCCGGGGACCCCGCUACGAGGAGUCCCUCCACAACCCCUAC
CCCGACUACCACUGGCUGCGGACCGUCAAGACCACCAAGGAGAGCCUGGUGAUCAUCUCC
CCGAGCGUGGCGGACCUCGACCCCUACGACCGCUCCCUGCACAGCCGGGUCUUCCCCGGC
GGGAACUGCUCCGGCGUGGCCGUGAGCUCCACGUACUGCAGCACCAACCACGACUACACC
AUCUGGAUGCCCGAGAACCCGCGCCUGGGGAUGUCCUGCGACAUCUUCACCAACAGCCGG
GGCAAGCGCGCCUCCAAGGGCAGCGAGACGUGCGGGUUCGUCGACGAGCGGGGCCUCUAC
AAGUCCCUGAAGGGGGCCUGCAAGCUGAAGCUCUGCGGCGUGCUGGGCCUGCGCCUCAUG
GACGGGACCUGGGUGGCGAUGCAGACCAGCAACGAGACCAAGUGGUGCCCCCCCGGCCAG
CUGGUCAACCUGCACGACUUCCGGAGCGACGAGAUCGAGCACCUCGUGGUGGAGGAGCUG
GUCAAGAAGCGCGAGGAGUGCCUGGACGCCCUCGAGUCCAUCAUGACGACCAAGAGCGUG
UCCUUCCGGCGCCUGAGCCACCUGCGGAAGCUCGUGCCCGGGUUCGGCAAGGCCUACACC
AUCUUCAACAAGACCCUGAUGGAGGCCGACGCCCACUACAAGUCCGUCCGCACGUGGAAC
GAGAUCAUCCCGAGCAAGGGGUGCCUGCGGGUGGGCGGCCGCUGCCACCCCCACGUCAAC
GGGGUGUUCUUCAACGGCAUCAUCCUCGGGCCCGACGGCAACGUGCUGAUCCCCGAGAUG
CAGUCCAGCCUGCUCCAGCAGCACAUGGAGCUGCUGGUCUCCAGCGUGAUCCCGCUCAUG
CACCCCCUGGCGGACCCCUCCACCGUGUUCAAGAACGGGGACGAGGCCGAGGACUUCGUC
GAGGUGCACCUGCCCGACGUGCACGAGCGGAUCAGCGGCGUCGACCUCGGCCUGCCGAAC
UGGGGGAAGUACGUGCUGCUCUCCGCCGGCGCCCUGACCGCCCUGAUGCUGAUCAUCUUC
CUCAUGACCUGCUGGCGCCGGGUGAACCGGAGCGAGCCCACGCAGCACAACCUGCGCGGG
ACCGGCCGGGAGGUCUCCGUGACCCCGCAGAGCGGGAAGAUCAUCUCCAGCUGGGAGUCC
UACAAGAGCGGCGGCGAGACCGGGCUGUGAGGACUAGUUAUAAGACUGACUAGCCCGAUG
GGCCUCCCAACGGGCCCUCCUCCCCUCCUUGCACCGAGAUUAAUAAAAAAAAAAAAAAAA
AAAAAAAAAAAAAAAAAAAAAAAAAAAAAAAAAAAAAAAAAAAAAAAAUGCAUCCCCCCC
CCCCCCCCCCCCCCCCCCCCCCCCAAAGGCUCUUUUCAGAGCCACCAGAAUU

Fig. 4

A)

B)

A)
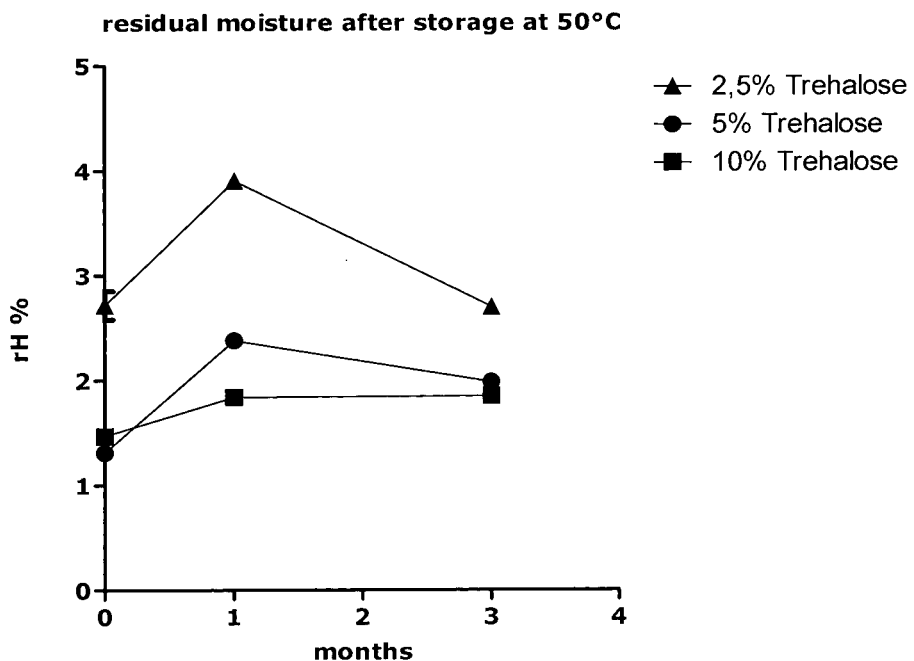
B)
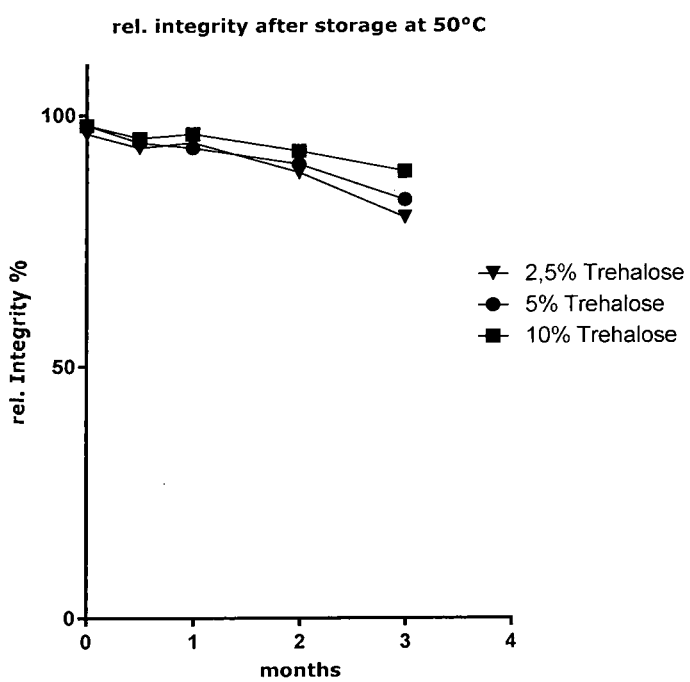
Fig. 6

A)

B)
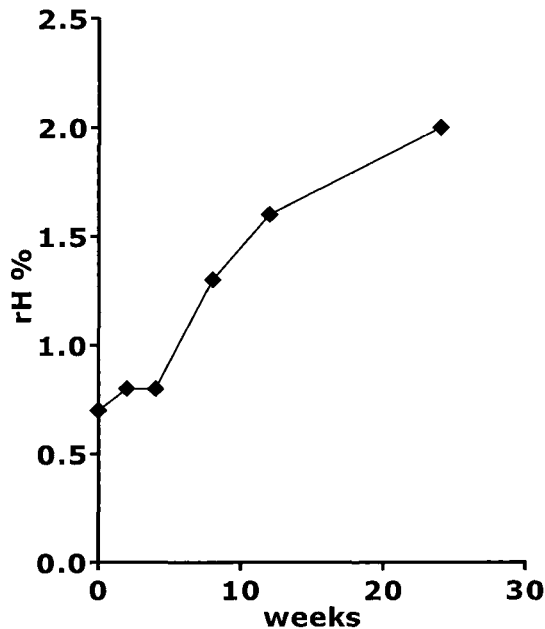
C)
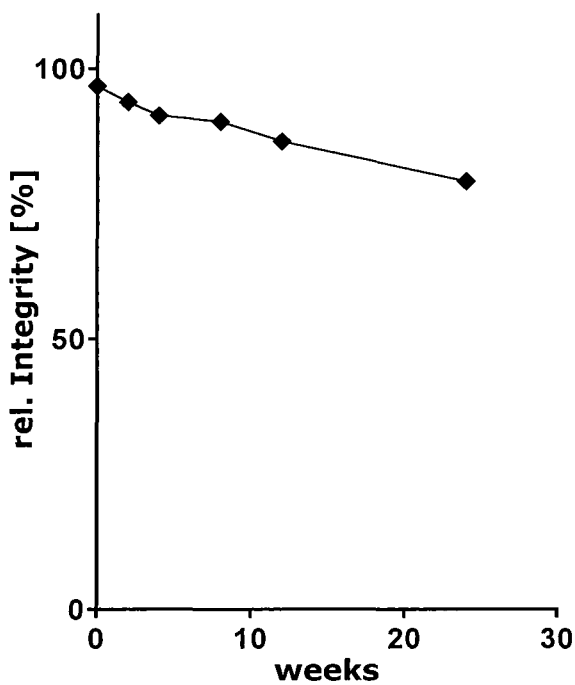
Fig. 7 continued

A)
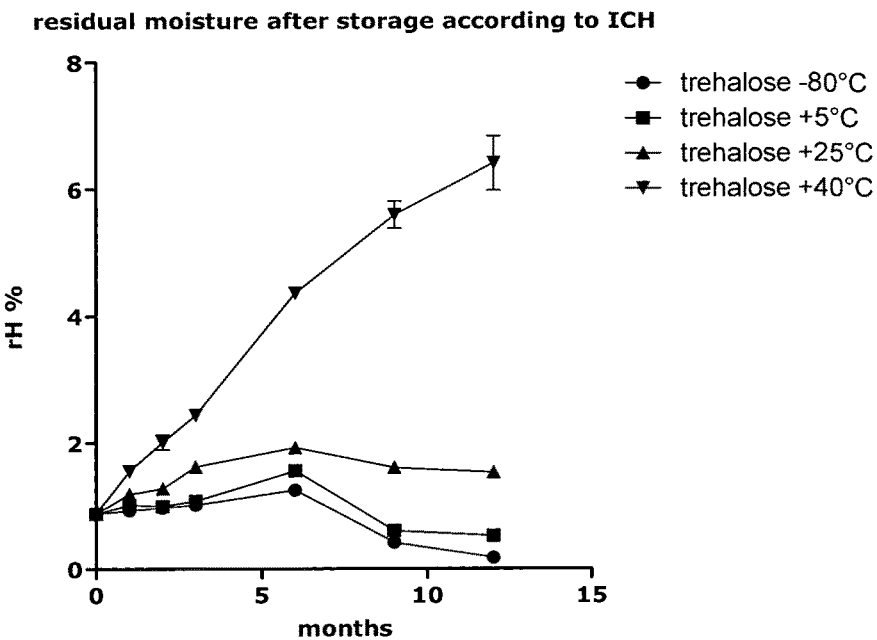
B)
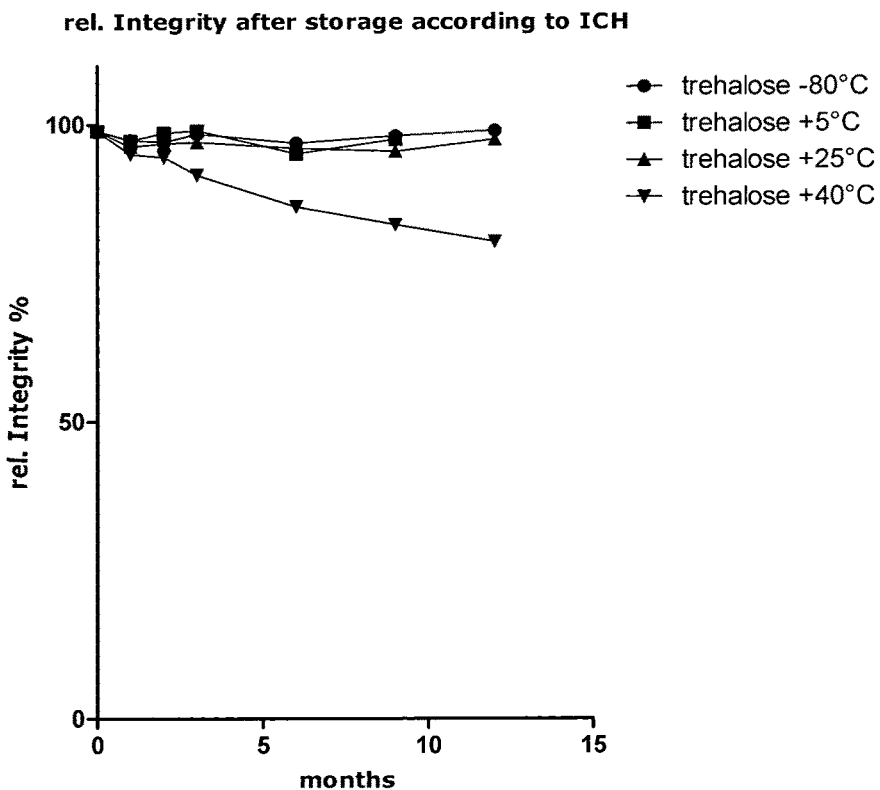
Fig. 8

C)
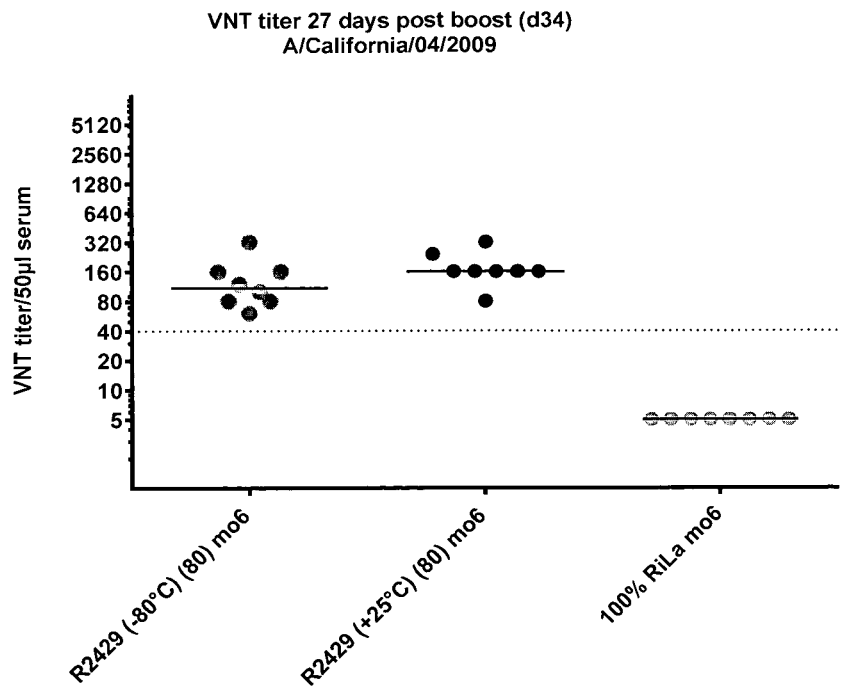
D)
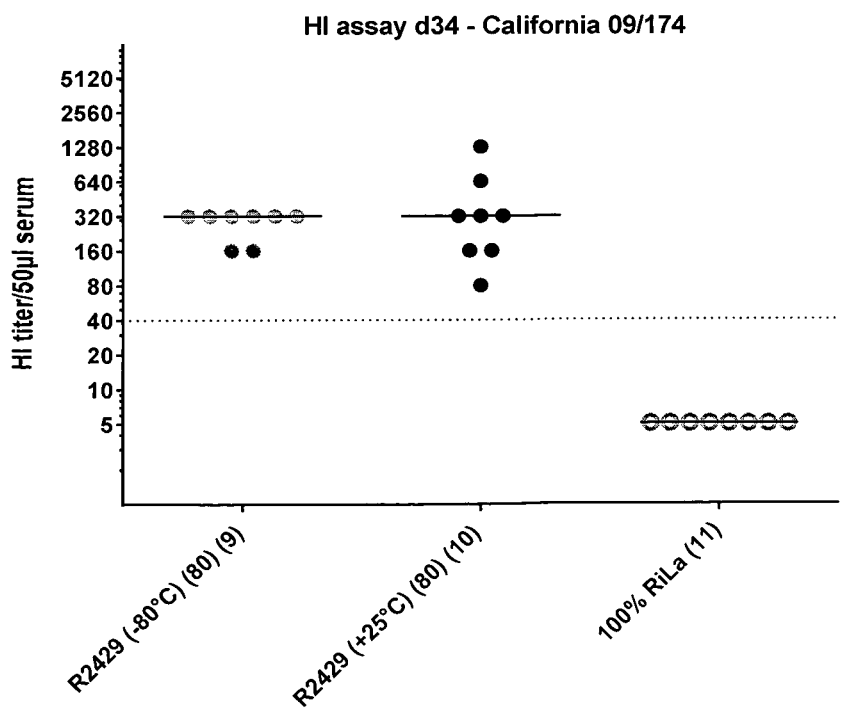
Fig. 8 continued

SEQUENCE LISTING

<160> NUMBER OF SEQ ID NOS: 9

<210> SEQ ID NO 1
<211> LENGTH: 1846
<212> TYPE: RNA
<213> ORGANISM: Artificial Sequence
<220> FEATURE:
<223> OTHER INFORMATION: PpLuc(GC)-muag-A64-C30

<400> SEQUENCE: 1

| | | |
|---|---|---|
| gggagaaagc uugaggaugg aggacgccaa gaacaucaag aagggcccgg cgcccuucua | 60 |
| cccgcuggag gacgggaccg ccggcgagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacggcc ugaacaccaa | 240 |
| ccaccggauc guggugugcu cggagaacag ccugcaguuc uucaugccgg ugcugggcgc | 300 |
| ccucuucauc ggcguggccg ucgccccggc gaacgacauc uacaacgagc gggagcugcu | 360 |
| gaacagcaug gggaucagcc agccgaccgu ggucuucgug agcaagaagg ccugcagaa | 420 |
| gauccugaac gugcagaaga gcugcccau cauccagaag aucaucauca uggacagcaa | 480 |
| gaccgacuac cagggcuucc agucgaugua cacguucgug accagccacc ucccgccggg | 540 |
| cuucaacgag uacgacuucg ucccggagag cuucgaccgg acaagacca ucgcccugau | 600 |
| caugaacagc agcggcagca ccggccugcc gaaggggug gcccugccgc accggaccgc | 660 |
| cugcgugcgc uucucgcacg cccgggaccc caucuucggc aaccagauca ucccggacac | 720 |
| cgccauccug agcguggugc cguuccacca cggcuucggc auguucacga cccugggcua | 780 |
| ccucaucugc ggcuuccggg uggccugau guaccgguuc gaggaggagc uguuccugcg | 840 |
| gagccugcag gacuacaaga uccagagcgc gcugcucgug ccgacccugu ucagcuucuu | 900 |
| cgccaagagc acccugaucg acaagucacg ccugucgaac cugcacgaga ucgccagcgg | 960 |
| gggcgccccg cugagcaagg aggugggcga ggccguggcc aagcgguucc accucccggg | 1020 |
| cauccgccag ggcuacggcc ugaccgagac cacgagcgcg auccugauca cccccgaggg | 1080 |
| ggacgacaag ccgggcgccg ugggcaaggu ggucccguuc uucgaggcca gguggugga | 1140 |
| ccuggacacc ggcaagaccc ugggcgugaa ccagcgggc gagcugugcg ugcgggggcc | 1200 |
| gaugaucaug agcgggcuacg ugaacaaccc ggaggccacc aacgcccuca ucgacaagga | 1260 |
| cggcuggcug cacagcggcg acaucgccua cuggggacgag gacgagcacu ucuucaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccgggc ugccggacga | 1440 |
| cgacgccggc gagcugccgg ccgcgguggu ggugcuggag cacggcaaga ccaugacgga | 1500 |
| gaaggagauc gucgacuacg uggccagcca ggugaccacc gccaagaagc ugcggggcgg | 1560 |
| cguggguuuc guggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |
| agacugacua gcccgauggg ccucccaacg ggcccuccuc cccuccuugc accgagauua | 1740 |
| auaaaaaaa aaaaaaaaa aaaaaaaaa aaaaaaaaa aaaaaaaaa aaaaaaaaa | 1800 |
| aaaaaaugca uccccccccc ccccccccc ccccccccc cucuag | 1846 |

<210> SEQ ID NO 2
<211> LENGTH: 1918
<212> TYPE: RNA
<213> ORGANISM: Artificial Sequence
<220> FEATURE:
<223> OTHER INFORMATION: HA(GC)-muag-A64-C30-histone stem-loop

<400> SEQUENCE: 2

```
gggagaaagc uuaccaugaa ggccauccug gugguccucc uguacaccuu cgccaccgcg    60
aacgccgaca cgcugugcau cggcuaccac gccaacaaca gcaccgacac cguggacacc   120
gugcucgaga agaacgucac ggugacccac uccgugaacc ugcuggagga caagcacaac   180
gggaagcucu gcaagcugcg gggcgucgcc ccgcugcacc ucgggaagug caacaucgcc   240
ggcuggaucc uggggaaccc ggagugcgag agccugucca ccgcgagcuc cuggagcuac   300
aucguggaga ccuccagcuc cgacaacggc acgugcuacc ccggcgacuu caucgacuac   360
gaggagcucc gcgagcagcu gagcccgug agcuccuucg agcgguucga gaucuucccc   420
aagaccagcu ccuggcccaa ccacgacagc aacaaggggg ucaccgccgc cugcccgcac   480
gccggcgcga aguccuucua caagaaccug aucuggcucg ugaagaaggg gaacagcuac   540
cccaagcugu ccaagagcua caucaacgac aagggcaagg aggugcuggu ccucuggggg   600
auccaccacc ccagcaccuc cgccgaccag cagagccugu accagaacgc cgacgccuac   660
guguucgugg gcuccagccg cuacuccaag aaguucaagc ccgagaucgc caucggccg    720
aagguccgcg accaggaggg ccggaugaac uacuacugga cgcuggugga gcccggggac   780
aagaucaccu ucgaggcgac cggcaacccc guggucccccc gcuacgccuu cgccauggag   840
cggaacgccg ggagcggcau caucaucucc gacacccccg ugcacgacug caacacgacc   900
ugccagaccc cgaagggcgc caucaacacc agccugcccu ccagaacau ccaccccauc    960
acgaucggga agugccccaa guacgugaag uccaccaagc ugcgccucgc gaccggccug  1020
cggaacgucc cgagcaucca guccgcgggg cuguucggcg ccaucgccgg guucaucgag  1080
ggcggcugga ccgggauggu ggacggcugg uacggguacc accaccagaa cgagcagggc  1140
agcgggguacg ccgccgaccu caaguccacg cagaacgcga ucgacgagau caccaacaag  1200
gugaacagcg ucaucgagaa gaugaacacc caguucaccg ccguggcaa ggaguucaac  1260
caccuggaga gcggaucga gaaccugaac aagaaggucg acgacggcuu ccucgacauc  1320
uggacguaca acgccgagcu gcuggugcuc cuggagaacg agcgcacccu ggacuaccac  1380
gacuccaacg ugaagaaccu cuacgagaag guccggagcc agcugaagaa caacgccaag  1440
gagaucggga acggcugcuu cgaguucuac cacaagugcg acaacaccug cauggagucc  1500
gugaagaacg ggaccuacga cuacccaag uacagcgagg aggccaagcu gaaccgcgag  1560
gagaucgacg gcgugaagcu cgaguccacg cggaucuacc agauccuggc gaucuacagc  1620
accgucgcca gcucccuggu gcucgugguc agccuggggg ccaucuccuu cuggaugugc  1680
agcaacggcu cccugcagug ccgcaucugc aucgaccac uaguuauaag acugacuagc  1740
ccgaugggcc ucccaacggg cccuccuccc cuccuugcac cgagauuaau aaaaaaaaaa  1800
aaaaaaaaaa aaaaaaaaaa aaaaaaaaaa aaaaaaaaaa aaaaaaaaaa aaaaugcauc  1860
cccccccccc cccccccccc cccccccccc aaaggcucuu uucagagcca ccagaauu    1918
```

<210> SEQ ID NO 3
<211> LENGTH: 2457
<212> TYPE: DNA
<213> ORGANISM: Artificial Sequence
<220> FEATURE:
<223> OTHER INFORMATION: HsFOLH1 (GC)-muag-A64-C30-histone stem-loop

<400> SEQUENCE: 3

```
gggagaaagc ttaccatgtg gaacctgctc cacgagaccg acagcgccgt ggcgacggcc       60
cggcgcccgc ggtggctgtg cgccggcgcc ctggtcctgg ccgggggctt cttcctgctg      120
ggcttcctgt tcggctggtt catcaagtcg agcaacgagg ccaccaacat caccccaag       180 cacaacatga aggccttcct cgacgagctg aaggccgaga acatcaagaa gttcctgtac      240
aacttcaccc agatccccca cctggccggg accgagcaga acttccagct ggccaagcag      300
atccagagcc agtggaagga gttcggcctg gactcggtgg agctggcgca ctacgacgtg      360
ctgctcagct accccaacaa gacccacccc aactacatca gcatcatcaa cgaggacggc      420
aacgagatct tcaacaccag cctgttcgag cccccgcccc ccggctacga gaacgtgtcg      480
gacatcgtgc cccccttcag cgccttcagc ccgcagggca tgcccgaggg ggacctggtg      540
tacgtgaact acgcccggac ggaggacttc ttcaagctgg agcgcgacat gaagatcaac      600
tgcagcggca agatcgtgat cgcccggtac ggcaaggtgt tccggggcaa caaggtgaag      660
aacgcccagc tggccggggc caagggcgtg atcctgtact cggaccccgc cgactacttc      720 gccccggcg tgaagagcta ccccgacggc tggaacctgc ccggcggggg cgtccagcgc      780
ggcaacatcc tcaacctgaa cggcgccggc gacccgctga ccccgggta ccccgcgaac      840 gagtacgcct accggcgggg catcgccgag gccgtgggcc tgcccagcat ccccgtgcac      900
ccgatcggct actacgacgc ccagaagctg ctggagaaga tgggcgggag cgccccgccc      960
gactcgagct ggcggggcag cctgaaggtg ccctacaacg tgggcccccgg cttcaccggg     1020 aacttctcga cccagaaggt gaagatgcac atccacagca ccaacgaggt gacccgcatc     1080
tacaacgtga tcggcaccct gcggggcgcc gtggagcccg accggtacgt gatcctcggc     1140
gggcaccgcg acagctgggt gttcggcggc atcgacccc agagcggcgc cgccgtggtc     1200
cacgagatcg tgcggtcgtt cggcaccctg aagaaggagg ggtggcggcc ccgccggacg     1260
atcctgttcg ccagctggga cgcggaggag ttcggcctgc tgggcagcac cgagtgggcc     1320
gaggagaaca gccggctgct gcaggagcgg ggcgtggcct acatcaacgc cgactcgagc     1380
atcgagggca actacaccct ccgcgtggac tgcaccccgc tgatgtacag cctggtgcac     1440
aacctgacca aggagctgaa gagccccgac gaggggttcg agggcaagtc gctgtacgag     1500
agctggacca agaagagccc ctcgcccgag ttcagcggca tgccccggat cagcaagctg     1560
ggcagcggga acgacttcga ggtgttcttc cagcggctgg gcatcgcctc gggccgcgcc     1620
cggtacacca agaactggga gacgaacaag ttcagcggct acccctcta ccacagcgtg     1680 tacgagacct acgagctggt ggagaagttc tacgacccca tgttcaagta ccacctgacc     1740
gtggcccagg tgcggggcgg gatggtgttc gagctggcca acagcatcgt gctgcccttc     1800
gactgccgcg actacgccgt cgtgctgcgg aagtacgccg acaagatcta ctcgatcagc     1860
atgaagcacc cccaggagat gaagacctac agcgtgagct cgactcgct gttcagcgcg     1920 gtgaagaact tcaccgagat cgccagcaag ttctcggagc ggctccagga cttcgacaag     1980
agcaacccga tcgtgctgcg catgatgaac gaccagctga tgttcctgga gcgggccttc     2040
atcgaccccc tgggcctgcc cgaccggccc ttctaccggc acgtgatcta cgcccccagc     2100
agccacaaca agtacgccgg cgagtcgttc cggggatct acgacgccct gttcgacatc     2160
gagagcaagg tggaccccag caaggcctgg ggcgaggtga agcgccagat ctacgtggcc     2220
gccttcaccg tgcaggccgc ggccgagacc ctgagcgagg tggcctgacc actagttata     2280
agactgacta gcccgatggg cctcccaacg ggccctcctc ccctccttgc accgagatta     2340
ataaaaaaaa aaaaaaaaaa aaaaaaaaaa aaaaaaaaaa aaaaaaaaaa aaaaaaaaaa     2400
```
aaaaaatatt ccccccccccc cccccccccc ccccccccccc tctagacaat tggaatt    2457

<210> SEQ ID NO 4
<211> LENGTH: 42
<212> TYPE: DNA
<213> ORGANISM: Artificial Sequence
<220> FEATURE:
<223> OTHER INFORMATION: 5'-UTR element

<400> SEQUENCE: 4
ggcgctgcct acggaggtgg cagccatctc cttctcggca tc    42

<210> SEQ ID NO 5
<211> LENGTH: 186
<212> TYPE: DNA
<213> ORGANISM: Artificial Sequence
<220> FEATURE:
<223> OTHER INFORMATION: 3'-UTR element of human albumin gene

<400> SEQUENCE: 5
catcacattt aaaagcatct cagcctacca tgagaataag agaaagaaaa tgaagatcaa    60
tagcttattc atctctttt cttttttcgtt ggtgtaaagc caacaccctg tctaaaaaac    120
ataaatttct ttaatcattt tgcctctttt ctctgtgctt caattaataa aaaatggaaa    180
gaacct    186

<210> SEQ ID NO 6
<211> LENGTH: 44
<212> TYPE: DNA
<213> ORGANISM: Artificial Sequence
<220> FEATURE:
<223> OTHER INFORMATION: 3' UTR element of an alpha-globin gene

<400> SEQUENCE: 6
gcccgatggg cctcccaacg ggccctcctc ccctccttgc accg    44

<210> SEQ ID NO 7
<211> LENGTH: 24
<212> TYPE: DNA
<213> ORGANISM: Artificial Sequence
<220> FEATURE:
<223> OTHER INFORMATION: Histone stem-loop

<400> SEQUENCE: 7
caaaggctct tttcagagcc acca    24

<210> SEQ ID NO 8
<211> LENGTH: 24
<212> TYPE: RNA
<213> ORGANISM: Artificial Sequence
<220> FEATURE:
<223> OTHER INFORMATION: Histone stem-loop

<400> SEQUENCE: 8
caaaggcucu uuucagagcc acca    24

<210> SEQ ID NO 9
<211> LENGTH: 1792
<212> TYPE: RNA
<213> ORGANISM: Artificial Sequence
<220> FEATURE:
<223> OTHER INFORMATION: RAV-G(GC)-muag-A64-C30-histone stem-loop

<400> SEQUENCE: 9

```
gggagaaagc uuaccauggu gccccaggcc cugcucuucg ucccgcugcu gguguucccc        60
cucugcuucg gcaaguuccc caucuacacc aucccegaca agcuggggcc guggagcccc       120
aucgacaucc accaccuguc cugcccaac aaccucgugg ucgaggacga gggcugcacc       180
aaccugagcg gguucuccua cauggagcug aaggugggcu acaucagcgc caucaagaug       240
aacggguuca cgugcaccgg cguggucacc gaggcggaga ccuacacgaa cuucgugggc       300
uacgugacca ccaccuucaa gcggaagcac uuccgcccca cgccggacgc cugccgggcc       360
gccuacaacu ggaagauggc cggggacccc cgcuacgagg aguccuccca caaccccuac       420
cccgacuacc acuggcugcg gaccgucaag accaccaagg agagccuggu gaucaucucc       480
ccgagcgugg cggaccucga ccccuacgac cgcucccugc acagccgggu cuuccccggc       540
gggaacugcu ccggcguggc cgugagcucc acuacugca gcaccaacca cgacuacacc       600
aucuggaugc ccgagaaccc gcgccugggg augucCugc acaucuucac caacagccgg       660
ggcaagcgcg ccuccaaggg cagcgagacg ugcggguucg ucgacgagcg gggccucuac       720
aagucccuga aggggccug caagcugaag cucuCcggcg ugcugggccu gcgccucaug       780
gacgggaccu gguggcgau gcagaccagc aacgagacca aguggugccc ccccggccag       840
cuggucaacc ugcacgacuu ccggagcgac gagaucgagc accucguggu ggaggagcug       900
gucaagaagc gcgaggagug ccuggacgcc cucgagucca ucaugacgac caagagcgug       960
uccuuccggc gccugagcca ccugcggaag cucgugcccg gguucggcaa ggccuacacc      1020
aucuucaaca agaccCugau ggaggccgac gcccacuaca aguccguccg cacguggaac      1080
gagaucaucc cgagcaaggg gugccugcgg gugggcggcc gcugccaccc ccacgucaac      1140 ggguguucu ucaacggcau caaccucggg cccgacggca acgugcugau ccccgagaug      1200
caguccagcc ugcuccagca gcacauggag cugcuggucu ccagcgugau cccgcucaug      1260
caccccuugg cggacccuc caccguguuc aagaacgggg acgaggccga ggacuucguc      1320
gaggugcacc ugcccgacgu gcacgagcgg aucagcggcg ucgaccucgg ccugccgaac      1380 uggggaagu acgugcugcu cuccgccggc gcccugaccg cccugaugcu gaucaucuuc      1440
cucaugaccu gcuggcgccg ggugaaccgg agcgagccca cgcagcacaa ccugcgcggg      1500
accggccggg aggucuccgu gaccccgcag agcgggaaga ucaucuccag cugggagucc      1560
uacaagagcg gcgacgagac cgggcuguga ggacuaguua uaagacugac uagcccgaug      1620 ggcucccaa cgggcccucc uccccuccuu gcaccgagau uaauaaaaaa aaaaaaaaaa      1680 aaaaaaaaa aaaaaaaaaa aaaaaaaaaa aaaaaaaaaa aaaaaaaaug caucccccc      1740 cccccccccc cccccccccc cccaaaggc ucuuucaga gccaccagaa uu            1792
```

LYOPHILIZATION OF RNA

This application is a national phase application under 35 U.S.C. § 371 of International Application No. PCT/EP2016/000622, filed Apr. 15, 2016, which claims benefit of International Application No. PCT/EP2015/000818, filed Apr. 17, 2015, the entire contents of each of which are hereby incorporated by reference.

The present invention is directed to the field of RNA formulation, in particular to lyophilization of RNA. The invention provides a method for lyophilization of RNA. The present invention further concerns a lyophilized composition obtainable by the inventive method, a pharmaceutical composition, a vaccine and a kit or kit of parts. Moreover, the present invention provides a novel use of a lyoprotectant for lyophilizing RNA, the use of the inventive method in the manufacture of a medicament as well as the first and second medical use of the composition obtainable by the inventive method, the pharmaceutical composition, the vaccine or the kit or kit of parts according to the invention.

In gene therapy as well as in many other therapeutically relevant biochemical and biotechnological applications, nucleic acids are used for therapeutic and diagnostic purposes. As an example, rapid progress has occurred in recent years in the field of gene therapy and promising results have been achieved. Nucleic acids are therefore regarded as important tools for gene therapy and prophylactic and therapeutic vaccination against, for instance, infectious and malignant diseases.

Nucleic acids, both DNA and RNA, have been used widely in gene therapy, either in naked, or in complexed form. In this context, the application of nucleic acids and particularly of RNA for therapeutic vaccination is revised permanently.

The application of RNA represents a favored tool in modern molecular medicine, which also exhibits some superior properties over the application of DNA. As generally known, transfection of DNA molecules may lead to serious complications. For example, application of DNA molecules bears the risk that the DNA integrates into the host genome. Integration of foreign DNA into the host genome can have an influence on the expression of host genes and can trigger the expression of an oncogene or the inactivation of a tumor suppressor gene. Furthermore, an essential gene—and, as a consequence, the product of such an essential gene—may also be inactivated by the integration of the foreign DNA into the coding region of the gene. The result of such an event may be particularly dangerous if the DNA is integrated into a gene, which is involved in regulation of cell growth. Notwithstanding the risks associated with its application, DNA still represents an important tool. However, these risks do not occur if RNA, particularly mRNA, is used instead of DNA. An advantage of using RNA rather than DNA is that no virus-derived promoter element has to be administered in vivo and no integration into the genome may occur. Furthermore, the RNA, in order to exert its function, does not need to overcome the barrier to the nucleus.

However, a main disadvantage of the use of RNA is its instability. Even though it is understood that DNA, such as naked DNA, when introduced into a patient circulatory system, is typically not stable and therefore may have little chance of affecting most disease processes (see e.g. Poxon et al., Pharmaceutical development and Technology, 5(1), 115-122 (2000)), the problem of stability becomes even more prominent in the case of RNA. It is generally known that the physico-chemical stability of RNA molecules in solution is extremely low. RNA is susceptible to hydrolysis by ubiquitous ribonucleases or by divalent cations and is typically rapidly degraded, e.g. already after a few hours or days in solution. Rapid degradation occurs even in the absence of RNases, e.g. when RNA is stored in solution at room temperature for a few hours or days.

To avoid such rapid degradation, RNA (in solution) is typically stored at −20° C. or even −80° C. and under RNAse free conditions to prevent degradation of the RNA. Such storage conditions, however, do not sufficiently prevent a loss of function over time. Additionally, applying such conditions is very cost-intensive, especially for shipping and storage, e.g. whenever such low temperatures have to be guaranteed.

One further method for stabilization RNA comprises lyophilization or freeze-drying of the RNA. Lyophilization is a method known and recognized worldwide, which is used to enhance storage stability of temperature sensitive biomolecules. During lyophilization, a solvent, such as water, is typically removed from a frozen sample via sublimation.

The process of lyophilization is usually characterized by a primary and a secondary drying step. During the primary drying step, free, i.e. unbound, water surrounding the biomolecule and optionally further components, evaporates from the frozen solution. Subsequently, water, which is bound by the biomolecule on a molecular basis, may be removed in a secondary drying step by adding thermal energy. In both cases, the hydration sphere around the biomolecule is lost.

During lyophilization, a sample containing a biomolecule is initially cooled below the freezing point of the solution and accordingly of the water contained therein. As a result, the water freezes. Depending, amongst other parameters, on temperature, cooling rate (freezing rate), and the time for freezing, crystals may be formed. This exerts physical stress on the biomolecule and other components of the solution, which may lead to a damage of the biomolecule such as—in the case of a nucleic acid—breakage of strands, loss of supercoiling, etc. Furthermore, due to the decrease of volume and loss of the hydration sphere, autocatalytic degradation processes are favored e.g. by traces of transition metals. In addition, the concentration of traces of acids and bases can result in significant changes of the pH value.

Lyophilization involves two types of stress, namely freezing and drying. Both types of stress are known to damage nucleic acids, such as non-viral vectors or plasmid DNA. In the literature, a number of cryoprotectants and lyoprotectants are discussed for lyophilization purposes to prevent these damages. In this context, cryoprotectants are understood as excipients, which allow influencing the structure of the ice and/or the eutectical temperature or glass transition temperature of the mixture. Lyoprotectants are typically excipients, which partially or totally replace the hydration sphere around a molecule and may thus at least partially prevent catalytic and hydrolytic processes.

In the specific context of DNA, lyophilization causes the removal of the hydration sphere around the DNA, wherein it appears that there are approximately 20 water molecules per nucleotide pair bound most tightly to DNA. These water molecules do not form an ice-like structure upon low-temperature cooling. Upon DNA dehydration in the presence of hygroscopic salts at 0% relative humidity, only five or six water molecules remain (see e.g. Tao et al., Biopolymers, 28, 1019-1030 (1989)). Lyophilization may increase the stability of DNA under long-term storage, but may also cause some damage due to the initial lyophilization process, potentially through changes in the DNA secondary structure, breaks of the nucleic acid chain(s) or the concentration of reactive elements such as contaminating metals. Lyophilization can also cause damage upon the initial lyophilization process in other nucleic acid, e.g. RNA. Agents that can substitute for non-freezable water, such as some carbohydrates, can demonstrate cryoprotective properties with respect to DNA and other molecules during lyophilization of intact bacteria (see e.g. Israeli et al, Cryobiology, 30, 519-523 (1993); or Rudolph et al, Arch. Biochem. Biophys., 245, 134-143 (1986)).

During lyophilization, specific carbohydrates, such as several sugars, appear to play a central role in the stabilization of nucleic acid molecules. However, when using cryoprotectants and lyoprotectants, no general rule may be applied with respect to their impact on different groups of compounds. Therefore, an optimized formulation has to be found by using empirical methods.

In this context, specific carbohydrates are utilized in the art as lyoprotective substances for enhancing stability of nucleic acids during lyophilization. They exhibit an effect on storage stability after lyophilisation of pure nucleic acids or nucleic acid (sequence) complexes (see e.g. Maitani, Y., Y. Aso, et al. (2008), Int J Pharm 356(1-2): 69-75; Quaak, S. G., J. H. van den Berg, et al. (2008), Eur J Pharm Biopharm 70(2): 429-38; Jones, K. L., D. Drane, et al. (2007), Biotechniques 43(5): 675-81; Molina, M. C., S. D. Allison, et al. (2001), J Pharm Sci 90(10): 1445-55; and Allison, S. D. and T. J. Anchordoquy (2000), J Pharm Sci 89(5): 682-91). Lyoprotective properties are particularly described for sucrose, glucose, and trehalose. They allow to restore at least in part the transfection efficiency, which is otherwise lost in many cases after lyophilisation (see Maitani et al, 2008, supra; Yadava, P., M. Gibbs, et al. (2008). AAPS PharmSciTech 9(2): 335-41; Werth, S., B. Urban-Klein, et al. (2006), J Control Release 112(2): 257-70; Brus, C., E. Kleemann, et al. (2004), J Control Release 95(1): 119-31; Poxon, S. W. and J. A. Hughes (2000), Pharm Dev Technol 5(1): 115-22; Anchordoquy, T. J., J. F. Carpenter, et al. (1997), Arch Biochem Biophys 348(1): 199-206). Sugars are able to prevent loss in activity due to the lyophilization process mainly by preventing particle fusion/aggregation especially in the case of liposome complexed nucleic acids (see Yadava et al, 2008, supra; Katas, H., S. Chen, et al. (2008), J Microencapsul: 1-8; Molina et al, supra, 2001).

Particularly, Poxon et al. (2000, supra) investigated the effect of lyophilization on plasmid DNA activity. Poxon et al. (2000, supra) hypothesized, that a change in the DNA conformation from supercoiled to open circular and linear form would be indicative of damage of the plasmid DNA. However, the percentage of supercoiled DNA did not change after lyophilization and subsequent DMED treatment, suggesting that other effects are responsible for the loss of transfection efficiency. Poxon et al. (2000, supra) found that a decrease in plasmid DNA activity as measured by an in vitro transfection assay can be ameliorated by the use of carbohydrates during lyophilization of the plasmid DNA. Glucose (monosaccharide), sucrose and lactose (disaccharides) were used as lyoprotectants. Poxon et al. (2000, supra), however, only carried out investigations using plasmid DNA.

Although trehalose is a common excipient, which is widely used in freeze drying processes of biomolecules, its beneficial effect on stability of lyophilized nucleic acid molecules could not be foreseen. Moreover, A. del Pozo-Rodriguez et. al. showed that the lyophilization of DNA complexed with solid lipid nanoparticles leads to a drastic decrease in transfection activity over time in the presence of trehalose, while solid lipid nanoparticles alone did not lose their activity after freeze drying. Furthermore, Molina et al (Molina, M. C., S. D. Allison, et al. (2001), J Pharm Sci 90(10): 1445-55) also showed a decrease in activity after storage of freeze dried lipid/DNA complexes formulated in trehalose.

Even though a number of prior art documents suggest the stabilization of nucleic acids during lyophilization in the context of plasmid DNA, only few publications focus on stabilization of other nucleic acids, such as RNAs, e.g. during lyophilization and long-term storage. Furthermore, lyophilization under controlled conditions is rarely described at all.

In this respect, Jones et al (2007, supra) is a rare document, which examines the effect of sugars on long-term stability of mRNA. It describes the possibility of preventing storage dependent loss of in vitro transfection activity. Jones et al (2007, supra) use trehalose as a lyoprotectant and show a positive effect on the transfection activity after storage at a temperature of 4° C. for a period of 6 months. The mRNA integrity was determined via the loss of weight after recovery and via agarose gel electrophoresis. However, at elevated temperatures (room temperature and higher), degradation and a dramatic loss of transfection efficiency were observed. Moreover, the freeze drying process described by Jones et al. requires the freezing of the formulation below −70° C. by immersing in liquid nitrogen. Such a procedure is practically not feasible, especially in a scaled-up process in a regulated environment, wherein controlled conditions are mandatory.

It was further reported that temperature stability of mRNA lyophilized with mannose as lyoprotectant was enhanced in contrast to liquid formulations (WO 2011/069586 A1). However, mannose containing mRNA formulations require a freezing temperature below −47° C. in order to avoid the frozen solution from thawing while drying. The shelf temperature in a state-of-the-art freeze dryer can typically be controlled in a range from −40° C. to +50° C. Temperatures below this level require special equipment and a special cooling medium, e.g. special cooling oil. On the other hand, a fully controlled freeze drying cycle is crucial for the regulated manufacturing of, for instance, pharmaceuticals. As a matter of fact, mannose as a lyoprotectant as described in the prior art is not applicable to a large-scale process, which is carried out in a state-of-the-art freeze dryer in a regulated environment.

Additionally, even though storage at −20° C. or even −80° C. is technically possible, such storage requires an extraordinary effort and involves excessive costs. Such expenses, however, are usually prohibitive for any commercial and sometimes private ventures. This particularly applies to tropical regions or third-world countries, where costs have to be kept low for economic reasons and where energy supply is often limited. Furthermore, it may be required to ship or transport such nucleic acids under circumstances, where not much space (and/or energy) is available for storage, e.g. in cases of a "production to bedside" or even a "bench to bedside" scenario. Such a requirement for safe and cost-effective storage of nucleic acids, in particular of RNA, may also apply to short or long-term expeditions, to long-term storage of nucleic acids in databases, registers or deposit institutions, e.g. databases for biological researchers, governmental or national databases of criminal offenders, etc. Long-term storage capabilities of RNA furthermore opens up a field of various applications and treatments involving RNA as an active substance, e.g. vaccination using RNA, gene therapy using RNA, etc. For the use of RNA, storage at temperatures above 4° C. may therefore entail a valuable economic and logistic advantage in a variety of different situations.

mRNA based vaccines are known to be very instable in aqueous solutions. The shelf life of mRNA in solution is typically only a few days at room temperature. Freeze drying is used to overcome this limitation by reducing or eliminating the water in such a formulation, which results in decreased thermodynamic mobility of the molecules and replacement of the chemically bound water by, for example, hydroxyl groups of cyroprotectives. However, freeze drying conditions are barely predictable and have to be determined for each composition by empirical determination. In particular, if a large-scale production process for pharmaceuticals has to be implemented, the process has to be developed empirically.

Since not only the storage at lower temperatures but also freeze drying itself as part of a production process are energy-intensive, economic aspects are very important when considering freeze drying for industrial application. It is therefore desirable to develop a process, which is cost- and time-efficient.

Standard freeze dryers typically operate at regulated shelf temperatures of −40° C. to +50° C. This is due to the fact that the oil, which is used as a temperature transmission medium in the shelves of the dryers, represents a compromise since it works both as a cooling and as a heating medium. Controllable shelf temperatures below −40° C. could be reached by using specialized oils, which would require, however, other, more sophisticated, technical equipment for the dryer itself. Therefore, industrial freeze drying of products, which have to be frozen below −40° C. before drying, is complicated from a technical point of view and usually not feasible due to the immense cost, which is involved. For many products, the compromise of a technically feasible and economically sound freeze drying process is thus still a challenge.

Even though, freeze drying of RNA under standard laboratory conditions was described, there is still a need for an improved method for RNA lyophilization. In particular, a method is needed that allows industrial application of RNA lyophilization, for example, for the production of a pharmaceutical composition.

Therefore, it is an object of the present invention to provide a method for lyophilization of RNA, which is scalable, reproducible, and applicable for the production of pharmaceuticals and which is time- and cost-efficient. In particular, it is an object of the invention to provide a method for lyophilization of RNA, by which the integrity and the biological activity of the RNA is preferably maintained. It is a further object of the invention to provide a composition comprising RNA, which is suitable for storage also at ambient temperature and over extended periods, and which preferably has increased storage stability as compared to prior art compositions.

The objects underlying the present invention are solved by the claimed subject-matter.

In a first aspect, the present invention provides a method for lyophilizing RNA. In particular, the present invention concerns a method for lyophilizing RNA, wherein the method comprises the following steps:
a) providing a liquid comprising at least one RNA and at least one lyoprotectant;
b) loading the liquid provided into a freeze drying chamber of a freeze dryer;
c) cooling the liquid to a freezing temperature, wherein the cooling is performed at a defined cooling rate;
d) freezing the liquid at the freezing temperature in order to obtain a frozen liquid;
e) reducing the pressure in the freeze drying chamber to a pressure below atmospheric pressure;
f) drying the frozen liquid obtained in step d) in order to obtain a lyophilized composition comprising the at least one RNA and at least one lyoprotectant;
g) equilibrating the pressure in the freeze drying chamber to atmospheric pressure and removing the lyophilized composition comprising the at least one RNA and the at least one lyoprotectant from the freeze drying chamber.

According to a preferred embodiment, steps a) to g) are performed in the order above. However, the inventive method may also be performed by carrying out the steps a) to g) in an alternative order. Moreover, single steps may be performed concomittantly or may overlap.

It has been found by the inventors that lyophilization of RNA in the presence of a lyoprotectant, preferably a carbohydrate lyoprotectant as defined herein, and under controlled conditions, preferably under controlled freezing and/or drying conditions as defined herein, results in a composition comprising RNA, which is characterized by an outstanding integrity of the RNA after completion of the lyophilization process and which is further characterized by increased storage stability, in particular with respect to storage for extended periods and/or under non-cooling conditions. Advantageously, the inventive method is suitable for being used at an industrial scale. The method according to the invention can be used to produce a composition comprising RNA having the above-mentioned properties in a reproducible and cost-effective manner. The composition comprising RNA according to the invention can advantageously be stored, shipped and applied, e.g. in the medical field (for example as a vaccine), without a cold chain, while the integrity and the biological activity of the RNA in the composition remain unexpectedly high. Before the present invention, it was not conceivable that the lyophilization of RNA in the presence of a lyoprotectant would lead to such exceptional properties of the composition according to the invention. Specifically, there was no suggestion in the prior art concerning a method for lyophilizing RNA under controlled conditions, in particular not the controlled freezing and/or drying conditions as defined herein.

In the context of the present invention, the terms 'lyophilization' (also termed cryodesiccation), 'lyophilizing' or 'freeze drying' typically relate to a process, which allows reduction of a solvent (e.g. water) content of a frozen sample (preferably the above defined solution containing at least one RNA and a lyoprotectant as defined herein) in one or more steps via sublimation. In the context of the present invention, lyophilization is typically carried out by freezing a sample in a first step and subsequently drying the sample in one or more steps via sublimation, optionally by reducing the surrounding pressure and/or by heating the sample so that the solvent sublimes directly from the solid phase to the gas phase.

Step a) of the inventive method comprises providing a liquid comprising at least one RNA and at least one lyoprotectant.

In the context of the present invention, the term "RNA" is used as abbreviation for ribonucleic acid. RNA is a nucleic acid molecule, i.e. a polymer consisting of nucleotides. These nucleotides are usually adenosine-monophosphate, uridine-monophosphate, guanosine-monophosphate and cytidine-monophosphate monomers, which are connected to each other along a so-called backbone. The backbone is formed by phosphodiester bonds between the sugar, i.e.

ribose, of a first and a phosphate moiety of a second, adjacent monomer. The specific succession of the monomers is called the RNA sequence. As used herein, the term "RNA molecule" is not limited to any particular type of RNA.

For example, RNA may be obtainable by transcription of a DNA-sequence, e.g., inside a cell. In eukaryotic cells, transcription is typically performed inside the nucleus or the mitochondria. In vivo, transcription of DNA usually results in the so-called premature RNA, which has to be processed into so-called messenger-RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a (mature) mRNA comprises a 5'-cap, optionally a 5'UTR, an open reading frame, optionally a 3'UTR and a poly(A) and/or poly(C) sequence. Furthermore, the term "RNA molecule" comprises ribonucleic acids comprising more than one open reading frame, such as bicistronic or multicistronic RNA molecules. A bicistronic or multicistronic RNA molecule is typically an RNA molecule, preferably an mRNA molecule, that may typically have two (bicistronic) or more (multicistronic) open reading frames (ORF).

Aside from messenger RNA, several non-coding types of RNA exist, which may be involved in regulation of transcription and/or translation, such as a ribosomal RNA (rRNA) or a transfer RNA (tRNA). The terms "RNA" or "RNA molecule" further encompass other coding RNA molecules, such as viral RNA, retroviral RNA, self-replicating RNA (replicon RNA), small interfering RNA (siRNA), microRNA, small nuclear RNA (snRNA), small-hairpin (sh) RNA, riboswitches, ribozymes or aptamers.

Preferably, the at least one RNA is a long-chain RNA. The term long-chain RNA' as used herein herein typically refers to an RNA molecule, preferably as described herein, which preferably comprises at least 30 nucleotides. Alternatively, a long-chain RNA may comprise at least 35, 40, 45, 50, 55, 60, 65, 70, 75, 80, 85, 90, 95, 100, 150, 200, 250, 300, 350, 400, 450 or at least 500 nucleotides. A long-chain RNA molecule may further comprise at least 100 nucleotides, even more preferably at least 200 nucleotides. A long-chain RNA, in the context of the present invention, further preferably comprises from 30 to 50.000 nucleotides, from 30 to 20.000 nucleotides, from 100 to 20.000 nucleotides, from 200 to 20.000 nucleotides, from 200 to 15.000 nucleotides or from 500 to 20.000 nucleotides. The term long-chain RNA' as used herein is not limited to a certain type of RNA, but merely refers to the number of nucleotides comprised in said RNA. In a preferred embodiment, the at least one RNA as used herein is a long-chain mRNA.

The at least one RNA as used herein preferably comprises at least 30 nucleotides. Alternatively, the at least one RNA according to the invention may comprise at least 35, 40, 45, 50, 55, 60, 65, 70, 75, 80, 85, 90, 95, 100, 150, 200, 250, 300, 350, 400, 450 or at least 500 nucleotides. In a preferred embodiment, the at least one RNA comprises at least 100 nucleotides, even more preferably at least 200 nucleotides. The at least one RNA further preferably comprises from 30 to 50.000 nucleotides, from 30 to 20.000 nucleotides, from 100 to 20.000 nucleotides, from 200 to 20.000 nucleotides, from 250 to 15.000 nucleotides or from 500 to 20.000 nucleotides.

In a preferred embodiment, the liquid, which is provided in step a) of the inventive method, comprises at least one RNA and may optionally further comprise a second or further nucleic acid molecule. Preferably, the second or further nucleic acid molecule comprised in the liquid provided in step a) of the inventive method is distinct from the at least one RNA. For instance, the at least one RNA may be an RNA molecule encoding a protein or peptide, while the second or further nucleic acid molecule may be an immunostimulating nucleic acid molecule, preferably as defined herein.

In a preferred embodiment, the at least one RNA comprised in the liquid, which is provided in step a) of the inventive method is not an RNA molecule selected from the group consisting of a small interfering RNA (siRNA), a microRNA, a small nuclear RNA (snRNA), a small-hairpin (sh) RNA or riboswitch, a ribozyme, and an aptamer. In a particularly preferred embodiment, the at least one RNA as used herein is not an siRNA.

According to a preferred embodiment of the invention, the at least one RNA is not a viral RNA or an RNA, which is derived from a viral RNA. In this context, the phrase "viral RNA" comprises any RNA that is derived from a virus, preferably a virus as defined herein. For instance, the phrase "viral RNA" comprises viral genomes (or fragments thereof) as well as transcripts thereof (or fragments of such transcripts). The phrase may be used herein with respect to single-stranded or double-stranded RNAs and with respect to a sense strand (+-strand) as well with respect to an antisense strand (--strand) of a viral RNA. In particular, the phrase "viral RNA" as used herein comprises viral mRNAs. The phrase "an RNA, which is derived from a viral RNA" typically comprises any RNA comprising a nucleic acid sequence, which is derived from a viral RNA, preferably from a viral RNA as defined herein. Preferably, an RNA derived from a viral RNA is a fragment or a variant, preferably a fragment or a variant as defined herein, of the viral RNA.

In some embodiments, the at least one RNA of the present invention is preferably not a viral replicon. More preferably, the at least one RNA of the present invention is not comprised in a viral particle or a viral replicon particle.

In particular, the at least one RNA of the present invention is preferably not an RNA derived from a virus selected from the group of double-stranded (ds) DNA viruses, single-stranded (ss) DNA viruses, dsRNA viruses, (+) ssRNA viruses (sense strand ssRNA viruses), (−) ssRNA viruses (antisense strand ssRNA viruses), ssRNA-RT viruses (retroviruses) and dsDNA-RT viruses (pararetroviruses).

Preferably, the at least one RNA of the present invention is not an RNA derived from a dsDNA virus. More preferably, the at least one RNA of the present invention is not an RNA derived from a virus selected from the group consisting of Myoviridae, Podoviridae, Siphoviridae, Alloherpesviridae, Herpesviridae, Malacoherpesviridae, Lipothrixviridae, Rudiviridae, Adenoviridae, Ampullaviridae, Ascoviridae, Asfarviridae, Baculoviridae, Bicaudaviridae, Clavaviridae, Corticoviridae, Fuselloviridae, Globuloviridae, Guttaviridae, Hytrosaviridae, Iridoviridae, Marseilleviridae, Mimiviridae, Nimaviridae, Pandoraviridae, Papillomaviridae, Phycodnaviridae, Plasmaviridae, Polydnaviruses, Polyomaviridae, Poxviridae, Sphaerolipoviridae, Tectiviridae and Turriviridae.

According to one embodiment of the invention, the at least one RNA of the present invention is not an RNA derived from an ssDNA virus. More preferably, the at least one RNA of the present invention is not an RNA derived from a virus belonging to a virus family selected from the group consisting of Anelloviridae, Bacillariodnaviridae, Bidnaviridae, Circoviridae, Geminiviridae, Inoviridae, Microviridae, Nanoviridae, Parvoviridae and Spiraviridae.

In certain embodiments, the at least one RNA of the present invention is not an RNA derived from a dsRNA virus. More preferably, the at least one RNA of the present invention is not an RNA derived from a virus belonging to a virus family selected from the group consisting of Alternaviridae, Amalgaviridae, Birnaviridae, Chrysoviridae, Cystoviridae, Endornaviridae, Hypoviridae, Partitiviridae, Picobirnaviridae, Reoviridae and Totiviridae.

According to a preferred embodiment, the at least one RNA of the present invention is not an RNA derived from a (+) ssRNA virus. More preferably, the at least one RNA of the present invention is not an RNA derived from a virus belonging to a virus family selected from the group consisting of Arteriviridae, Coronaviridae, Mesoniviridae, Roniviridae, Dicistroviridae, Iflaviridae, Marnaviridae, Picornaviridae, Secoviridae, Alphaflexiviridae, Betaflexiviridae, Gammaflexiviridae, Tymoviridae, Alphatetraviridae, Alvernaviridae, Astroviridae, Barnaviridae, Bromoviridae, Caliciviridae, Carmotetraviridae, Closteroviridae, Flaviviridae, Leviviridae, Luteoviridae, Narnaviridae, Nodaviridae, Permutotetraviridae, Potyviridae, Togaviridae, Tombusviridae and Virgaviridae.

According to one embodiment of the invention, the at least one RNA of the present invention is not an RNA derived from a (−) ssRNA virus. More preferably, the at least one RNA of the present invention is not an RNA derived from a virus belonging to a virus family selected from the group consisting of Bornaviridae, Filoviridae, Paramyxoviridae, Rhabdoviridae, Nyamiviridae, Arenaviridae, Bunyaviridae, Ophioviridae and Orthomyxoviridae.

Preferably, the at least one RNA of the present invention is not an RNA derived from an ssRNA-RT virus (retrovirus). More preferably, the at least one RNA of the present invention is not an RNA derived from a virus belonging to a virus family selected from the group consisting of Metaviridae, Pseudoviridae, and Retroviridae.

In some embodiments, the at least one RNA of the present invention is not an RNA derived from a dsDNA-RT virus (pararetrovirus). More preferably, the at least one RNA of the present invention is not an RNA derived from a virus belonging to the virus family of Hepadnaviridae or to the virus family of Caulimoviridae.

Alternatively, the at least one RNA of the present invention is not an RNA derived from a virus belonging to a virus family selected from the group consisting of Togaviridae, Retroviridae, Adenoviridae and Poxviridae.

According to certain embodiments, the at least one RNA of the present invention is not an RNA derived from an alphavirus, a lentivirus, an adenovirus or a pox virus.

Preferably, the at least one RNA of the present invention is not an RNA derived from an alphavirus. More preferably, the at least one RNA of the present invention is not an RNA derived from Semliki Forest virus (SFV), Sindbis (SIN) virus or Venezuelan equine encephalitis (VEE) virus.

As used herein, the terms "RNA" or "RNA molecule" typically refer to a single-stranded or to a double-stranded RNA molecule. In a preferred embodiment, the at least one RNA of the inventive method is a single-stranded RNA molecule.

In a further embodiment, the at least one RNA comprised in the liquid provided in step a) is a coding RNA molecule or an immunostimulatory RNA molecule, preferably as defined herein.

In the context of the inventive method, the at least one RNA may be a coding RNA molecule encoding a protein or a peptide, which may be selected, without being restricted thereto, e.g. from therapeutically active proteins or peptides, selected e.g. from adjuvant proteins, from antigens, e.g. tumour antigens, pathogenic antigens (e.g. selected, from animal antigens, from viral antigens, from protozoan antigens, from bacterial antigens), allergenic antigens, autoimmune antigens, or further antigens, preferably as defined herein, from allergens, from antibodies, from immunostimulatory proteins or peptides, from antigen-specific T-cell receptors, or from any other protein or peptide suitable for a specific (therapeutic) application, wherein the coding RNA molecule may be transported into a cell, a tissue or an organism and the protein may be expressed subsequently in this cell, tissue or organism. In a particularly preferred embodiment, the at least one RNA provided in the liquid in step a) of the inventive method is an mRNA molecule.

The at least one RNA comprised in the liquid provided in step a) of the inventive method may further be an immunostimulatory RNA molecule, such as any RNA molecule known in the art, which is capable of inducing an immune response, preferably an innate immune response. Such an immunostimulatory RNA may be any (double-stranded or single-stranded) RNA, e.g. a coding RNA, as defined herein. In a preferred embodiment, the immunostimulatory RNA is a non-coding RNA. Preferably, the immunostimulatory RNA may be a single-stranded, a double-stranded or a partially double-stranded RNA, more preferably a single-stranded RNA, and/or a circular or linear RNA, more preferably a linear RNA. More preferably, the immunostimulatory RNA may be a (linear) single-stranded RNA. Even more preferably, the immunostimulatory RNA may be a (long) (linear) single-stranded) non-coding RNA. In this context, it is particularly preferred that the isRNA carries a triphosphate at its 5'-end, which is the case for in vitro transcribed RNA. An immunostimulatory RNA may also occur as a short RNA oligonucleotide, preferably as defined herein.

As used herein, an immunostimulatory RNA may furthermore be selected from any class of RNA molecules, found in nature or being prepared synthetically, and which can induce an innate immune response and may support an adaptive immune response induced by an antigen. In this context, an immune response may occur in various ways. A substantial factor for a suitable (adaptive) immune response is the stimulation of different T-cell sub-populations. T-lymphocytes are typically divided into two sub-populations, the T-helper 1 (Th1) cells and the T-helper 2 (Th2) cells, through which the immune system is capable of destroying intracellular (Th1) and extracellular (Th2) pathogens (e.g. antigens). The two Th cell populations differ in the pattern of the effector proteins (cytokines) produced by them. Thus, Th1 cells assist the cellular immune response by activation of macrophages and cytotoxic T-cells. Th2 cells, on the other hand, promote the humoral immune response by stimulation of B-cells for conversion into plasma cells and by formation of antibodies (e.g. against antigens). The Th1/Th2 ratio is therefore of great importance in the induction and maintenance of an adaptive immune response. In connection with the present invention, the Th1/Th2 ratio of the (adaptive) immune response is preferably shifted in the direction towards the cellular response (Th1 response) and a cellular immune response is thereby induced. According to one example, the innate immune system, which may support an adaptive immune response, may be activated by ligands of Toll-like receptors (TLRs). TLRs are a family of highly conserved pattern recognition receptor (PRR) polypeptides that recognize pathogen-associated molecular patterns (PAMPs) and play a critical role in innate immunity in mammals. Currently at least thirteen family members, designated TLR1-TLR13 (Toll-like receptors: TLR1, TLR2, TLR3, TLR4, TLR5, TLR6, TLR7, TLR8, TLR9, TLR10, TLR11, TLR12 or TLR13), have been identified. Furthermore, a number of specific TLR ligands have been identified. It was found, for instance, that unmethylated bacterial DNA and synthetic analogs thereof (CpG DNA) are ligands for TLR9 (Hemmi H et al. (2000) Nature 408:740-5; Bauer S et al. (2001) Proc Natl Acad Sci USA 98, 9237-42). Furthermore, it has been reported that ligands for certain TLRs include certain nucleic acid molecules and that certain types of RNA are immunostimulatory in a sequence-independent or sequence-dependent manner, wherein these various immunostimulatory RNAs may e.g. stimulate TLR3, TLR7, or TLR8, or intracellular receptors such as RIG-I, MDA-5, etc. E.g. Lipford et al. determined certain G,U-containing oligoribonucleotides as immunostimulatory by acting via TLR7 and TLR8 (see WO 03/086280). The immunostimulatory G,U-containing oligoribonucleotides described by Lipford et al. were believed to be derivable from RNA sources including ribosomal RNA, transfer RNA, messenger RNA, and viral RNA.

The immunostimulatory RNA (isRNA) as used herein may thus comprise any RNA sequence, which enhances an immune response in a host. Preferably, the isRNA used as the at least one RNA comprised in the liquid provided in step a) enhances the immune response, which is preferably an adaptive immune response, which is preferably elicited by a peptide or protein encoded by a second or further nucleic acid molecule, preferably an mRNA, that is administered to the host in combination with the at least one RNA comprised in the liquid provided in step a). The isRNA as used herein may thus comprise any RNA sequence known to be immunostimulatory, including, without being limited thereto, RNA sequences representing and/or encoding ligands of TLRs, preferably selected from human family members TLR1-TLR10 or murine family members TLR1-TLR13, more preferably selected from (human) family members TLR1-TLR10, even more preferably from TLR7 and TLR8, ligands for intracellular receptors for RNA (such as RIG-I or MDA-5, etc.) (see e.g. Meylan, E., Tschopp, J. (2006). Toll-like receptors and RNA helicases: two parallel ways to trigger antiviral responses. Mol. Cell 22, 561-569), or any other immunostimulatory RNA sequence. Furthermore, (classes of) immunostimulatory RNA molecules may include any other RNA capable of eliciting an innate immune response. Without being limited thereto, such an immunostimulatory RNA may include ribosomal RNA (rRNA), transfer RNA (tRNA), messenger RNA (mRNA), and viral RNA (vRNA). Such an immunostimulatory RNA may comprise a length of 1000 to 5000, of 500 to 5000, of 5 to 5000, or of 5 to 1000, 5 to 500, 5 to 250, of 5 to 100, of 5 to 50 or of 5 to 30 nucleotides.

Particularly preferred in this context are immunostimulatory RNA molecules as described in WO 2009/095226.

In a preferred embodiment, the at least one RNA comprised in the liquid provided in step a) of the inventive method comprises at least one modification, preferably a modification as described herein. Alternatively or additionally, the liquid provided in step a) may comprise a second or further RNA molecule (distinct from the at least one RNA molecule), which comprises at least one modification, preferably as described herein. According to a preferred embodiment, the at least one RNA comprised in the liquid provided in step a) of the inventive method comprises an RNA modification, which preferably increases the stability of the at least one RNA and/or the expression of a protein encoded by the at least one RNA. Several RNA modifications are known in the art, which can be applied to an RNA molecule in the context of the present invention.

Chemical Modifications:

The term "RNA modification" as used herein may refer to chemical modifications comprising backbone modifications as well as sugar modifications or base modifications.

In this context, a modified RNA molecule as defined herein may contain nucleotide analogues/modifications, e.g. backbone modifications, sugar modifications or base modifications. A backbone modification in connection with the present invention is a modification, in which phosphates of the backbone of the nucleotides contained in an RNA molecule as defined herein are chemically modified. A sugar modification in connection with the present invention is a chemical modification of the sugar of the nucleotides of the RNA molecule as defined herein. Furthermore, a base modification in connection with the present invention is a chemical modification of the base moiety of the nucleotides of the RNA molecule. In this context, nucleotide analogues or modifications are preferably selected from nucleotide analogues, which are applicable for transcription and/or translation.

Sugar Modifications:

The modified nucleosides and nucleotides, which may be incorporated into a modified RNA molecule as described herein, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O(CH$_2$CH$_2$O)nCH$_2$CH$_2$OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH2; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified RNA molecule can include nucleotides containing, for instance, arabinose as the sugar.

Backbone Modifications:

The phosphate backbone may further be modified in the modified nucleosides and nucleotides, which may be incorporated into a modified RNA molecule as described herein. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications:

The modified nucleosides and nucleotides, which may be incorporated into a modified RNA molecule as described herein can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogues/modifications are selected from base modifications, which are preferably selected from 2-amino-6-chloropurineriboside-5'-triphosphate, 2-aminopurine-riboside-5'-triphosphate; 2-aminoadenosine-5'-triphosphate, 2'-amino-2'-deoxycytidine-triphosphate, 2-thiocytidine-5'-triphosphate, 2-thiouridine-5'-triphosphate, 2'-fluorothymidine-5'-triphosphate, 2'-O-methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-bromo-2'-deoxycytidine-5'-triphosphate, 5-bromo-2'-deoxyuridine-5'-triphosphate, 5-iodocytidine-5'-triphosphate, 5-iodo-2'-deoxycytidine-5'-triphosphate, 5-iodouridine-5'-triphosphate, 5-iodo-2'-deoxyuridine-5'-triphosphate, 5-methylcytidine-5'-triphosphate, 5-methyluridine-5'-triphosphate, 5-propynyl-2'-deoxycytidine-5'-triphosphate, 5-propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group. In specific embodiments, a modified nucleoside is 5'-O-(1-thiophosphate)-adenosine, 5'-O-(1-thiophosphate)-cytidine, 5'-O-(1-thiophosphate)-guanosine, 5'-O-(1-thiophosphate)-uridine or 5'-O-(1-thiophosphate)-pseudouridine.

In further specific embodiments, a modified RNA may comprise nucleoside modifications selected from 6-aza-cytidine, 2-thio-cytidine, a-thio-cytidine, pseudo-iso-cytidine, 5-aminoallyl-uridine, 5-iodo-uridine, N1-methyl-pseudouridine, 5,6-dihydrouridine, a-thio-uridine, 4-thio-uridine, 6-aza-uridine, 5-hydroxy-uridine, deoxy-thymidine, 5-methyl-uridine, pyrrolo-cytidine, inosine, α-thio-guanosine, 6-methyl-guanosine, 5-methyl-cytdne, 8-oxo-guanosine, 7-deaza-guanosine, N1-methyl-adenosine, 2-amino-6-chloro-purine, N6-methyl-2-amino-purine, pseudo-iso-cytidine, 6-chloro-purine, N6-methyl-adenosine, a-thio-adenosine, 8-azido-adenosine, 7-deaza-adenosine.

Lipid Modification:

According to a further embodiment, a modified RNA molecule as defined herein can contain a lipid modification. Such a lipid-modified RNA molecule typically comprises an RNA as defined herein. Such a lipid-modified RNA molecule as defined herein typically further comprises at least one linker covalently linked with that RNA molecule, and at least one lipid covalently linked with the respective linker. Alternatively, the lipid-modified RNA molecule comprises at least one RNA molecule as defined herein and at least one (bifunctional) lipid covalently linked (without a linker) with that RNA molecule. According to a third alternative, the lipid-modified RNA molecule comprises an RNA molecule as defined herein, at least one linker covalently linked with that RNA molecule, and at least one lipid covalently linked with the respective linker, and also at least one (bifunctional)

lipid covalently linked (without a linker) with that RNA molecule. In this context, it is particularly preferred that the lipid modification is present at the terminal ends of a linear RNA sequence.

Modification of the 5'-End of a Modified RNA Molecule:

According to another preferred embodiment of the invention, a modified RNA molecule as defined herein, can be modified by the addition of a so-called "5' CAP" structure.

A 5'-cap is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. m7GpppN is the 5'-CAP structure which naturally occurs in mRNA transcribed by polymerase II and is therefore not considered as modification comprised in a modified RNA in this context. Accordingly, a modified RNA of the present invention may comprise a m7GpppN as 5'-CAP, but additionally the modified RNA comprises at least one further modification as defined herein.

Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-CAP structures are regarded as at least one modification in this context.

Particularly preferred modified 5'-CAP structures are CAP1 (methylation of the ribose of the adjacent nucleotide of m7G), CAP2 (methylation of the ribose of the 2nd nucleotide downstream of the m7G), CAP3 (methylation of the ribose of the 3rd nucleotide downstream of the m7G), CAP4 (methylation of the ribose of the 4th nucleotide downstream of the m7G), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

In a preferred embodiment, the liquid provided in step a) of the inventive method comprises at least one RNA, wherein the RNA is a modified RNA molecule having at least one open reading frame, which encodes at least one peptide or protein. Said modified RNA molecule having at least one open reading frame may be the at least one RNA molecule or a second or further RNA molecule, which may be comprised in the liquid provided in step a) in addition to the first RNA molecule. Preferably, the sequence of the open reading frame in such an RNA molecule is modified as described herein.

Modification of the G/C Content:

In a particularly preferred embodiment of the present invention, the G/C content of the coding region of a modified RNA comprised in the liquid provided in step a), is modified, particularly increased, compared to the G/C content of its respective wild type coding region, i.e. the unmodified coding region. The encoded amino acid sequence of the coding region is preferably not modified compared to the coded amino acid sequence of the respective wild type coding region. The modification of the G/C-content of the coding region of the modified RNA as defined herein is based on the fact that the sequence of any mRNA region to be translated is important for efficient translation of that mRNA. Thus, the composition and the sequence of various nucleotides are important. In particular, mRNA sequences having an increased G (guanosine)/C (cytosine) content are more stable than mRNA sequences having an increased A (adenosine)/U (uracil) content. According to the invention, the codons of the coding region are therefore varied compared to its wild type coding region, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage). Depending on the amino acid to be encoded by the coding region of the modified RNA as defined herein, there are various possibilities for modification of the RNA sequence, e.g. the coding region, compared to its wild type coding region. In the case of amino acids, which are encoded by codons, which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present. In contrast, codons, which contain A and/or U nucleotides, can be modified by substitution of other codons, which code for the same amino acids but contain no A and/or U. Examples of these are: the codons for Pro can be modified from CCU or CCA to CCC or CCG; the codons for Arg can be modified from CGU or CGA or AGA or AGG to CGC or CGG; the codons for Ala can be modified from GCU or GCA to GCC or GCG; the codons for Gly can be modified from GGU or GGA to GGC or GGG. In other cases, although A or U nucleotides cannot be eliminated from the codons, it is however possible to decrease the A and U content by using codons, which contain a lower content of A and/or U nucleotides. Examples of these are: the codons for Phe can be modified from UUU to UUC; the codons for Leu can be modified from UUA, UUG, CUU or CUA to CUC or CUG; the codons for Ser can be modified from UCU or UCA or AGU to UCC, UCG or AGC; the codon for Tyr can be modified from UAU to UAC; the codon for Cys can be modified from UGU to UGC; the codon for His can be modified from CAU to CAC; the codon for Gln can be modified from CAA to CAG; the codons for Ile can be modified from AUU or AUA to AUC; the codons for Thr can be modified from ACU or ACA to ACC or ACG; the codon for Asn can be modified from AAU to AAC; the codon for Lys can be modified from AAA to AAG; the codons for Val can be modified from GUU or GUA to GUC or GUG; the codon for Asp can be modified from GAU to GAC; the codon for Glu can be modified from GAA to GAG; the stop codon UAA can be modified to UAG or UGA. In the case of the codons for Met (AUG) and Trp (UGG), on the other hand, there is no possibility of sequence modification. The substitutions listed above can be used either individually or in any possible combination to increase the G/C content of the coding region of the modified RNA as defined herein, compared, to its particular wild type coding region (i.e. the original sequence). Thus, for example, all codons for Thr occurring in the wild type sequence can be modified to ACC (or ACG).

Preferably, the G/C content of the coding region of the modified RNA as defined herein is increased by at least 7%, more preferably by at least 15%, particularly preferably by at least 20%, compared to the G/C content of the wild type coding region. According to a specific embodiment at least 5%, 10%, 20%, 30%, 40%, 50%, 60%, more preferably at least 70%, even more preferably at least 80% and most preferably at least 90%, 95% or even 100% of the substitutable codons in the coding region encoding at least one peptide or protein, which comprises a pathogenic antigen or a fragment, variant or derivative thereof, are substituted, thereby increasing the G/C content of said coding region. In this context, it is particularly preferable to increase the G/C content of the coding region of the modified RNA as defined herein, to the maximum (i.e. 100% of the substitutable codons), compared to the wild type coding region.

Codon Optimization:

According to the invention, a further preferred modification of the coding region encoding at least one peptide or protein of a modified RNA as defined herein, is based on the finding that the translation efficiency is also determined by a different frequency in the occurrence of tRNAs in cells. Thus, if so-called "rare codons" are present in the coding region of the wild type RNA sequence, to an increased extent, the mRNA is translated to a significantly poorer degree than in the case where codons coding for relatively "frequent" tRNAs are present. In this context, the coding region of the modified RNA is preferably modified compared to the corresponding wild type coding region such that at least one codon of the wild type sequence, which codes for a tRNA which is relatively rare in the cell, is exchanged for a codon, which codes for a tRNA which is relatively frequent in the cell and carries the same amino acid as the relatively rare tRNA. By this modification, the coding region of the modified RNA as defined herein, is modified such that codons, for which frequently occurring tRNAs are available, are inserted. In other words, according to the invention, by this modification all codons of the wild type coding region, which code for a tRNA which is relatively rare in the cell, can in each case be exchanged for a codon, which codes for a tRNA which is relatively frequent in the cell and which, in each case, carries the same amino acid as the relatively rare tRNA. Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content, which is increased, in particular maximized, in the coding region of the modified RNA as defined herein, with the "frequent" codons without modifying the amino acid sequence of the peptide or protein encoded by the coding region of the RNA. This preferred embodiment allows provision of a particularly efficiently translated and stabilized (modified) RNA as defined herein.

In the context of the present invention, the at least one RNA comprised in the liquid provided in step a) may also comprise a 5'- and/or 3' untranslated region (5'-UTR or 3'-UTR, respectively). Preferably, the at least one RNA comprises at least one selected from the group consisting of a 5'-UTR, a 3'-UTR, a poly(A) sequence, a poly(C) sequence and a histone stem-loop sequence. More preferably, the at least one RNA comprises a 5'-CAP structure.

In the context of the present invention, a 3'-UTR is typically the part of an mRNA, which is located between the protein coding region (i.e. the open reading frame) and the 3'-terminus of the mRNA. A 3'-UTR of an mRNA is not translated into an amino acid sequence. The 3'-UTR sequence is generally encoded by the gene, which is transcribed into the respective mRNA during the gene expression process. In the context of the present invention, a 3'-UTR corresponds to the sequence of a mature mRNA, which is located 3' to the stop codon of the protein coding region, preferably immediately 3' to the stop codon of the protein coding region, and which extends to the 5'-side of the 3'-terminus of the mRNA or of the poly(A) sequence, preferably to the nucleotide immediately 5' to the poly(A) sequence. The term "corresponds to" means that the 3'-UTR sequence may be an RNA sequence, such as in the mRNA sequence used for defining the 3'-UTR sequence, or a DNA sequence, which corresponds to such RNA sequence. In the context of the present invention, the term "a 3'-UTR of a gene", such as "a 3'-UTR of an albumin gene", is the sequence, which corresponds to the 3'-UTR of the mature mRNA derived from this gene, i.e. the mRNA obtained by transcription of the gene and maturation of the pre-mature mRNA. The term "3'-UTR of a gene" encompasses the DNA sequence and the RNA sequence of the 3'-UTR. Preferably, the 3'-UTR used according to the present invention is heterologous to the coding region of the mRNA sequence. Even if 3'-UTR's derived from naturally occurring genes are preferred, also synthetically engineered UTR's may be used in the context of the present invention.

As used herein, the term '5'-UTR' typically refers to a particular section of messenger RNA (mRNA). It is located 5' of the open reading frame of the mRNA. Typically, the 5'-UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites or a 5'-Terminal Oligopyrimidine Tract. The 5'-UTR may be posttranscriptionally modified, for example by addition of a 5'-CAP. In the context of the present invention, a 5'-UTR corresponds to the sequence of a mature mRNA, which is located between the 5'-CAP and the start codon. Preferably, the 5'-UTR corresponds to the sequence, which extends from a nucleotide located 3' to the 5'-CAP, preferably from the nucleotide located immediately 3' to the 5'-CAP, to a nucleotide located 5' to the start codon of the protein coding region, preferably to the nucleotide located immediately 5' to the start codon of the protein coding region. The nucleotide located immediately 3' to the 5'-CAP of a mature mRNA typically corresponds to the transcriptional start site. The term "corresponds to" means that the 5'-UTR sequence may be an RNA sequence, such as in the mRNA sequence used for defining the 5'-UTR sequence, or a DNA sequence, which corresponds to such RNA sequence. In the context of the present invention, the term "a 5'-UTR of a gene", such as "a 5'-UTR of a TOP gene", is the sequence, which corresponds to the 5'-UTR of the mature mRNA derived from this gene, i.e. the mRNA obtained by transcription of the gene and maturation of the pre-mature mRNA. The term "5'-UTR of a gene" encompasses the DNA sequence and the RNA sequence of the 5'-UTR. Preferably, the 5'-UTR used according to the present invention is heterologous to the coding region of the mRNA sequence. Even if 5'-UTR's derived from naturally occurring genes are preferred, also synthetically engineered UTR's may be used in the context of the present invention.

In a particularly preferred embodiment, the at least one RNA comprised in the liquid provided in step a) of the inventive method comprises at least one 5'-untranslated region (5'-UTR). More preferably, the at least one RNA comprises a 5'-UTR, which comprises or consists of a nucleic acid sequence, which is derived from a 5'-UTR of a TOP gene, or which is derived from a fragment, homolog or variant of the 5'-UTR of a TOP gene.

The 5'terminal oligopyrimidine tract (TOP) is typically a stretch of pyrimidine nucleotides located at the 5' terminal region of a nucleic acid molecule, such as the 5' terminal region of certain mRNA molecules or the 5' terminal region of a functional entity, e.g. the transcribed region, of certain genes. The sequence starts with a cytidine, which usually corresponds to the transcriptional start site, and is followed by a stretch of usually about 3 to 30 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5' TOP ends one nucleotide 5' to the first purine nucleotide located downstream of the TOP. Messenger RNA that contains a 5'terminal oligopyrimidine tract is often referred to as TOP mRNA. Accordingly, genes that provide such messenger RNAs are referred to as TOP genes. TOP sequences have, for example, been found in genes and mRNAs encoding peptide elongation factors and ribosomal proteins.

In the context of the present invention, a TOP motif is typically a nucleic acid sequence, which corresponds to a 5'TOP as defined above. Thus, a TOP motif in the context of the present invention is preferably a stretch of pyrimidine nucleotides having a length of 3-30 nucleotides. Preferably, the TOP-motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5'end with a cytosine nucleotide. In TOP genes and TOP mRNAs, the TOP-motif preferably starts at its 5'end with the transcriptional start site and ends one nucleotide 5' to the first purine residue in said gene or mRNA. A TOP motif in the sense of the present invention is preferably located at the 5'end of a sequence, which represents a 5'-UTR or at the 5'end of a sequence, which codes for a 5'-UTR. Thus, preferably, a stretch of 3 or more pyrimidine nucleotides is called "TOP motif" in the sense of the present invention if this stretch is located at the 5'end of a respective sequence, such as the inventive mRNA, the 5'-UTR of the inventive mRNA, or the nucleic acid sequence, which is derived from the 5'-UTR of a TOP gene as described herein. In other words, a stretch of 3 or more pyrimidine nucleotides, which is not located at the 5'-end of a 5'-UTR but anywhere within a 5'-UTR is preferably not referred to as "TOP motif".

In this context, a TOP gene is typically characterised by the presence of a 5' terminal oligopyrimidine tract. Furthermore, most TOP genes are characterized by a growth-associated translational regulation. However, also TOP genes with a tissue specific translational regulation are known. As defined above, the 5'-UTR of a TOP gene corresponds to the sequence of a 5'-UTR of a mature mRNA derived from a TOP gene, which preferably extends from the nucleotide located 3' to the 5'-CAP to the nucleotide located 5' to the start codon. A 5'-UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'-UTRs of TOP genes are generally rather short. The lengths of 5'-UTRs of TOP genes may vary between 20 nucleotides up to 500 nucleotides, and are typically less than about 200 nucleotides, preferably less than about 150 nucleotides, more preferably less than about 100 nucleotides. Exemplary 5'-UTRs of TOP genes in the sense of the present invention are the nucleic acid sequences extending from the nucleotide at position 5 to the nucleotide located immediately 5' to the start codon (e.g. the ATG) in the sequences according to SEQ ID Nos. 1-1363, SEQ ID NO. 1395, SEQ ID NO. 1421 and SEQ ID NO. 1422 of the international patent application WO2013/143700 or homologs or variants thereof, whose disclosure is incorporated herewith by reference. In this context, a particularly preferred fragment of a 5'-UTR of a TOP gene is a 5'-UTR of a TOP gene lacking the 5'TOP motif. The term '5'-UTR of a TOP gene' preferably refers to the 5'-UTR of a naturally occurring TOP gene.

In a specific embodiment, the 5'-UTR does not comprise a TOP-motif or a 5'TOP, as defined herein.

In some embodiments, the nucleic acid sequence of the 5'-UTR, which is derived from a 5'-UTR of a TOP gene terminates at its 3'-end with a nucleotide located at position 1, 2, 3, 4, 5, 6, 7, 8, 9 or 10 upstream of the start codon (e.g. A(U/T)G) of the gene or mRNA it is derived from. Thus, the 5'-UTR does not comprise any part of the protein coding region. Thus, preferably, the only protein coding part of the inventive mRNA sequence is provided by the coding region.

The nucleic acid sequence, which is derived from a 5'-UTR of a TOP gene, is preferably derived from a eukaryotic TOP gene, preferably a plant or animal TOP gene, more preferably a chordate TOP gene, even more preferably a vertebrate TOP gene, most preferably a mammalian TOP gene, such as a human TOP gene.

For example, the 5'-UTR preferably comprises or consists of a nucleic acid sequence, which is derived from a nucleic acid sequence selected from the group consisting of SEQ ID Nos. 1-1363, SEQ ID NO. 1395, SEQ ID NO. 1421 and SEQ ID NO. 1422 of the patent application WO2013/143700, whose disclosure is incorporated herein by reference, from the homologs of SEQ ID Nos. 1-1363, SEQ ID NO. 1395, SEQ ID NO. 1421 and SEQ ID NO. 1422 of the patent application WO2013/143700, from a variant thereof, or preferably from a corresponding RNA sequence. The term "homologs of SEQ ID Nos. 1-1363, SEQ ID NO. 1395, SEQ ID NO. 1421 and SEQ ID NO. 1422 of the patent application WO2013/143700" refers to sequences of other species than *Homo sapiens*, which are homologous to the sequences according to SEQ ID Nos. 1-1363, SEQ ID NO. 1395, SEQ ID NO. 1421 and SEQ ID NO. 1422 of the patent application WO2013/143700.

In a preferred embodiment, the 5'-UTR comprises or consists of a nucleic acid sequence, which is derived from a nucleic acid sequence extending from nucleotide position 5 (i.e. the nucleotide that is located at position 5 in the sequence) to the nucleotide position immediately 5' to the start codon (located at the 3' end of the sequences), e.g. the nucleotide position immediately 5' to the ATG sequence, of a nucleic acid sequence selected from SEQ ID Nos. 1-1363, SEQ ID NO. 1395, SEQ ID NO. 1421 and SEQ ID NO. 1422 of the patent application WO2013/143700, from the homologs of SEQ ID Nos. 1-1363, SEQ ID NO. 1395, SEQ ID NO. 1421 and SEQ ID NO. 1422 of the patent application WO2013/143700 from a variant thereof, or a corresponding RNA sequence. It is particularly preferred that the 5' UTR is derived from a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID Nos. 1-1363, SEQ ID NO. 1395, SEQ ID NO. 1421 and SEQ ID NO. 1422 of the patent application WO2013/143700, from the homologs of SEQ ID Nos. 1-1363, SEQ ID NO. 1395, SEQ ID NO. 1421 and SEQ ID NO. 1422 of the patent application WO2013/143700, from a variant thereof, or a corresponding RNA sequence.

In a particularly preferred embodiment, the 5'-UTR comprises or consists of a nucleic acid sequence, which is derived from a 5'-UTR of a ribosomal protein gene, preferably from a 5'-UTR of a TOP gene encoding a ribosomal protein or from a variant of a 5'-UTR of a TOP gene encoding a ribosomal protein. For example, the 5'-UTR comprises or consists of a nucleic acid sequence, which is derived from a 5'-UTR of a nucleic acid sequence according to any of SEQ ID NOs: 67, 170, 193, 244, 259, 554, 650, 675, 700, 721, 913, 1016, 1063, 1120, 1138, and 1284-1360 of the patent application WO2013/143700, a corresponding RNA sequence, a homolog thereof, or a variant thereof as described herein, preferably lacking the 5'TOP motif. As described above, the sequence extending from position 5 to the nucleotide immediately 5' to the ATG (which is located at the 3'end of the sequences) corresponds to the 5'-UTR of said sequences.

Preferably, the 5'-UTR comprises or consists of a nucleic acid sequence, which is derived from a 5'-UTR of a TOP gene encoding a ribosomal Large protein (RPL) or from a homolog or variant of a 5'-UTR of a TOP gene encoding a ribosomal Large protein (RPL). For example, the 5'-UTR comprises or consists of a nucleic acid sequence, which is derived from a 5'-UTR of a nucleic acid sequence according to any of SEQ ID NOs: 67, 259, 1284-1318, 1344, 1346, 1348-1354, 1357, 1358, 1421 and 1422 of the patent application WO2013/143700, a corresponding RNA sequence, a homolog thereof, or a variant thereof as described herein, preferably lacking the 5'TOP motif.

In a particularly preferred embodiment, the 5'-UTR comprises or consists of a nucleic acid sequence, which is derived from the 5'-UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, or from a variant of the 5'-UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, wherein preferably the 5'-UTR does not comprise the 5'TOP of said gene.

A preferred sequence for a 5'-UTR element corresponds to SEQ ID NO. 1368 of the patent application WO2013/143700 and reads as follows:

```
Nucleotide sequence for 5'-UTR element
                                      (SEQ ID NO. 4)
GGCGCTGCCTACGGAGGTGGCAGCCATCTCCTTCTCGGCATC
```

Accordingly, in a particularly preferred embodiment, the 5'-UTR comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO. 1368 of the patent application WO2013/143700 (5'-UTR of human ribosomal protein Large 32 lacking the 5' terminal oligopyrimidine tract, SEQ ID NO. 4) or preferably to a corresponding RNA sequence, or wherein the at least one 5'-UTR comprises or consists of a fragment of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO. 4 or more preferably to a corresponding RNA sequence, wherein, preferably, the fragment is as described above, i.e. being a continuous stretch of nucleotides representing at least 20% etc. of the full-length 5'-UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In some embodiments, the at least one RNA comprises a 5'-UTR, which comprises or consists of a nucleic acid sequence, which is derived from the 5'-UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB, or from a homolog or variant thereof, wherein preferably the 5'-UTR does not comprise a TOP-motif or the 5'TOP of said genes, and wherein optionally the 5'-UTR starts at its 5'-end with a nucleotide located at position 1, 2, 3, 4, 5, 6, 7, 8, 9 or 10 downstream of the 5'terminal oligopyrimidine tract (TOP) and wherein further optionally the 5'-UTR, which is derived from a 5'-UTR of a TOP gene, terminates at its 3'-end with a nucleotide located at position 1, 2, 3, 4, 5, 6, 7, 8, 9 or 10 upstream of the start codon (A(U/T)G) of the gene it is derived from.

In further particularly preferred embodiments, the 5'-UTR comprises or consists of a nucleic acid sequence, which is derived from the 5'-UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgen-induced 1 gene (AIG1), cytochrome c oxidase subunit Vic gene (COX6C), or a N-acylsphingosine amidohydrolase (acid ceramidase) 1 gene (ASAH1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgen-induced 1 gene (AIG1), a vertebrate cytochrome c oxidase subunit Vic gene (COX6C), or a vertebrate N-acyl-sphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cyto-chrome c oxidase subunit Vic gene (COX6C), or a mammalian N-acylsphingosine ami-dohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP syn-thase, H+ transporting, mitochondrial F1 complex, alpha subunit 1, cardiac muscle (ATP5A1) gene, a human hydroxysteroid (17-beta) dehydrogenase 4 gene (HSD17B4), a human androgen-induced 1 gene (AIG1), a human cytochrome c oxidase subunit Vic gene (COX6C), or a human N-acylsphingosine amidohydrolase (acid ceramidase) 1 gene (ASAH1) or from a variant thereof, wherein preferably the 5'-UTR does not comprise the 5'TOP of said gene.

Accordingly, in a particularly preferred embodiment, the 5'-UTR comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO. 1368, or SEQ ID NOs 1412-1420 of the patent application WO2013/143700, or a corresponding RNA sequence, or wherein the at least one 5'-UTR comprises or consists of a fragment of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO. 1368, or SEQ ID NOs 1412-1420 of the patent application WO2013/143700, wherein, preferably, the fragment is as described above, i.e. being a continuous stretch of nucleotides representing at least 20% etc. of the full-length 5'-UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Accordingly, in a particularly preferred embodiment, the 5'-UTR comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according SEQ ID NO. 1414 of the patent application WO2013/143700 (5'-UTR of ATP5A1 lacking the 5' terminal oligopyrimidine tract) or preferably to a corresponding RNA sequence, or wherein the at least one 5'-UTR comprises or consists of a fragment of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO. 1414 of the patent application WO2013/143700or more preferably to a corresponding RNA sequence, wherein, preferably, the fragment is as described above, i.e. being a continuous stretch of nucleotides representing at least 20% etc. of the full-length 5'-UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In a further preferred embodiment, the at least one RNA comprised in the liquid provided in step a) of the inventive method comprises at least one 3'-UTR.

More preferably, the at least one RNA comprises a 3'-UTR, which comprises or consists of a nucleic acid sequence derived from the 3'-UTR of a chordate gene, preferably a vertebrate gene, more preferably a mammalian gene, most preferably a human gene, or from a variant of the 3'-UTR of a chordate gene, preferably a vertebrate gene, more preferably a mammalian gene, most preferably a human gene.

Preferably, the at least one RNA comprises a 3'-UTR, which may be derivable from a gene that relates to an mRNA with an enhanced half-life (that provides a stable mRNA), for example a 3'-UTR as defined and described below.

In a particularly preferred embodiment, the 3'-UTR comprises or consists of a nucleic acid sequence, which is derived from a 3'-UTR of a gene selected from the group consisting of an albumin gene, an a-globin gene, a β-globin gene, a tyrosine hydroxylase gene, a lipoxygenase gene, and a collagen alpha gene, such as a collagen alpha 1(I) gene, or from a variant of a 3'-UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene according to SEQ ID NO. 1369-1390 of the patent application WO2013/143700 whose disclosure is incorporated herein by reference. In a particularly preferred embodiment, the 3'-UTR comprises or consists of a nucleic acid sequence, which is derived from a 3'-UTR of an albumin gene, preferably a vertebrate albumin gene, more preferably a mammalian albumin gene, most preferably a human albumin gene according SEQ ID No: 1369 of the patent application WO2013/143700. The mRNA sequence may comprise or consist of a nucleic acid sequence, which is derived from the 3'-UTR of the human albumin gene according to GenBank Accession number NM_000477.5, or from a fragment or variant thereof.

In this context, it is particularly preferred that the at least one RNA comprises a 3'-UTR comprising a corresponding RNA sequence derived from the nucleic acid sequences according to SEQ ID NO. 1369-1390 of the patent application WO2013/143700 or a fragment, homolog or variant thereof.

Most preferably the 3'-UTR comprises the nucleic acid sequence derived from a fragment of the human albumin gene according to SEQ ID No: 1376 of the patent application WO2013/143700, in the following referred to as SEQ ID NO. 5.

```
Nucleotide sequence of 3'-UTR element of human
albumin gene
                                        (SEQ ID NO. 5)
CATCACATTTAAAAGCATCTCAGCCTACCATGAGAATAAGAGAAAGAAAA

TGAAGATCAATAGCTTATTCATCTCTTTTTCTTTTTCGTTGGTGTAAAGC

CAACACCCTGTCTAAAAAACATAAATTTCTTTAATCATTTTGCCTCTTTT

CTCTGTGCTTCAATTAATAAAAAATGGAAAGAACCT
```

In another particularly preferred embodiment, the 3'-UTR comprises or consists of a nucleic acid sequence, which is derived from a 3'-UTR of an α-globin gene, preferably a vertebrate α- or β-globin gene, more preferably a mammalian α- or β-globin gene, most preferably a human α- or β-globin gene according to SEQ ID NO. 1370 of the patent application WO2013/143700 (3'-UTR of Homo sapiens hemoglobin, alpha 1 (HBA1)), or according to SEQ ID NO. 1371 of the patent application WO2013/143700 (3'-UTR of Homo sapiens hemoglobin, alpha 2 (HBA2)), or according to SEQ ID NO. 1372 of the patent application WO2013/143700 (3'-UTR of Homo sapiens hemoglobin, beta (HBB)).

For example, the 3'-UTR may comprise or consist of the center, α-complex-binding portion of the 3'-UTR of an a-globin gene, such as of a human α-globin gene, preferably according to SEQ ID NO. 6 (corresponding to SEQ ID NO. 1393 of the patent application WO2013/143700).

```
Nucleotide sequence of 3' UTR element of an
α-globin gene
                                        (SEQ ID NO. 6)
GCCCGATGGGCCTCCCAACGGGCCCTCCTCCCCTCCTTGCACCG
```

In this context, it is particularly preferred that the 3'-UTR of the at least one RNA comprises or consists of a corresponding RNA sequence of the nucleic acid sequence according to the above, or a homolog, a fragment or variant thereof.

The term 'a nucleic acid sequence, which is derived from the 3'-UTR of a [ . . . ] gene' preferably refers to a nucleic acid sequence, which is based on the 3'-UTR sequence of a [ . . . ] gene or on a part thereof, such as on the 3'-UTR of an albumin gene, an a-globin gene, a β-globin gene, a tyrosine hydroxylase gene, a lipoxygenase gene, or a collagen alpha gene, such as a collagen alpha 1(I) gene, preferably of an albumin gene or on a part thereof. This term includes sequences corresponding to the entire 3'-UTR sequence, i.e. the full length 3'-UTR sequence of a gene, and sequences corresponding to a fragment of the 3'-UTR sequence of a gene, such as an albumin gene, α-globin gene, β-globin gene, tyrosine hydroxylase gene, lipoxygenase gene, or collagen alpha gene, such as a collagen alpha 1(I) gene, preferably of an albumin gene.

The term 'a nucleic acid sequence, which is derived from a variant of the 3'-UTR of a [ . . . ] gene' preferably refers to a nucleic acid sequence, which is based on a variant of the 3'-UTR sequence of a gene, such as on a variant of the 3'-UTR of an albumin gene, an α-globin gene, a β-globin gene, a tyrosine hydroxylase gene, a lipoxygenase gene, or a collagen alpha gene, such as collagen alpha 1(I) gene, or on a part thereof as described above. This term includes sequences corresponding to the entire sequence of the variant of the 3'-UTR of a gene, i.e. the full length variant 3'-UTR sequence of a gene, and sequences corresponding to a fragment of the variant 3'-UTR sequence of a gene. A fragment in this context preferably consists of a continuous stretch of nucleotides corresponding to a continuous stretch of nucleotides in the full-length variant 3'-UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 3'-UTR. Such a fragment of a variant, in the sense of the present invention, is preferably a functional fragment of a variant as described herein.

Preferably, the at least one 5'-UTR and the at least one 3'-UTR act synergistically to increase protein production from the at least one RNA comprised in the liquid provided in step a) of the inventive method.

In a particularly preferred embodiment, the at least one RNA comprised in the liquid provided in step a) of the inventive method comprises a histone stem-loop sequence/structure. Such histone stem-loop sequences are preferably selected from histone stem-loop sequences as disclosed in WO 2012/019780, whose disclosure is incorporated herewith by reference.

A histone stem-loop sequence, suitable to be used within the present invention, is preferably selected from at least one of the following formulae (I) or (II):

formula (I) (stem-loop sequence without stem bordering elements):

$$\underbrace{[N_{0\text{-}2}GN_{3\text{-}5}]}_{\text{stem1}}\underbrace{[N_{0\text{-}4}(U/T)N_{0\text{-}4}]}_{\text{loop}}\underbrace{[N_{3\text{-}5}CN_{0\text{-}2}]}_{\text{stem2}}$$

formula (II) (stem-loop sequence with stem bordering elements):

$$\underbrace{N_{1\text{-}6}}_{\substack{\text{stem1}\\\text{bordering element}}}\underbrace{[N_{0\text{-}2}GN_{3\text{-}5}]}_{\text{stem1}}\underbrace{[N_{0\text{-}4}(U/T)N_{0\text{-}4}]}_{\text{loop}}\underbrace{[N_{3\text{-}5}CN_{0\text{-}2}]}_{\text{stem2}}\underbrace{N_{1\text{-}6}}_{\substack{\text{stem2}\\\text{bordering element}}}$$

wherein:
stem1 or stem2 bordering elements $N_{1\text{-}6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;
stem1 $[N_{0\text{-}2}GN_{3\text{-}5}]$ is reverse complementary or partially reverse complementary with element stem2, and is a consecutive sequence between of 5 to 7 nucleotides;
  wherein $N_{0\text{-}2}$ is a consecutive sequence of 0 to 2, preferably of 0 to 1, more preferably of 1 N, wherein each N is independently from another selected from a nucleotide selected from A, U, T, G and C or a nucleotide analogue thereof;
  wherein $N_{3\text{-}5}$ is a consecutive sequence of 3 to 5, preferably of 4 to 5, more preferably of 4 N, wherein each N is independently from another selected from a nucleotide selected from A, U, T, G and C or a nucleotide analogue thereof, and
  wherein G is guanosine or an analogue thereof, and may be optionally replaced by a cytidine or an analogue thereof, provided that its complementary nucleotide cytidine in stem2 is replaced by guanosine;
loop sequence $[N_{0\text{-}4}(U/T)N_{0\text{-}4}]$ is located between elements stem1 and stem2, and is a consecutive sequence of 3 to 5 nucleotides, more preferably of 4 nucleotides;

wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and
wherein U/T represents uridine, or optionally thymidine;
stem2 $[N_{3-5}CN_{0-2}]$ is reverse complementary or partially reverse complementary with element stem1, and is a consecutive sequence between of 5 to 7 nucleotides;
wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;
wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and
wherein C is cytidine or an analogue thereof, and may be optionally replaced by a guanosine or an analogue thereof provided that its complementary nucleoside guanosine in stem1 is replaced by cytidine;
wherein
stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one ore more bases in one stem do not have a complementary base in the reverse complementary sequence of the other stem.

According to a further preferred embodiment of the first inventive aspect, the nucleic acid molecule of the inventive polymeric carrier cargo complex as defined herein and/or the second nucleic acid molecule administered in combination with the polymeric carrier cargo complex may comprise at least one histone stem-loop sequence according to at least one of the following specific formulae (Ia) or (IIa):

formula (Ia) (stem-loop sequence without stem bordering elements):

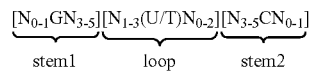

stem1　　loop　　stem2 formula (IIa) (stem-loop sequence with stem bordering elements):

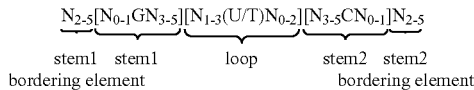

stem1　stem1　　loop　　stem2　stem2
bordering element　　　　　　bordering element wherein:
N, C, G, T and U are as defined above.

According to a further more particularly preferred embodiment of the first aspect, the nucleic acid molecule of the inventive polymeric carrier cargo complex as defined herein and/or the second nucleic acid molecule administered in combination with the polymeric carrier cargo complex may comprise at least one histone stem-loop sequence according to at least one of the following specific formulae (Ib) or (IIb):

formula (Ib) (stem-loop sequence without stem bordering elements):

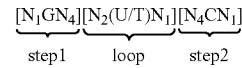

step1　　loop　　step2 formula (IIb) (stem-loop sequence with stem bordering elements):

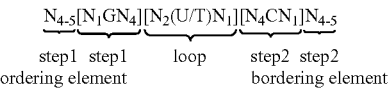

step1　step1　　loop　　step2　step2
bordering element　　　　　　bordering element wherein:
N, C, G, T and U are as defined above.

A particular preferred histone stem-loop sequence is the nucleic acid sequence according to SEQ ID NO. 7.

```
Histone stem-loop nucleotide sequence
                                    (SEQ ID NO. 7)
CAAAGGCTCTTTTCAGAGCCACCA
```

More preferably the stem-loop sequence is the corresponding RNA sequence of the nucleic acid sequence according to SEQ ID NO. 8.

```
Histone stem-loop RNA sequence
                                    (SEQ ID NO. 8)
CAAAGGCUCUUUUCAGAGCCACCA
```

In a preferred embodiment, the at least one RNA comprised in the liquid provided in step a) of the inventive method further comprises a poly(A) sequence. The length of the poly(A) sequence may vary. For example, the poly(A) sequence may have a length of about 20 adenine nucleotides up to about 300 adenine nucleotides, preferably of about 40 to about 200 adenine nucleotides, more preferably from about 50 to about 100 adenine nucleotides, such as about 60, 70, 80, 90 or 100 adenine nucleotides. Most preferably, the at least one RNA comprises a poly(A) sequence of about 60 to about 70 nucleotides, most preferably 64 adenine nucleotides.

Preferably, the poly(A) sequence in the at least one RNA is derived from a DNA template by in vitro transcription. Alternatively, the poly(A) sequence may also be obtained in vitro by common methods of chemical-synthesis without being necessarily transcribed from a DNA-progenitor.

Alternatively, the at least one RNA optionally comprises a polyadenylation signal, which is defined herein as a signal, which conveys polyadenylation to a (transcribed) mRNA by specific protein factors (e.g. cleavage and polyadenylation specificity factor (CPSF), cleavage stimulation factor (CstF), cleavage factors I and II (CF I and CF II), poly(A) polymerase (PAP)). In this context, a consensus polyadenylation signal is preferred comprising the NN(U/T)ANA consensus sequence. In a particularly preferred aspect, the polyadenylation signal comprises one of the following sequences: AA(U/T)AAA or A(U/T)(U/T)AAA (wherein uridine is usually present in RNA and thymidine is usually present in DNA).

In addition or as an alternative to a poly(A) sequence as described above, the at least one RNA may also comprise a poly(C) sequence, preferably in the region 3' of the coding region of the RNA. A poly(C) sequence is typically a stretch of multiple cytosine nucleotides, typically about 10 to about 200 cytidine nucleotides, preferably about 10 to about 100 cytidine nucleotides, more preferably about 10 to about 70 cytidine nucleotides or even more preferably about 20 to about 50 or even about 20 to about 30 cytidine nucleotides. A poly(C) sequence may preferably be located 3' of the coding region comprised by a nucleic acid. In a preferred embodiment of the present invention, the at least one RNA comprises a poly(A) sequence and a poly(C) sequence, wherein the poly(C) sequence is located 3' of the poly(A) sequence.

In a particularly preferred embodiment, the at least one RNA comprised in the liquid provided in step a) of the inventive method comprises a nucleic acid sequence derived from a 5'-TOP-UTR, a GC-optimized coding sequence, a nucleic acid sequence derived from the 3'-UTR of an albumin gene, a poly(A)-sequence, a poly(C)-sequence, and a histone stem loop, preferably in that order from 5' to 3'.

The liquid provided in step a) of the inventive method may comprise the at least one RNA as described herein in free form ("naked RNA") or in the form of a complex with another compound, such as a transfection or complexation agent. For example, the at least one RNA may be present in the liquid provided in step a) of the inventive method in a complex with a cationic or polycationic carrier or compound, which may serve as transfection or complexation agent. In a preferred embodiment, the liquid provided in step a) of the inventive method comprises both, the at least one RNA in free form as well in a complex with a cationic or polycationic carrier or compound. Such a complex of the at least one RNA with a cationic or polycationic carrier or compound may be present in liquid provided in step a) of the inventive method as a nanoparticle. The preparation of RNA complexes with polycationic or cationic compounds is known in the art and is preferably carried out as described in EP1083232, WO2009/030481, WO2010/037539, WO2011/026641, WO2012/013326, or WO2012/113513 the entire disclosure of which is herewith incorporated by reference.

In this context, the at least one RNA comprised in the liquid provided in step a) is preferably complexed by a compound selected from the group of polymers or complexing agents, typically comprising, without being limited thereto, any polymer suitable for the preparation of a pharmaceutical composition, such as minor/major groove binders, nucleic acid binding proteins, lipoplexes, nanoplexes, non-cationic or non-polycationic compounds, such as PLGA, Polyacetate, Polyacrylate, PVA, Dextran, hydroxymethylcellulose, starch, MMP, PVP, heparin, pectin, hyaluronic acid, and derivatives thereof, or cationic or polycationic compound, particularly cationic or polycationic polymers or cationic or polycationic lipids, preferably a cationic or polycationic polymers. In the context of the present invention, such a cationic or polycationic compound is typically selected from any cationic or polycationic compound, suitable for complexing and thereby stabilizing an RNA as defined herein, e.g. by associating the at least one RNA with the cationic or polycationic compound.

Particularly preferred complexation agents in this context are cationic or polycationic compounds, including protamine, nucleoline, spermine or spermidine, or other cationic peptides or proteins, such as poly-L-lysine (PLL), poly-arginine, oligoarginines as defined above, such as $Arg_7$, $Arg_8$, $Arg_9$, $Arg_7$, $H_3R_9$, $R_9H_3$, $H_3R_9H_3$, $YSSR_9SSY$, $(RKH)_4$, $Y(RKH)_2R$, etc., basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, proline-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, pIsl, FGF, Lactoferrin, Transportan, Buforin-2, Bac715-24, SynB, SynB(1), pVEC, hCT-derived peptides, SAP, or histones. In a particularly preferred embodiment, the liquid provided in step a) comprises protamin, wherein the at least one RNA is preferably complexed by protamine.

In a preferred embodiment, the liquid provided in step a) of the inventive method also comprises at least one cationic or polycationic compound, preferably a cationic or polycationic peptide or protein, preferably as defined herein. In a particularly preferred embodiment, the liquid provided in step a) comprises at least one RNA and at least one cationic or polycationic compound, preferably as defined herein, wherein the at least one RNA and the at least one cationic or polycationic compound are present in a complex.

The liquid provided in step a) of the inventive method preferably comprises a cationic or polycationic compound in solution and/or in complex with the at least one RNA. More preferably, the liquid provided in step a) comprises a cationic or polycationic compound, preferably protamine, and the at least one RNA at a weight ratio (RNA:protamine, w/w) in a range from 1:10 to 10:1, more preferably from 5:1 to 1:1, even more preferably from 3:1 to 1:1. Most preferably, the weight ratio of the at least one RNA to cationic or polycationic compound, preferably protamine, in the composition is 2:1 (w/w).

Furthermore, such cationic or polycationic compounds or carriers may be cationic or polycationic peptides or proteins, which preferably comprise or are additionally modified to comprise at least one—SH moiety. Preferably, a cationic or polycationic carrier is selected from cationic peptides having the following sum formula (III):

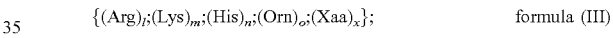
$$\{(Arg)_l;(Lys)_m;(His)_n;(Orn)_o;(Xaa)_x\}; \quad \text{formula (III)}$$

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context, cationic peptides or proteins in the range of 7-30 amino acids are particular preferred.

Further, the cationic or polycationic peptide or protein, when defined according to formula $\{(Arg)_l;(Lys)_m;(His)_n;(Orn)_n;(Xaa)_x\}$ (formula (III)) as shown above and which comprise or are additionally modified to comprise at least one—SH moiety, may be, without being restricted thereto, selected from subformula (IIIa):

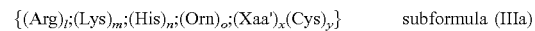
$$\{(Arg)_l;(Lys)_m;(His)_n;(Orn)_o;(Xaa')_x(Cys)_y\} \quad \text{subformula (IIIa)}$$

wherein $(Arg)_l;(Lys)_m;(His)_n;(Orn)_o$; and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide. Further, the cationic or polycationic peptide may be selected from subformula (IIIb):

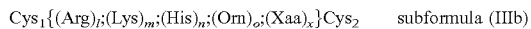

$\text{Cys}_1\{(\text{Arg})_l;(\text{Lys})_m;(\text{His})_n;(\text{Orn})_o;(\text{Xaa})_x\}\text{Cys}_2$   subformula (IIIb)

wherein empirical formula $\{(\text{Arg})_l;(\text{Lys})_m;(\text{His})_n;(\text{Orn})_o;(\text{Xaa})x\}$ (formula (III)) is as defined herein and forms a core of an amino acid sequence and wherein $\text{Cys}_1$ and $\text{Cys}_2$ are Cysteines proximal to, or terminal to $(\text{Arg})_l;(\text{Lys})_m;(\text{His})_n;(\text{Orn})_o;(\text{Xaa})_x$.

Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl) diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]-trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silane backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

In this context, it is particularly preferred that the at least one RNA comprised in the liquid provided in step a) of the inventive method is complexed at least partially with a cationic or polycationic compound, preferably a cationic protein or peptide. Partially means that only a part of the at least one RNA molecule is complexed with a cationic or polycationic compound and that the rest of the at least one RNA molecule is in uncomplexed form ("free"). Preferably the ratio of complexed RNA to free RNA is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed RNA molecule to free RNA molecule is selected from a ratio of about 1:1 (w/w).

In the context of the present invention, the liquid provided in step a) of the inventive method may thus comprise the at least one RNA in free form or complexed by a cationic or polycationic compound. In a preferred embodiment, the liquid comprises a complex, wherein the complex comprises or consists of the at least one RNA complexed by a cationic or polycationic compound, wherein the complex is preferably present as a nanoparticle as defined herein. As used herein, the term "nanoparticle" typically refers to a complex of the at least one RNA molecule with a complexation agent as defined herein, preferably with a cationic or polycationic compound.

In a preferred embodiment, the liquid provided in step a) comprises the at least one RNA in the form of a nanoparticle comprising or consisting of the at least one RNA complexed by a cationic or polycationic compound, wherein the size, preferably the average size, of the nanoparticle is preferably in a range from 50 to 500 nm, more preferably from 50 to 200 nm. In a particularly preferred embodiment, the (average) size of the nanoparticle comprising or consisting of complexed RNA is from 50 to 180 nm, more preferably from 50 to 150 nm.

In a preferred embodiment, the liquid provided in step a) of the inventive method comprises a suitable solvent. Preferably, the liquid comprises a solvent, which allows dissolution of the at least one RNA and, further components, such as a lyoprotectant or a cationic or polycationic compound as defined herein. More preferably, the solvent is volatile with a boiling point of preferably below 150° C. In addition, the solvent is preferably non-toxic. Preferably, the solvent is an aqueous solution. In the case of an organic solvent, the solvent is preferably miscible with water.

In a preferred embodiment, the liquid comprises a solvent comprising an aqueous solution or water, preferably pyrogen-free water or water for injection (WFI). In this context, the term "water for injection" (WFI) is a term defined by standard USP 23. USP 23 monograph states that "Water for Injection (WFI) is water purified by distillation or reverse osmosis." WFI is typically produced by either distillation or 2-stage reverse osmosis. WFI typically does not contain more than 0.25 USP endotoxin units (EU) per ml. Endotoxins are a class of pyrogens that are components of the cell wall of Gram-negative bacteria (the most common type of bacteria in water), preferably in an action limit of 10 cfu/100 ml. The microbial quality may be tested by membrane filtration of a 100 ml sample and plate count agar at an incubation temperature of 30 to 35 degrees Celsius for a 48-hour period. The chemical purity requirements of WFI are typically the same as of PW (purified water).

The liquid provided in step a) of the inventive method may comprise a buffer, preferably selected from a buffer as defined herein, e.g. a buffer containing 2-hydroxypropanoic acid, preferably including at least one of its optical isomers L-(+)-lactic acid, (S)-lactic acid, D-(−)-lactic acid or (R)-lactic acid, more preferably its biologically active optical isomer L-(+)-lactic acid, or a salt or an anion thereof, preferably selected from sodium-lactate, potassium-lactate, or $Al^{3+}$-lactate, $NH_4^+$-lactate, Fe-lactate, Li-lactate, Mg-lactate, Ca-lactate, Mn-lactate or Ag-lactate, or a buffer selected from Ringer's lactate (RiLa), lactated Ringer's solution (main content sodium lactate, also termed "Hartmann's Solution" in the UK), acetated Ringer's solution, or ortho-lactate-containing solutions (e.g. for injection purposes), or lactate containing water. A buffer as defined herein may also be a mannose containing buffer, an isotonic buffer or solution, preferably selected from isotonic saline, a lactate or ortho-lactate-containing isotonic solution, an isotonic buffer or solution selected from phosphate-buffered saline (PBS), TRIS-buffered saline (TBS), Hank's balanced salt solution (HBSS), Earle's balanced salt solution (EBSS), standard saline citrate (SSC), HEPES-buffered saline (HBS), Grey's balanced salt solution (GBSS), or normal saline (NaCl), hypotonic (saline) solutions with addition of glucose or dextrose, or any solution as defined herein, etc. These isotonic buffers or solutions are preferably prepared as defined herein or according to protocols well known in the art for these specific isotonic buffers or solutions. In this context, a buffer may be comprised in the liquid provided in step a) of the inventive method, more preferably an aqueous (isotonic solution or aqueous) buffer, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Typically, the salts are present in such a buffer in a concentration of at least 50 mM sodium chloride (NaCl), at least 3 mM potassium chloride (KCl) and at least 0.01 mM calcium chloride ($CaCl_2$). Furthermore, organic anions of the aforementioned cations may be contained in the buffer. According to a more preferred embodiment, the buffer may contain salts selected from sodium chloride (NaCl), calcium chloride ($CaCl_2$) and optionally potassium chloride (KCl), wherein further anions may be present in addition to the chlorides. $CaCl_2$ may also be replaced therein by another salt like KCl.

In a preferred embodiment, the liquid provided in step a) of the inventive method does not comprise a lipid compound.

According to the present invention, the liquid provided in step a) of the method also comprises at least one lyoprotectant.

As used herein, the term 'lyoprotectant' typically refers to an excipient, which partially or totally replaces the hydration sphere around a molecule and thus prevents catalytic and/or hydrolytic processes.

In a preferred embodiment, the liquid provided in step a) comprises at least one lyoprotectant, wherein the lyoprotectant is selected from the group of (free) carbohydrates. Such group of (free) carbohydrates may comprise, without being limited thereto, any (free) carbohydrate, suitable for the preparation of a pharmaceutical composition, preferably, without being limited thereto, (free) monosaccharides, such as e.g. (free) glucose, (free) fructose, (free) galactose, (free) sorbose, (free) mannose ("free" preferably means unbound or unconjugated, e.g. the mannose is not covalently bound to the at least one RNA, or in other words, the mannose is unconjugated, preferably with respect to the at least one RNA), etc., and mixtures thereof; disaccharides, such as e.g. lactose, maltose, sucrose, trehalose, cellobiose, etc., and mixtures thereof; polysaccharides, such as raffinose, melezitose, maltodextrins, dextrans, dextrins, cellulose, starches, etc., and mixtures thereof; and alditols, such as glycerol, mannitol, xylitol, maltitol, lactitol, xylitol sorbitol, pyranosyl sorbitol, myoinositol, etc., and mixtures thereof. Examples of sugars that are preferably comprised in the liquid provided in step a) include lactose, mannose, mannitol, sucrose or trehalose. Generally, a sugar that is preferred in this context, has a high water displacement activity and a high glass transition temperature. Furthermore, a sugar suitable for use in the liquid provided in step a) is preferably hydrophilic but not hygroscopic. In addition, the sugar preferably has a low tendency to crystallize, such as trehalose. A lyoprotectant in the liquid provided in step a) of the inventive method is preferably selected from the group consisting of mannitol, sucrose, glucose, mannose and trehalose. Trehalose is particularly preferred as a lyoprotectant in the liquid provided in step a).

Furthermore any of the below defined further components may be used as lyoprotectant. Particularly alcohols such as PEG, mannitol, sorbitol, cyclodextran, DMSO, amino acids and proteins such as prolin, glycine, phenylanaline, arginine, serine, albumin and gelatine may be used as lyoprotectant. Additionally metal ions, surfactants and salts as defined below may be used as lyoprotectant. Furthermore polymers may be used as lyoprotectant, particularly polyvinylpyrrolidone.

The weight ratio of the at least one RNA in the liquid provided in step a) to the lyoprotectant, preferably a carbohydrate, more preferably a sugar, even more preferably trehalose, in said liquid is preferably in a range from about 1:2000 to about 1:10, more preferably from about 1:1000 to about 1:100. Most preferably, the weight ratio of the at least one RNA in the liquid provided in step a) to the lyoprotectant, preferably a carbohydrate, more preferably a sugar, even more preferably trehalose, in said liquid is in a range from about 1:250 to about 1:10 and more preferably in a range from about 1:100 to about 1:10 and most preferably in a range from about 1:100 to about 1:50.

In preferred embodiment, the liquid provided in step a) of the inventive method comprises at least 0.01% (w/w), preferably at least 0.1% (w/w), at least 0.5% (w/w), at least 1% (w/w), at least 2.5% (w/w), at least 5% (w/w), at least 10% (w/w), or at least 15% (w/w) of a lyoprotectant, wherein the lyoprotectant is preferably a carbohydrate component, more preferably a sugar, even more preferably trehalose. Further preferably, the liquid provided in step a) of the inventive method comprises a lyoprotectant, preferably a carbohydrate, more preferably a sugar, even more preferably trehalose, at a concentration in a range from 0.1 to 40% (w/w), more preferably at a concentration in a range from 1 to 20% (w/w), more preferably of between 5 to 20% (w/w), even more preferably of between 2.5 to 10% (w/w) and most preferably at a concentration of 5% (w/w).

In one embodiment, the liquid provided in step a) of the inventive method comprises at least one RNA at a concentration of at least 0.01 g/l, preferably at least 0.1 g/l, at least 0.2 g/l, at least 0.3 g/l, at least 0.4 g/l, at least 0.5 g/l, at least 0.6 g/l, at least 0.7 g/l, at least 0.8 g/l, at least 0.9 g/l, at least 1 g/l, at least 2 g/l, at least 3 g/l, at least 4 g/l, or at least 5 g/I. Further preferably, the concentration of the at least one RNA in the liquid is in a range from 0.01 g/l to 50 g/l, more preferably from 0.1 g/l to 10 g/l, even more preferably from 0.2 g/l to 5 g/l, most preferably from 0.5 g/l and 1 g/l (e.g. 0.8 g/l).

The liquid provided in step a) of the inventive method may further comprise any type of suitable component, which is compatible with the at least one RNA. As used herein, the term 'component' preferably comprises any additive or excipient, preferably a pharmaceutically acceptable excipient that does preferably not cause or enhance degradation of the at least one RNA. Such a component may further be in any state, such as liquid, gel-like, solid or semi-solid. A component is preferably selected from the group consisting of cryoprotectants, bulking agents, preservatives, antioxidants, antimicrobial agents, colorants, carriers, fillers, film formers, redispersants and disintegrants. Moreover, the liquid provided in step a) may also comprise excipients, such as defoamers, surfactants, viscosity enhancing agents, force control agents or the like.

Preferably, the liquid provided in step a) comprises at least one component selected from a cryoprotectant or a bulking agent. In this context, cryoprotectants are understood as excipients, which allow influencing the structure of a frozen material and/or the eutectical temperature of the mixture. A bulking agent (e.g. a filler) is any excipient compatible with the at least one RNA, which is comprised in the liquid provided in step a). As used herein, a bulking agent may be used for increasing the volume and/or the mass of the resulting composition. In addition, a bulking agent may also protect the at least one RNA from degradation.

As a further component, the liquid provided in step a) of the inventive method may additionally contain at least one component selected, e.g., from proteins, amino acids, alcohols, mannit, metals or metal ions, surfactants, polymers or complexing agents, buffers, etc., or a combination thereof.

In the context of the present invention, one preferred component may be selected from the group of amino acids. Such group may comprise, without being limited thereto, any naturally occurring amino acid, including alanine, cysteine, aspartic acid, glutamic acid, phenylalanine, glycine, histidine, isoleucine, lysine, leucine, methionine, asparagine, pyrrolysine, proline, glutamine, arginine, serine, threonine, selenocysteine, valine, tryptophan, and tyrosine, more preferably glycine, arginine, and alanine. Cryoprotectants and/or lyoprotectants selected from the group of amino acids may additionally comprise any modification of a naturally occurring amino acid as defined above.

Furthermore, in the context of the present invention, a further component may be selected from the group of alcohols. Such group may comprise, without being limited thereto, any alcohol suitable for the preparation of a pharmaceutical composition, preferably, without being limited thereto, mannitol, polyethyleneglycol, polypropyleneglycol, sorbitol, etc.

In the context of the present invention, a further suitable component may also be selected from the group of proteins. Such group may comprise, without being limited thereto, proteins such as albumin, gelatine, therapeutically active proteins, antibodies, antigens, or any further protein as defined herein.

A preferred component, which may be contained in liquid provided in step a) of the inventive method, may be selected from the group of metals or metal ions, typically comprising, without being limited thereto, metals or metal ions or salts selected from alkali metals, including members of group 1 of the periodic table: lithium (Li), sodium (Na), potassium (K), rubidium (Rb), caesium (Cs), and francium (Fr), and their (monovalent) metal alkali metal ions and salts; preferably lithium (Li), sodium (Na), potassium (K), and their (monovalent) metal alkali metal ions and salts;

alkaline earth metals, including members of group 2 of the periodic table: beryllium (Be), magnesium (Mg), calcium (Ca), strontium (Sr), barium (Ba) and radium (Ra), and their (divalent) alkaline earth metal ions and salts; preferably magnesium (Mg), calcium (Ca), strontium (Sr), barium (Ba) and their (divalent) alkaline earth metal ions and salts;

transition metals, including members of groups 3 to 13 of the periodic table and their metal ions and salts. The transition metals typically comprise the 40 chemical elements 21 to 30, 39 to 48, 71 to 80, and 103 to 112. The name transition originates from their position in the periodic table of elements. In each of the four periods in which they occur, these elements represent the successive addition of electrons to the d atomic orbitals of the atoms. In this way, the transition metals represent the transition between subgroup 2 elements and subgroup 12 (or 13) elements. Transition metals in the context of the present invention particularly comprise members of subgroup 3 of the periodic table: including Scandium (Sc), Yttrium (Y), and Lutetium (Lu), members of subgroup 4 of the periodic table: including Titan (Ti), Zirconium (Zr), and Hafnium (Hf), members of subgroup 5 of the periodic table: including Vanadium (V), Niobium (Nb), and Tantalum (Ta), members of subgroup 6 of the periodic table: including Chrome (Cr), Molybdenum (Mo), and Tungsten (W), members of subgroup 7 of the periodic table: including Manganese (Mn), Technetium (Tc), and Rhenium (Re), members of subgroup 8 of the periodic table: including Iron (Fe), Ruthenium (Ru), and Osmium (Os), members of subgroup 9 of the periodic table: including Cobalt (Co), Rhodium (Rh), and Iridium (Ir), members of subgroup 10 of the periodic table: including Nickel (Ni), Palladium (Pd), and Platin (Pt), members of subgroup 11 of the periodic table: including Copper (Cu), Silver (Ag), and Gold (Au), members of subgroup 12 of the periodic table: including Zinc (Zn), Cadmium (Cd), and Mercury (Hg); preferably members of period 4 of any of subgroups 1 to 12 of the periodic table: including Scandium (Sc), Titanium (Ti), Vanadium (V), Chromium (Cr), Manganese (Mn), Iron (Fe), Cobalt (Co), Nickel (Ni), Copper (Cu) and Zinc (Zn) and their metal ions and salts;

earth metals or members of the boron group, including members of group 3 of the periodic table: including Boron (B), Aluminium (Al), Gallium (Ga), Indium (In) and Thallium (Tl) and their metal ions and salts; preferably Boron (B) and Aluminium (Al) and their metal ions and salts;

metalloids or semi metals: including Boron (B), Silicon (Si), Germanium (Ge), Arsenic (As), Antimony (Sb), Tellurium (Te).and Polonium (Po), and their semi metal ions and salts; preferably Boron (B) and Silicon (Si) and their semi metal ions and salts;

In the context of the present invention, a further component may be selected from the group of surfactants may comprise, without being limited thereto, any surfactant, preferably any pharmaceutically acceptable surfactant, which is preferably suitable for spray drying or spray-freeze drying. More preferably, without being limited thereto, the surfactant is selected from the group consisting of Tween, e.g. Tween 80 (0.2%), Pluronics, e.g. Pluronic L121 (1.25%), Triton-X, SDS, PEG, LTAB, saponin, cholate, etc.

As another component, the liquid provided in step a) of the inventive method may additionally contain one or more compatible solid or liquid fillers or diluents or encapsulating compounds, which are preferably suitable for administration to a patient to be treated. The term "compatible" as used herein means that these constituents are capable of being mixed with the at least one RNA (free or in a complex with a cationic or polycationic compound), as defined according to the present invention, in such a manner that no interaction occurs, which would substantially reduce the integrity or biological activity of the at least one RNA, under typical use conditions. Pharmaceutically acceptable carriers, fillers and diluents must, of course, have sufficiently high purity and sufficiently low toxicity to make them suitable for administration to a person to be treated. Some examples of compounds, which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

In addition, the liquid provided in step a) of the inventive method may optionally contain further excipients or agents, such as stabilizers, for example EDTA, Tween, benzoic acid derivatives or RNAse inhibitors. Preferably, the liquid may further comprise any type of component or additive, which is compatible with the at least one RNA. Such an excipient is preferably selected from the group consisting of preservatives, antioxidants, antimicrobial agents, colorants, carriers, fillers, film formers, redispersants and disintegrants. Moreover, the liquid may also comprise a component or additive, preferably in very small amounts, such as defoamers, surfactants, viscosity enhancing agents, force control agents or the like.

The liquid provided in step a) of the inventive method is preferably a liquid or semi-liquid composition, which comprises at least one RNA as defined herein and at least one lyoprotectant as defined herein. The at least one RNA and the at least one lyoprotectant are preferably dissolved in the liquid provided in step a). In a preferred embodiment, the liquid is an aqueous solution of the at least one RNA and the at least one lyoprotectant, preferably comprising a solvent as defined herein. The liquid, as used herein, may also be a viscous solution, an emulsion, a dispersion, a suspension, a gel or the like.

The liquid provided in step a), preferably a solution comprising the at least one RNA and the at least one lyoprotectant, may be prepared by mixing the at least one RNA and the at least one lyoprotectant in the presence of a suitable solvent, preferably as defined herein. For instance, the liquid may be prepared by adding the at least one lyoprotectant, preferably a carbohydrate, more preferably a sugar, most preferably trehalose, to a liquid comprising the at least one RNA as defined herein, or by adding the at least one RNA as defined herein to a liquid comprising the at least one lyoprotectant, preferably a carbohydrate, more preferably a sugar, most preferably trehalose. Therein, the weight ratios and/or the concentrations are preferably as defined above. Such a solution for lyophilization as defined above has optionally been supplemented with further components, preferably as defined above. In a preferred embodiment, step a) comprises providing a liquid comprising the at least one RNA and a liquid comprising the at least one lyoprotectant, which are mixed in order to provide a liquid comprising at least one RNA and at least one lyoprotectant.

According to step b) of the inventive method, the liquid provided in step a) is introduced into a freeze drying chamber of a freeze dryer.

In the context of the present invention, the term 'freeze dryer' typically refers to an instrument, which allows the lyophilization liquid or semi-liquid formulations. Preferably, the freeze dryer as used herein can be controlled with respect to parameters characterizing the lyophilization process, such as temperature and pressure in a freeze drying chamber, which contains the liquid to be lyophilized. Such instruments are known in the art and readily available. It is particularly preferred that the heating rate and/or the cooling rate as well as the pressure can be regulated. This regulation is preferably performed in a semi-automatic or automatic manner, e.g. by programming the instrument before the beginning of the lyophilization process so that the instrument performs a desired lophilization process, for example by applying certain pre-determined steps (e.g. freezing, drying), and preferably the transition from one such step to another, under pre-determined temperatures and pressures. It is further preferred that the freeze dryer comprises a freeze drying chamber, wherein the atmosphere can preferably be controlled, i.e. by flooding the chamber (e.g. over specific gas inlets and outlets) with a specific gas, e.g. nitrogen. Such instruments are known in the art and readily available. Examples of commercially available instruments comprise, for instance, freeze dryer Alpha 2-4 (Martin Christ Gefriertrocknungsanlagen, Osterrode, Germany), Lyoflex 04 (BOC Edwards) or Epsilon 2-12D (Martin Christ Gefriertrocknungsanlagen, Osterrode, Germany).

In a preferred embodiment, the liquid provided in step a) is introduced into the drying chamber of a freeze dryer, wherein the liquid is provided in a suitable container, such as a vial, a tube or a cup, which is introduced into the drying chamber. Suitable containers for lyophilization are known in the art and are commercially available. Depending on the liquid amount and the envisaged application of the lyophilized composition, an appropriate container is chosen. In a preferred embodiment, the liquid is introduced into the drying chamber in glass vials, more preferably sterile glass vials. In a preferred embodiment, the liquid provided in step a) is provided in a 1-100R glass vial, preferably in a 1-50R glass vial, more preferably in a 2-20R glass vial, such as in a 2R or 20R glass vial (e.g. EZ-Fill glass vials from Ompi, glass vials from Schott, particularly Schott TopLyo®, glass vials from Gerresheimer, particularly Gx® vials, glass vials from Aluglas, or glass vials from SGD Pharma). More preferably, a container as used herein may have a lid, which can be partially closed (for example, in order to allow gas to enter or exit the vial) or fully closed (for example at the end of the lyophilization process). In a preferred embodiment, a container containing the liquid provided in step a) is introduced into the chamber with a partially closed lid, wherein the lid remains partially closed during the lyophilization process and wherein the lid is closed, preferably automatically and preferably before equilibrating the freeze drying chamber in step g), at the end of the lyophilization process. In a preferred embodiment, the liquid provided in step a) is provided in a container, preferably a vial, wherein the container is partially closed with a rubber stopper prior to introducing the liquid into the freeze drying chamber, preferably partially closed with a freeze drying rubber stopper, more preferably with a freeze drying coated rubber stopper, most preferably a fluoro- or Teflon-coated freeze drying rubber stopper, for example a fluoro-coated freeze drying rubber stopper (e.g. FluroTec® Rubber Stoppers manufactured by West Pharmaor or FluroTec® Rubber Stoppers from Daikyo Seiko Ltd.).

According to a preferred embodiment, the liquid provided in step a) is introduced into the freeze drying chamber in step b) of the method, wherein step b) comprises introducing the liquid into the freeze drying chamber at room temperature, preferably at a temperature in a range from 15° to 25° C., more preferably at a temperature in a range from 18° to 23° C., most preferably at a temperature in a range from 20° to 22° C. (e.g. 20° C.). In a preferred embodiment, the temperature of the liquid provided in step a) and/or the temperature of the freeze drying chamber is as defined above in step b). Step b) preferably comprises the introduction of the liquid into the freeze drying chamber, wherein the pressure in the freeze drying chamber is approximately equal to the pressure according to standard atmosphere (Atm). More preferably, the pressure in the drying chamber in step b) of the inventive method is about 1013.25 mbar.

The inventive method further comprises a step of cooling the liquid to a freezing temperature, wherein the cooling is performed at a defined cooling rate (step c)) and a step of freezing the liquid at the freezing temperature in order to obtain a frozen liquid (step d)).

In a preferred embodiment, the freezing temperature is a pre-determined temperature. With respect to the quality of the lyophilized product, it is important that an appropriate freezing temperature for freezing is chosen. In particular, the frozen liquid comprising the at least one RNA and the at least one lyoprotectant must remain below the collapse temperature (Tc) of the frozen liquid. Below the collapse temperature, a given formulation maintains their solid (frozen) state. However, at the collapse temperature, a frozen formulation typically loses its structure, leading to collapse and/or melting of the formulation. Preferably, the collapse temperature is the melting temperature of a composition. The collapse temperature is specific for a given composition and is typically determined empirically. Methods for determining the collapse temperature of a substance are known in the art and comprise, for example, by using a freeze-drying microscope, a differential thermal analyser (e.g. differential scanning calorimetry) or an electric impedance analyser (dielectric resistance analysis). The collapse temperature of a given composition typically increases with a decreasing amount of water, which is present in the composition. The freezing temperature is preferably pre-determined by selecting a temperature below the collapse temperature of a given composition.

According to a preferred embodiment, the freezing temperature in the inventive method is below the collapse temperature of the liquid provided in step a) or the frozen liquid obtained in step d), respectively.

In a further preferred embodiment, the freezing temperature is equal to or lower than the glass transition temperature (Tg') of the liquid provided in step a) or the frozen liquid obtained in step d), respectively. If a frozen amorphous composition is heated up to its specific glass transition temperature, the structure of the composition changes from brittle to flexible, without completely melting. The glass transition temperature is typically slightly lower than the collapse temperature or the melting temperature of a given composition. As used herein, the term 'glass transition temperature' also relates to the temperature, at which a liquid composition solidifies into an amorphous frozen composition. Like the collapse temperature described above, also the glass transition temperature is specific for a given substance or composition and varies with its water content. Also the glass transition temperature is typically determined empirically. Methods for determining the glass transition temperature of a substance or composition are known in the art and comprise, for example, by using a freeze-drying microscope, a differential thermal analyser (e.g. differential scanning calorimetry) or an electric impedance analyser (dielectric resistance analysis). The freezing temperature is preferably pre-determined by selecting a temperature equal to or below the glass transition temperature of a given composition.

The temperatures defined herein with respect to the inventive method typically refer to the respective temperatures in the freeze drying chamber. Depending on the type of instrument, the temperature in the freeze drying chamber may be determined by different means.

The temperature in the freeze drying chamber is preferably determined by determining the shelf temperature, the temperature of the liquid provided in step a) or the frozen liquid obtained in step d), respectively, or the temperature of a portion thereof.

As used herein, the term 'shelf temperature' typically relates to the temperature as measured via at least one probe, which is preferably positioned on the surface of the shelf. In the context of the inventive method, a 'shelf' is typically understood as any structure in the freeze drying chamber, which is suitable for supporting the liquid, which is to be lyophilized and which is provided, for example, in one or more containers, which are placed on such a structure. Preferably, the liquid to be lyophilized or a container containing such liquid is in physical contact with the shelf. The shelf temperature is preferably measured via at least one probe, which is preferably positioned on the surface of the shelf or which is alternatively integrated into the shelf. The thus determined shelf temperature preferably reflects the temperature of the liquid to be lyophilized.

In addition to the shelf temperature or as an alternative, the temperature of the liquid provided in step a), the frozen liquid obtained in step d), or a portion thereof, is measured via a probe, which is positioned in the liquid or the frozen liquid. Examples of suitable probe types comprise e.g. a PT100 platinum resistance thermometer, a PT1000 platinum resistance thermometer, a Cu—CuNi thermocouple, a NiCr—NiAl thermocouple, a NiCr—CuNi thermocouple, and a NiCr—Ni thermocouple.

The temperatures of the liquid provided in step a) and the frozen liquid obtained in step d), or the temperatures of a portion thereof, preferably correspond to the respective shelf temperatures. Accordingly, the temperatures of the liquid provided in step a) and the frozen liquid obtained in step d), or the temperatures of a portion thereof, are either equal to the respective shelf temperatures or correspond to the respective shelf temperatures in that the liquid reaches the shelf temperature with a short delay after the shelf or vice versa. Depending on the heating system and, in particular, the position of a heating element in the freeze drying chamber, either the liquid or the shelf may heat up or cool down first. Preferably, this delay is so small (e.g. in the range from 1 to 30 seconds) so that for practical considerations with respect to the temperature regulation in the inventive method—it is negligible.

In a preferred embodiment, the lyophilization is controlled by using the shelf temperature as a parameter. For example, a lyophilization process is typically programmed by using the temperatures as defined herein as shelf temperatures. Optionally, the actual temperature of the liquid provided in step a) and/or the frozen liquid obtained in step d), or a portion thereof, may be measured directly, e.g. during the establishment of a production process, in addition to the shelf temperature.

In preferred embodiments of the invention, the freezing temperature is equal to or at least 0.5° C., 1° C., 2° C., 3° C., 4° C., 5° C., 6° C., 7° C., 8° C., 9° C., 10° C., 11° C., 12° C., 13° C., 14° C. or 15° C. lower than the glass transition temperature (Tg') of the liquid provided in step a) or the frozen liquid obtained in step d), respectively. In a particularly preferred embodiment, the freezing temperature is in a range from 0.5° C. to 25° C., preferably from 1° C. to 20° C., more preferably from 5° C. to 15° C. below the glass transition temperature (Tg') of the liquid provided in step a) or the frozen liquid obtained in step d), respectively.

In a preferred embodiment, the liquid provided in step a) of the inventive method or the frozen liquid obtained in step d) has a glass transition temperature in a range from −15° C. to −50° C., preferably in a range from −25° C. to −40° C., more preferably in a range from −28° C. to −37° C., most preferably in a range from −30° C. to −35° C.

Preferably, the freezing temperature in step c) and d) of the inventive method is below −30° C., more preferably below −35° C. and most preferably below −38° C. Further preferably, the freezing temperature in step c) and d) of the inventive method is in a range from −55° C. to −30° C., preferably from −50° C. to −35° C., more preferably in a range from −45° C. to −35° C. and most preferably in a range from −42° C. to −38° C. In a particularly preferred embodiment, the freezing temperature is about −40° C.

According to a preferred embodiment, step c) of the inventive method comprises cooling the liquid provided in step a) to a freezing temperature, wherein the cooling rate is performed at a defined cooling rate. Preferably, the cooling rate in step c) is less than 2° C./min, more preferably less than 1.5° C./min, even more preferably less than 1° C./min and most preferably less than 0.5° C./min. Alternatively, the cooling rate in step c) may be in a range from 0.1° C./min to 2° C./min, preferably in a range from 0.5° C./min to 1.5° C./min. In a particularly preferred embodiment, a cooling rate of about 0.5° C./min is used in step c). The cooling rate is preferably constant during step c).

In a specific embodiment of the inventive method, the freezing temperature is maintained for at least 1 hour, more preferably for at least 2 hours and most preferably for at least 3 hours.

The method of the invention further comprises a step e), which comprises reducing the pressure in the freeze drying chamber to a pressure below atmospheric pressure. Preferably, the pressure in the freeze drying chamber is reduced to a pressure below atmospheric pressure subsequently to the freezing of the liquid provided in step a). In a preferred embodiment, the pressure in the freeze drying chamber is reduced to a pressure below atmospheric pressure before or at the beginning of the drying step. Most preferably, the pressure is reduced before the temperature is increased.

According to a preferred embodiment, step e) comprises reducing the pressure in the freeze drying chamber to a pressure in a range from about 0.001 mbar to about 0.3 mbar.

In the context of the present invention, the pressure in the freeze drying chamber is determined by any suitable means. Different types of manometers are known in the art. Preferably, a direct (gas independent) pressure/vacuum capacitance manometers, a Pirani manometer or a MKS manometer, e.g. Baratron®, is used.

The inventive method further comprises a step f), which comprises drying the frozen liquid obtained in step d) in order to obtain a lyophilized composition comprising at least one RNA and at least one lyoprotectant. According to one embodiment, step f) comprises heating the frozen liquid obtained in step d) to a drying temperature.

The drying temperature is typically the shelf temperature, which provides sufficient energy to compensate the energy, which is removed from the environment of the frozen liquid due to sublimation (sublimation energy). During primary drying the front of sublimation migrates from top to bottom or from the periphery to the center of the frozen liquid and the thickness of the dried portion of the composition increases. The dried portion typically interferes with the heat transfer from the environment to the frozen liquid to be dried. With increasing thickness of the dried portion of the composition, the heat transfer declines and the shelf temperature must be increased to ensure that sufficient energy is provided to compensate the sublimation energy. If the amount of energy, which is applied to the frozen liquid, is larger than the amount of energy, which is compensated by sublimation, the temperature of the frozen liquid increases. If the temperature of the frozen liquid increases above its glass transition temperature or its collapse temperature, the frozen liquid starts thawing and thereby loses its structure. The drying temperature is thus preferably kept below collapse temperature, more preferably below the glass transition temperature during sublimation of the frozen liquid. The drying temperature is preferably a pre-determined temperature. More preferably, the drying temperature is the temperature, preferably the shelf temperature, which provides the frozen liquid with at least the amount of energy, which is compensated by sublimation, wherein the drying temperature is preferably below the minimum temperature, which is required for heating the frozen liquid to the respective glass transition temperature or to the respective collapse temperature. According to a preferred embodiment, the drying temperature is sufficiently high to provide the frozen liquid with the amount of energy, which is compensated by sublimation. In preferred embodiments, the drying temperature is determined empirically, preferably as described herein with respect to the collapse temperature or the glass transition temperature. In another preferred embodiment, the drying temperature may be determined by calculating the sublimation energy by a method known in the art (see, for instance, Pikal, M. J.: Freeze-Drying of Proteins: Process, Formulation, and Stability, in: Formulation and Delivery of Proteins and Peptides, ed. by J. L. Cleland, R. Langer, ACS Symposium Series 567, 1994, pp. 120-133).

The drying temperature is preferably below the collapse temperature of the frozen liquid obtained in step d). More preferably, the drying temperature in step f) is below the glass transition temperature of the frozen liquid obtained in step d). In specific embodiments, the drying temperature is in a range from −40° C. to 40° C., preferably from −30° C. to 30°, more preferably from −25° C. to 25° C. The overall heating rate from the freezing temperature to the final drying temperature is preferably in a range from 0.1° C./h to 20° C./h, more preferably in a range from 2° C./h to 15° C./h, most preferably in a range from 5° C./h to 15° C./h.

It is believed that the heating rate in step f) has an impact on the quality of the lyophilized composition. In particular, it is believed that the integrity and/or the biological activity of the at least one RNA can be influenced in a positive manner by selecting an appropriate heating rate. According to a preferred embodiment, the heating rate in step f) of the inventive method is thus preferably in a range from 0.1° C./h to 20° C./h, more preferably in a range from 2° C./h to 15° C./h, even more preferably in a range from 3° C./h to 12° C./h, even more preferably in a range from 4° C./h to 11° C./h, most preferably in a range from about 5° C./h to about 10° C./h or from 5° C./h to 10°/h. Alternatively, the heating rate in step f) is 30° C./h or less, 20° C./h or less, 15° C./h or less, 12° C./h or less, 11° C. or less, or 10° C./h or less. In a preferred embodiment, the above defined heating rate is the overall heating rate applied in step f) of the inventive method, more preferably the overall heating rate from the freezing temperature to the final drying temperature.

In a preferred embodiment, step f) comprises at least two drying steps. Preferably, step f) of the inventive method comprises two drying steps, primary drying step f1) and secondary drying step f2). In the primary drying step f1), free, i.e. unbound, water surrounding the at least one RNA and optionally further components, typically escapes from the solution. Subsequent thereto, water being bound on a molecular basis by the at least one RNA may be removed in a secondary drying step f2) by adding thermal energy. In both cases the hydration sphere around the at least one RNA is lost. Preferably, the primary drying step f1) comprises heating the frozen liquid to a primary drying temperature, which is preferably lower than a secondary drying temperature, to which the frozen liquid is heated in the secondary drying step f2). More preferably, the pressure in the primary drying step f1) ('primary drying pressure') is higher than the pressure in the secondary drying step f2) ('secondary drying pressure').

According to a further embodiment, step e) comprises reducing the pressure in the freeze drying chamber to a primary drying pressure, which is applied before or concomittantly with the heating from the freezing temperature to the primary drying temperature and which is maintained during the primary drying step f1); and subsequently reducing the pressure in the freeze drying chamber to a secondary drying pressure, which is applied before or concomittantly with the heating from the primary drying temperature to the secondary drying temperature and which is maintained during the secondary drying step f2).

The primary drying step f1) may be carried out at normal pressure, e.g. in the range of about 980 to about 1045 millibar (mbar), e.g. about 1013 mbar, but also may be carried out by lowering the pressure to a primary drying pressure. Preferably, the primary drying pressure is in the range of a few millibar, e.g. in the range of about 0.001 mbar (1 pbar) to about 0.3 mbar (300 pbar), preferably in the range of about 0.01 mbar (10 pbar) to about 0.2 mbar (200 pbar), even more preferably in the range of about 0.05 mbar (50 pbar) to about 1.5 mbar (150 pbar), e.g. about 0.1 mbar (100 pbar). In this primary drying step, pressure is typically controlled through the application of partial vacuum. The vacuum allows speeding up sublimation, making it useful as a deliberate drying process. Furthermore, a cold condenser chamber and/or condenser plates may be used to provide (a) surface(s) for the water vapor to re-solidify on. Condenser temperatures may be in the range of <−70° C., in the range of <−60° C., in the range of <−50° C. <−50° C. is particularly preferred. Alternatively, instead of lowering the pressure, heat may be supplied to the sample to allow for the water to sublimate. The amount of heat necessary can be calculated using the sublimating molecules' latent heat of sublimation. In this initial drying phase, about 95% (w/w) of the water in the material is sublimated. This phase may be carried out slow to avoid applying too much heat and possible alteration or damage of the structure of the nucleic acid to be lyophilized.

In a preferred embodiment, the primary drying step comprises adjusting the temperature to the primary drying temperature, which is preferably in the range from about −40° C. to about +20° C., e.g. in the range from about −30° C. to about +20° C., in the range from about −20° C. to about +20° C., in the range from about −10° C. to about +10° C., in the range from about −40° C. to about +10° C., in the range from about −30° C. to about +10° C., in the range from about −20° C. to about +10° C., in the range from about −20° C. to about +/−0° C., or in the range from about −20° C. to about −10° C. A primary drying temperature of −10° C. is particularly preferred. As a further alternative, the primary drying step f1) is carried out at a primary drying temperature and a primary drying pressure as defined above.

Preferably, the temperature is increased from the freezing temperature to the primary drying temperature at a defined heating rate. More preferably, the temperature is increased in a first step of primary drying (f1a), preferably from the freezing temperature to the primary drying temperature, at a heating rate in the range from 0.1° C./h to 10° C./h, more preferably in the range from 1° C./h to 10° C./h or in the range from 2° C./h to 8° C./h, and most preferably in the range from 4° C./h to 6° C./h (e.g. 5° C./h). In the second step of primary drying (f1b) the primary drying temperature is applied for at least 5 hours, more preferably for at least 7 hours, and most preferably for at least 10 hours (e.g. 11 hours).

The secondary drying step f2) typically aims to remove unfrozen water molecules bound in the structure of the RNA (sequence), since the ice (frozen water molecules) is usually removed in the primary drying step f1) above. In this secondary drying step f2), the temperature is typically raised higher than in the primary drying step, and can even be above 0° C., to break any physico-chemical interactions that have formed between the water molecules and the frozen material. Alternatively or additionally, the pressure may be lowered in this stage to encourage desorption.

In a preferred embodiment, the secondary drying step f2) comprises adjusting the temperature to a secondary drying temperature and/or adjusting the pressure to a secondary drying pressure. In a specific embodiment, the secondary drying temperature is equal to the primary drying temperature and/or the secondary drying pressure is equal to the primary drying pressure. More preferably, the secondary drying temperature is in the range from about +10° C. to about +40° C., preferably in the range from about +10° C. to about +30° C., and more preferably in the range from about +15° C. to about +25° C. e.g. about 20° C. The pressure is preferably adjusted to the secondary drying pressure. Said secondary drying pressure is preferably in the range of a few millibars, e.g. as defined above for the primary drying pressure, or, more preferably, in the range from about 0.001 mbar (1 pbar) to about 0.1 mbar (100 pbar), preferably in the range from about 0.01 mbar (10 pbar) to about 0.1 mbar (100 pbar), even more preferably in the range from about 0.02 mbar (20 pbar) to about 0.08 mbar (80 pbar), e.g. about 0.045 mbar (45 pbar).

According to a preferred embodiment, in a first step of secondary drying (f2a)), the pressure is adjusted from the primary drying pressure to the secondary drying pressure, preferably by reducing the pressure as defined above, without increasing the temperature. In a second step of secondary drying (f2b)), the temperature is preferably increased to the secondary drying temperature, preferably as defined above.

In specific embodiments, the temperature is adjusted from the primary drying temperature to the secondary drying temperature at a defined heating rate. In one embodiment, the temperature is increased, preferably in a second step of secondary drying (f2b), in the range from 0.1° C./h to 20° C./h, more preferably in the range from 5° C./h to 15° C./h, and most preferably in the range from 8° C./h to 12° C./h (e.g. 10° C./h). In a third step of secondary drying (f2c) the secondary drying temperature is maintained for at least 3 hours, more preferably for at least 5 hours, and most preferably for at least 7 hours.

After completion of step f) of the inventive method, a lyophilized composition is typically obtained that comprises the at least one RNA and the at least one lyoprotectant.

Subsequent to step f), the freeze drying chamber is optionally flooded with an inert gas, preferably before step g) of the inventive method. Preferably, the inert gas is selected from the group consisting of nitrogen, carbon dioxide, helium, neon, argon, xenon and krypton. The freeze drying chamber is preferably flooded with the inert gas, preferably as defined herein, at a pressure in the range from standard atmosphere (Atm) (1013.25 mbar) to 100 mbar, preferably in the range from standard atmosphere (Atm) (1013.25 mbar) to 400 mbar, more preferably in the range from 900 mbar to 700 mbar. Most preferably, the freeze drying chamber is flooded with the inert gas at a pressure of 800 mbar.

In a preferred embodiment, a container containing the lyophilized composition, which is obtained according to the inventive method, is closed before the freeze drying chamber is opened. For this purpose, the at least one RNA and the at least one lyoprotectant are preferably already lyophilized in a suitable container, which can be closed. The optional step of closing and/or sealing a container comprising the lyophilized composition may be carried out independently of whether or not the freeze drying chamber was before flooded with an inert gas as described herein. According to one alternative, a container containing the lyophilized composition, which is obtained according to the inventive method, is closed before the freeze drying chamber is equilibrated to atmospheric pressure. Preferably, a container containing the lyophilized composition is closed automatically, for instance by fully closing a partially closed lid, such as a rubber stopper. More preferably, a container containing the lyophilized composition is closed hermetically, preferably before the freeze drying chamber is equilibrated to atmospheric pressure and/or before the freeze drying chamber is opened. Alternatively, a container containing the lyophilized composition, which is obtained according to the inventive method, is closed, preferably automatically, and, additionally sealed, for example by crimping a cover (e.g. an aluminum cap) over the lid (e.g. a rubber stopper) and the rim of the container opening (e.g. a neck of a vial).

The inventive method further comprises a step g), which comprises equilibrating the pressure in the freeze drying chamber to atmospheric pressure (preferably about 1013 mbar) and removing the lyophilized RNA from the freeze drying chamber. Preferably, step g) further comprises adjusting the temperature in the freeze drying chamber to ambient temperature, e.g. room temperature.

As a product of the lyophilization method as described herein, preferably after carrying out step a), b), c), d), e), f) and g), a lyophilized composition comprising at least one RNA and at least one lyoprotectant is preferably obtained. In a further aspect, the present invention thus further concerns a lyophilized composition comprising at least one RNA and at least one lyoprotectant, which is obtainable by the inventive method.

The lyophilized composition obtainable by the inventive method may further comprise a further component or a combination of components, preferably as described herein with respect to the inventive method.

The lyophilized composition comprising at least one RNA and at least one lyoprotectant is preferably characterized by a glass transition temperature (Tg), which is preferably equal to or higher than 60° C., more preferably equal to or higher than 70° C., most preferably equal to or higher than 80° C. According to a preferred embodiment, the glass transition temperature of the lyophilized composition is in a range from 50° C. to 200° C., preferably from 60° C. to 120° C., more preferably from 70° C. to 100° C. and most preferably from about 78° C. to about 88° C.

In preferred embodiments, the lyophilized composition obtainable by the inventive method is characterized by a residual moisture content, which is preferably in the range from about 0.1% (w/w) to about 10% (w/w), more preferably in the range from about 1% (w/w) to about 8% (w/w), even more preferably in the range from about 2% (w/w) to about 5% (w/w), most preferably in the range from about 3% (w/w) to 4%, e.g. 3% (w/w)±2% (w/w), or 3% (w/w)±1% (w/w). Further preferably, the residual water content of the lyophilized composition obtainable by the inventive method is equal to or less than 10% (w/w), more preferably equal to or less than 7% (w/w), even more preferably equal to or less than 5% (w/w), most preferably equal to or less than 4% (w/w).

As used herein, the term "residual moisture content" (or "residual moisture") typically refers to the total amount of solvent present in the lyophilized composition. Said total amount of residual solvents in the lyophilized composition is determined using any suitable method known in the art. For example, methods for determining the residual moisture content comprise the Karl-Fischer-titrimetric technique or the thermal gravimetric analysis (TGA) method. In a preferred embodiment, the residual solvent comprised in the lyophilized composition is water or an essentially aqueous solution and the residual moisture content is determined by the Karl-Fischer-titrimetric technique. Without being bound by any theory, the low residual moisture content of the lyophilized composition obtainable by the inventive method is expected to contribute to its excellent storage stability.

The lyophilized composition obtainable by the inventive method is particularly suitable as storage-stable form of RNA. The inventors have surprisingly found that the storage stability of the at least one RNA in the lyophilized composition is excellent and the RNA molecule remains functional after extended storage periods. The storage stability of the RNA is typically determined through determination of the relative (structural) integrity and the biological activity after a given storage period, e.g. via time-course in vitro expression studies.

The relative integrity is preferably determined as the percentage of full-length RNA (i.e. non-degraded RNA) with respect to the total amount of RNA (i.e. full-length RNA and degraded RNA fragments (which appear as smears in gel electrophoresis)), preferably after deduction of the LOD (3×background noise), for example, by using the software QuantityOne from BioRad.

The lyophilized composition obtainable by the inventive method allows significantly longer storage at temperatures from −80° C. to 60° C. than the corresponding RNAs in WFI or other injectable solutions. Particularly, the lyophilized composition obtainable by the inventive method can be stored at room temperature, which simplifies shipping and storage. Preferably, the lyophilized composition is stored with or without shielding gas. In one embodiment, single doses of the lyophilized composition are packaged and sealed. Alternatively, multiple doses can be packaged in one packaging unit. Single dose packaging in vials, syringes, blisters or capsules is preferably used in order to prevent cross-contamination.

Preferably, the relative integrity of the at least one RNA in the lyophilized composition obtainable by the inventive method is at least 70%, more preferably at least 75%, at least 80%, at least 85%, at least 90% or at least 95% after storage at room temperature for preferably at least one week, more preferably for at least one month, even more preferably for at least 6 months and most preferably for at least one year.

Further preferably, the biological activity of the at least one RNA of the lyophilized composition after storage at room temperature, preferably as defined above with respect to the relative integrity of the at least one RNA, is preferably at least 70%, more preferably at least 75%, at least 80%, at least 85%, at least 90% or at least 95% of the biological activity of the freshly prepared RNA. The biological activity is preferably determined by analysis of the amounts of protein expressed from reconstituted RNA and from freshly prepared RNA, respectively, e.g. after transfection into a mammalian cell line or into a subject. Alternatively, the biological activity may be determined by measuring the induction of an (adaptive or innate) immune response in a subject.

In a further aspect, the present invention regards the use of a lyoprotectant for lyophilizing RNA, wherein the use comprises controlled cooling and/or controlled heating of the RNA and the lyoprotectant. In particular, the invention provides the use of a lyoprotectant for lyophilizing RNA, wherein the use comprises a lyophilization process, wherein the lyophilization process comprises controlled cooling, preferably as defined herein, more preferably defined by the temperatures and/or the cooling rates defined herein with respect to the inventive method for lyophilizing RNA, and/or wherein the lyophilization process comprises controlled heating, preferably as defined herein, more preferably defined by the temperatures and/or the heating rates defined herein with respect to the inventive method for lyophilizing RNA. In a preferred embodiment, the invention provides the use of a carbohydrate compound, more preferably a sugar, even more preferably trehalose for lyophilizing RNA under controlled cooling and/or heating conditions, preferably as defined herein. In a particularly preferred embodiment, the invention provides the use of a lyoprotectant for lyophilizing RNA, wherein the use comprises any one of the features or any combination of the features as described herein with regard to the inventive method for lyophilizing RNA.

In a further aspect, the present invention further provides the use of the inventive method in the manufacture of a medicament or a vaccine.

According to yet another aspect of the present invention, a pharmaceutical composition is provided, which comprises or consists of the lyophilized composition obtainable by the inventive method for lyophilizing RNA. In a preferred embodiment, the inventive pharmaceutical composition comprises at least one additional pharmaceutically acceptable ingredient, such as a pharmaceutically acceptable carrier and/or vehicle. The inventive pharmaceutical composition may optionally be supplemented with further components as defined above with regard to the liquid provided in step a) of the inventive method for lyophilizing RNA. The inventive pharmaceutical composition may be prepared as a whole by the inventive method.

As a first ingredient, the inventive pharmaceutical composition comprises the at least one RNA as defined herein. In particular, the first ingredient of the inventive pharmaceutical composition is the lyophilized composition obtainable by the inventive method for lyophilizing RNA. Preferably, the at least one RNA as defined herein represents a pharmaceutically active ingredient of the pharmaceutical composition.

As a second ingredient the inventive pharmaceutical composition may comprise another class of compounds, which may be added to the inventive pharmaceutical composition in this context, may be selected from at least one pharmaceutically active component. A pharmaceutically active component in this context is a compound that has a therapeutic effect against a particular medical indication, preferably cancer diseases, autoimmune disease, allergies, infectious diseases or a further disease as defined herein. Such compounds include, without implying any limitation, preferably compounds including, without implying any limitation, peptides or proteins (e.g. as defined herein), nucleic acid molecules, (therapeutically active) low molecular weight organic or inorganic compounds (molecular weight less than 5,000, preferably less than 1,000), sugars, antigens or antibodies (e.g. as defined herein), therapeutic agents already known in the prior art, antigenic cells, antigenic cellular fragments, cellular fractions; modified, attenuated or de-activated (e.g. chemically or by irridation) pathogens (virus, bacteria etc.), etc.

Furthermore, the inventive pharmaceutical composition may comprise a pharmaceutically acceptable carrier and/or vehicle. In the context of the present invention, a pharmaceutically acceptable carrier typically includes the liquid or non-liquid basis of the inventive pharmaceutical composition. If the inventive pharmaceutical composition is provided in liquid form, the carrier will typically be pyrogen-free water; isotonic saline or buffered (aqueous) solutions, e.g phosphate, citrate etc. buffered solutions. Particularly for injection of the inventive pharmaceutical composition, water or preferably a buffer, more preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred aspect, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Furthermore, organic anions of the aforementioned cations may be contained in the buffer. According to a more preferred aspect, the buffer suitable for injection purposes as defined above, may contain salts selected from sodium chloride (NaCl), calcium chloride ($CaCl_2$) and optionally potassium chloride (KCl), wherein further anions may be present additional to the chlorides. $CaCl_2$ can also be replaced by another salt like KCl. Typically, the salts in the injection buffer are present in a concentration of at least 50 mM sodium chloride (NaCl), at least 3 mM potassium chloride (KCl) and at least 0.01 mM calcium chloride ($CaCl_2$). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person and may be as defined above.

However, one or more compatible solid or liquid fillers or diluents or encapsulating compounds may be used as well for the inventive pharmaceutical composition, which are suitable for administration to a patient to be treated. The term "compatible" as used here means that these constituents of the inventive pharmaceutical composition are capable of being mixed with the lyophilized composition obtainable by the inventive method for lyophilizing RNA in such a manner that no interaction occurs, which would substantially reduce the pharmaceutical effectiveness of the inventive pharmaceutical composition under typical use conditions. Pharmaceutically acceptable carriers, fillers and diluents must, of course, have sufficiently high purity and sufficiently low toxicity to make them suitable for administration to a person to be treated. Some examples of compounds, which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

The inventive pharmaceutical composition may be administered orally, parenterally, by inhalation, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the inventive pharmaceutical composition may be administered by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or via infusion techniques. Sterile injectable forms of the inventive pharmaceutical compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation of the inventive pharmaceutical composition.

The inventive pharmaceutical composition as defined above may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the lyophilized composition obtainable by the inventive method for lyophilizing RNA, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the components as defined above suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

The inventive pharmaceutical composition typically comprises a "safe and effective amount" of the components of the inventive pharmaceutical composition as defined above, particularly of at least one RNA as comprised in the lyophilized composition obtainable by the inventive method for lyophilizing RNA. As used herein, a "safe and effective amount" means an amount of the at least one RNA that is sufficient to significantly induce a positive modification of a disease or disorder as defined herein. At the same time, however, a "safe and effective amount" is small enough to avoid serious side-effects, that is to say to permit a sensible relationship between advantage and risk. The determination of these limits typically lies within the scope of sensible medical judgment. A "safe and effective amount" of the components of the inventive pharmaceutical composition, particularly of the at least one RNA, will furthermore vary in connection with the particular condition to be treated and also with the age and physical condition of the patient to be treated, the body weight, general health, sex, diet, time of administration, rate of excretion, drug combination, the activity of the specific (lyophilized) nucleic acid (sequence) employed, the severity of the condition, the duration of the treatment, the nature of the accompanying therapy, of the particular pharmaceutically acceptable carrier used, and similar factors, within the knowledge and experience of the accompanying doctor. The inventive pharmaceutical composition may be used for human and also for veterinary medical purposes, preferably for human medical purposes, as a pharmaceutical composition in general or as a vaccine.

According to a specific aspect, the lyophilized composition obtainable by the inventive method for lyophilizing RNA or the inventive pharmaceutical composition may be provided as a vaccine. Such an inventive vaccine is typically composed like the inventive pharmaceutical composition, i.e. it contains the lyophilized composition obtainable by the inventive method for lyophilizing RNA as defined above and optionally a pharmaceutically acceptable carrier and/or vehicle. Further components may be as defined above for the inventive pharmaceutical composition. The inventive vaccine preferably supports at least an innate immune response of the immune system of a patient to be treated. Additionally, the inventive vaccine furthermore may also elicit an adaptive immune response, preferably, if the at least one RNA of the inventive vaccine encodes an antigen (or antibody), which elicits an adaptive immune response, or an antigen is added to the inventive vaccine, which can effectively induce an adaptive immune response.

The inventive vaccine may also comprise a pharmaceutically acceptable carrier, adjuvant, and/or vehicle as defined above for the inventive pharmaceutical composition. In the specific context of the inventive vaccine, the choice of a pharmaceutically acceptable carrier is determined in principle by the manner, in which the inventive vaccine is administered. The inventive vaccine can be administered, for example, systemically or locally. Preferred routes of administration of the inventive vaccine are generally the same as the routes described herein with respect to the inventive pharmaceutical composition. Routes for systemic administration in general include, for example, transdermal, oral, parenteral routes, including subcutaneous, intravenous, intramuscular, intraarterial, intradermal and intraperitoneal injections and/or intranasal/intrapulmonal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines herein may be administered by an intradermal, subcutaneous, or intramuscular route. Inventive vaccines are therefore preferably formulated in liquid (or sometimes in solid, e.g. as an aerosol) form. The suitable amount of the inventive vaccine to be administered can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those, which are suitable for use in lotions, creams, gels and the like. If the inventive vaccine is to be administered orally, tablets, capsules and the like are the preferred unit dose form. The pharmaceutically acceptable carriers for the preparation of unit dose forms, which can be used for oral administration, are well known in the prior art. The choice thereof will depend on secondary considerations such as taste, costs and storability, which are not critical for the purposes of the present invention, and can be made without difficulty by a person skilled in the art.

Further additives which may be included in the inventive vaccine are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

According to a specific embodiment, the inventive vaccine may comprise an adjuvant. In this context, an adjuvant may be understood as any compound, which is suitable to initiate or increase an immune response of the innate immune system, i.e. a non-specific immune response. In other terms, when administered, the inventive vaccine preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal.

In this context, the adjuvant is preferably selected from compounds, which are known to be immune-stimulating due to their binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

According to a further aspect, the present invention also provides a kit, particularly as a kit of parts. Such a kit of parts may contain e.g. the lyophilized composition obtainable by the inventive method, the inventive pharmaceutical composition or the inventive vaccine as defined above, preferably divided into different parts of the kit. As an example, the inventive pharmaceutical composition or the inventive vaccine may be prepared as a kit of parts, e.g. by incorporating into one or more parts of the kit (all or at least some components of) the inventive pharmaceutical composition or the inventive vaccine as described herein (whereby at least the at least one RNA is included), or the lyophilized composition as such, as a dry formulation, i.e. devoid of any liquid component, and in at least one further separate part of the kit a solvent and/or a buffer as described herein with respect to the liquid provided in step a) of the inventive method, the inventive pharmaceutical composition or the inventive vaccine or any further solvent and/or buffer as described herein for lyophilization, transfection and/or injection. Alternatively, the inventive pharmaceutical composition or the inventive vaccine may be prepared as a kit of parts, e.g. by incorporating into one or more parts of the kit only the lyophilized composition obtainable by the inventive method, as described herein, and in at least one further separate part of the kit a solvent and/or a buffer as described herein for the liquid provided in step a) of the inventive method, for the inventive pharmaceutical composition or the inventive vaccine or any further liquid and/or buffer as described herein for lyophilization, transfection and/or injection. Without being limited thereto, further ingredients of the kit may include components as defined above, e.g. (solutions comprising) proteins, amino acids, alcohols, carbohydrates, metals or metal ions, surfactants, polymers or complexing agents, and/or buffers, preferably all as defined above. These further ingredients may be contained in different parts of the kit (or kit of parts). The kit or kit of parts as described above may contain optionally technical instructions with information on the administration and dosage of the inventive composition. Such a kit, preferably kit of parts, may be applied, e.g., for any of the above mentioned applications or uses.

The present invention furthermore provides several applications and uses of the lyophilized composition obtainable by the inventive method, the inventive pharmaceutical composition, the inventive vaccine or the inventive kit or kit of parts.

According to one aspect, the invention concerns the use of the lyophilized composition obtainable by the inventive method for the preparation of a medicament for the prophylaxis, treatment and/or amelioration of a disorder or a disease, preferably as defined herein. In a preferred embodiment, the medicament is a vaccine.

According to a further aspect, the present invention is directed to the use of the lyophilized composition obtainable by the inventive method, the inventive pharmaceutical composition, the inventive vaccine or the inventive kit or kit of parts, as defined herein, in the treatment or prevention of a disease, preferably as defined herein. In particular, the present invention concerns the first medical use of the the lyophilized composition obtainable by the inventive method as a medicament. The medicament may be in the form of a pharmaceutical composition, in the form of a vaccine as a specific form of pharmaceutical compositions or in the form of a kit or a kit of parts. The invention thus provides the lyophilized composition obtainable by the inventive method, the inventive pharmaceutical composition, the inventive vaccine or the inventive kit or kit of parts for use in the treatment or prophylaxis of a disorder or a disease. A pharmaceutical composition in the context of the present invention typically comprises or consists of the lyophilized composition obtainable by the inventive method, optionally further ingredients, preferably as defined above, and optionally a pharmaceutically acceptable carrier and/or vehicle, preferably as defined above.

According to another aspect, the present invention is directed to the second medical use of the lyophilized composition obtainable by the inventive method, of a pharmaceutical composition, of a vaccine as a specific form of pharmaceutical compositions or of the inventive kit or kit of parts. The present invention provides the lyophilized composition obtainable by the inventive method for lyophilizing RNA, the inventive pharmaceutical composition, the inventive vaccine or the inventive kit or kit of parts for use in the treatment of diseases as defined herein, preferably for use in the prophylaxis, treatment and/or amelioration of various diseases as defined herein, preferably selected from neoplasms (e.g. cancer or tumor diseases), infectious and parasitic diseases, preferably viral, bacterial or protozoological infectious diseases, autoimmune diseases, allergies or allergic diseases, monogenetic diseases, i.e. (hereditary) diseases, or genetic diseases in general, diseases which have a genetic inherited background and which are typically caused by a single gene defect and are inherited according to Mendel's laws, chromosomal abnormalities, cardiovascular diseases, diseases of the blood and blood-forming organs, endocrine, nutritional and metabolic diseases, mental and behavioural disorders, diseases of the nervous system, diseases of the eye and adnexa, diseases of the ear and mastoid process, diseases of the circulatory system, diseases of the respiratory system, diseases of the digestive system, diseases of the skin and subcutaneous tissue, diseases of the musculoskeletal system and connective tissue, and diseases of the genitourinary system.

According to a further aspect, the present invention concerns a method of treating or preventing a disorder or a disease, wherein the method comprises administering to a subject in need thereof a pharmaceutically effective amount, preferably as defined herein, of the lyophilized composition obtainable by the inventive method, the inventive pharmaceutical composition, or the inventive vaccine. Preferably, the method is for treating or preventing a disorder or a disease selected from neoplasms (e.g. cancer or tumor diseases), infectious and parasitic diseases, preferably viral, bacterial or protozoological infectious diseases, autoimmune diseases, allergies or allergic diseases, monogenetic diseases, i.e. (hereditary) diseases, or genetic diseases in general, diseases which have a genetic inherited background and which are typically caused by a single gene defect and are inherited according to Mendel's laws, chromosomal abnormalities, cardiovascular diseases, diseases of the blood and blood-forming organs, endocrine, nutritional and metabolic diseases, mental and behavioural disorders, diseases of the nervous system, diseases of the eye and adnexa, diseases of the ear and mastoid process, diseases of the circulatory system, diseases of the respiratory system, diseases of the digestive system, diseases of the skin and subcutaneous tissue, diseases of the musculoskeletal system and connective tissue, and diseases of the genitourinary system., or any further disease mentioned herein.

The present invention also allows treatment of diseases, which have not been inherited, or which may not be summarized under the above categories. Such diseases may include e.g. the treatment of patients, which are in need of a specific protein factor, e.g. a specific therapeutically active protein as mentioned above. This may e.g. include dialysis patients, e.g. patients, which undergo a (regular) a kidney or renal dialysis, and which may be in need of specific therapeutically active proteins as defined above, e.g. erythropoietin (EPO), etc.

Likewise, diseases in the context of the present invention may include cardiovascular diseases chosen from, without being limited thereto, coronary heart disease, arteriosclerosis, apoplexy and hypertension, etc.

Finally, diseases in the context of the present invention may be chosen from neuronal diseases including e.g. Alzheimer's disease, amyotrophic lateral sclerosis, dystonia, epilepsy, multiple sclerosis and Parkinson's disease etc.

BRIEF DESCRIPTION OF THE FIGURES

The figures shown in the following are merely illustrative and shall describe the present invention in a further way. These figures shall not be construed to limit the present invention thereto.

FIG. 1: SEQ ID NO: 1, which is the mRNA sequence corresponding to PpLuc(GC)-muag-A64-C30.

FIG. 2: SEQ ID NO: 2, which is the mRNA sequence corresponding to HA(GC)-muag-A64-C30-histone stem-loop.

FIG. 3: SEQ ID NO: 3, which is the mRNA sequence corresponding to HsFOLH1(GC)-muag-A64-C30-histone stem-loop.

FIG. 4: SEQ ID NO: 9, which is the mRNA sequence corresponding to RAV-G(GC)-muag-A64-C30-histone stem-loop.

FIG. 6: Optimization of a lyophilization cycle under controlled freezing conditions (Example 4)

A. Residual moisture content of compositions lyophilized under controlled freezing conditions in the presence of different amounts of trehalose, wherein the residual moisture content was determined after storage of the lyophilized compositions at 50° C. (without controlling the relative humidity) for 3 months.

B. Relative integrity of mRNA lyophilized under controlled freezing conditions in the presence of different amounts of trehalose, wherein the lyophilized samples were stored for 3 months at −50° C. (without controlling the relative humidity).

Figure 7:
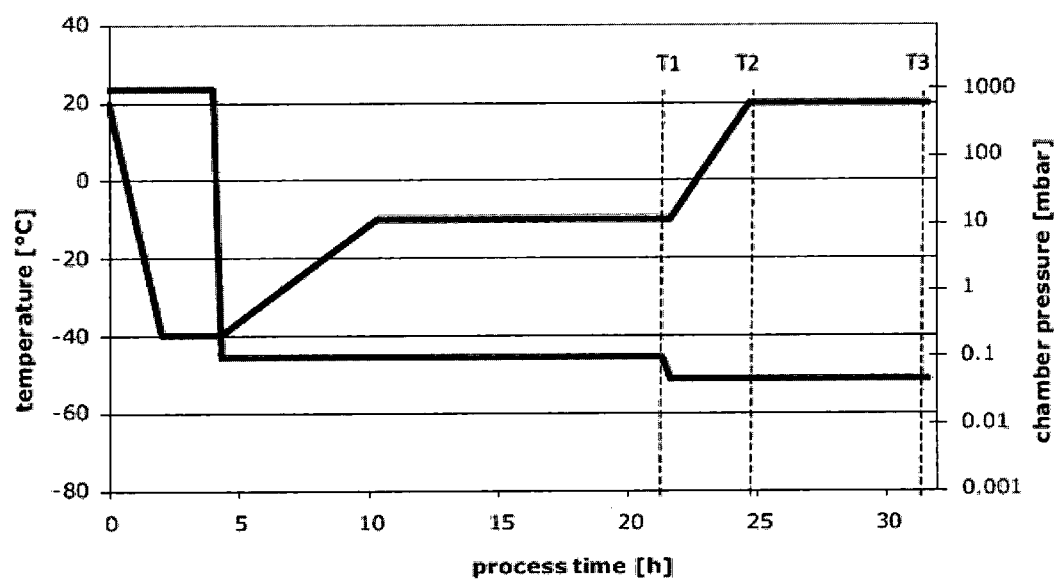

FIG. 7: Optimization of a lyophilization cycle under controlled freezing and controlled drying conditions (Example 5)

A. Temperature profile and pressure profile of the lyophilization cycle.

B. Residual moisture content of compositions lyophilized under controlled freezing and controlled drying conditions, wherein the residual moisture content was determined after storage of the lyophilized compositions at 40° C./75% rH for 24 weeks.

C. Relative integrity of mRNA lyophilized under controlled freezing and controlled drying conditions, wherein the lyophilized samples were stored at 40° C./75% rH for 24 weeks.

FIG. 8: Optimization of a lyophilization cycle under controlled freezing and controlled drying conditions; biological activity of lyophilized mRNA (Example 6)

A. Residual moisture content of compositions lyophilized under controlled freezing and controlled drying conditions after storage of the compositions at −80° C., at +5° C., at +25° C./60% r.H. or at +40° C./75% r.H., wherein the residual moisture content was determined after 1, 2, 3, 6, 9 or 12 months of storage.

B. Relative integrity of mRNA lyophilized under controlled freezing and controlled drying conditions, wherein the lyophilized samples were stored at −80° C., at +5° C., at +25° C./60% r.H. or at +40° C./75% r.H. for 1, 2, 3, 6, 9 or 12 months.

C. HI titers measured after injection of mRNA that was lyophilized under controlled freezing and controlled drying conditions and stored at −80° C. or at +25° C./60% r.H. for 6 months before reconstitution and injection.

D. Virus-neutralizing titers determined after injection of mRNA that was lyophilized under controlled freezing and controlled drying conditions and stored at −80° C. or at +25° C./60% r.H. for 6 months before reconstitution and injection.

EXAMPLES

The Examples shown in the following are merely illustrative and shall describe the present invention in a further way. These Examples shall not be construed to limit the present invention thereto.

Example 1: Preparation of DNA and RNA Constructs

Vectors for in vitro transcription were constructed, which contain a T7 promoter followed by a GC-enriched coding sequence.

A vector (PpLuc(GC)-muag-A64-C30) was constructed, which contains a T7 promoter followed by a GC-enriched sequence encoding the luciferase reporter gene, a sequence derived from the albumin-3'-UTR (muag), a stretch of 64 adenosines (poly(A)-sequence) and a stretch of 30 cytosines (poly(C)-sequence). The sequence of the corresponding mRNA is shown in SEQ ID NO: 1.

Another vector (HA(GC)-muag-A64-C30-histone stem-loop) was prepared, which contains a T7 promoter followed by a GC-enriched sequence encoding the hemagglutinin (HA) protein of influenza A virus (A/Netherlands/602/09), a sequence derived from the albumin-3'-UTR (muag), a stretch of 64 adenosines (poly(A)-sequence), a stretch of 30 cytosines (poly(C)-sequence) and a histone stem-loop. The sequence of the corresponding mRNA is shown in SEQ ID NO: 2.

A further vector (HsFOLH1(GC)-muag-A64-C30-histone stem-loop) was constructed which contains a T7 promoter followed by a GC-enriched sequence encoding the FOLH1 protein from *Homo sapiens*, a sequence derived from the albumin-3'-UTR (muag), a stretch of 64 adenosines (poly (A)-sequence), a stretch of 30 cytosines (poly(C)-sequence) and a histone stem-loop. The sequence of the corresponding mRNA is shown in SEQ ID NO: 3.

A further vector (RAV-G(GC)-muag-A64-C30-histone stem-loop) was constructed which contains a T7 promoter followed by a GC-enriched sequence encoding the RAV-G protein from Rabies virus, a sequence derived from the albumin-3'-UTR (muag), a stretch of 64 adenosines (poly (A)-sequence), a stretch of 30 cytosines (poly(C)-sequence) and a histone stem-loop. The sequence of the corresponding Rav-G mRNA sequence is provided in SEQ ID NO: 9.

The obtained vectors were linearized and subsequently in vitro transcribed by using T7 RNA polymerase. The DNA template was then degraded by DNAseI digestion. The mRNA was recovered by LiCl precipitation and further cleaned by HPLC extraction (PUREMessenger®, CureVac GmbH, Tubingen, Germany).

Example 2: Complexation of RNA mRNA obtained by in vitro transcription as described in Example 1 was complexed with protamine and trehalose. mRNA was diluted (0.87 g/L mRNA final concentration) and a protamine/trehalose mixture was prepared (0.43 g/L protamine; 10.87% trehalose in water for injection). Both solutions were mixed in an mRNA:protamine ratio of 2:1 (w/w).

The solution of RNA/protamine complexes was subsequently supplemented with free mRNA to yield final concentrations of 0.4 g/L mRNA complexed with 0.2 g/L protamine, 0.4 g/L free mRNA and 5% trehalose (w/w).

Alternatively, the concentration of trehalose in the protamine/trehalose mixture was adapted in order to obtain a final trehalose concentration (in the final solution) of 2.5% or 10% (w/w).

Such formulated RNA was used for lyophilization experiments.

Example 3: Standard Lyophilization Process mRNA encoding luciferase according to SEQ ID NO: 1 formulated according to Example 2 with a final mRNA concentration of 0.8 g/l and a final trehalose concentration of 5% (w/w). Aliquots of 75 µl were dispensed into sterile 2R glass vials (Type 1). The vials were half-closed with a freeze drying rubber stopper. The vials were frozen by using liquid nitrogen and loaded into a freeze dryer Alpha 2-4 (Martin Christ Gefriertrocknungsanlagen) and dried under the following conditions.

TABLE 1

| Step | Description | Temperature (shelves) | Pressure Pirani | Duration (hh:mm) |
|---|---|---|---|---|
| 1 | Loading | <−70° C. | atm | 00:00 |
| 4 | Evacuation | <−50° C. (shelves cooled with liquid nitrogen) | 63 µbar | ~00:20 |
| 5 | Primary drying | <−50° C. → 40° C. heating only controlled by final temperature | 63 µbar | 18:30 |
| 9 | Secondary drying | 40° C. shelves results in approximately 20° C. in the product | 45 µbar | 06:00 |
| 10 | Nitrogen back-fill | 40° C. | n.a. | — |
| 11 | Vial closure | 40° C. | n.a. | — |
| 12 | Aeration | 40° C. | atm | — |

The vials were sealed by crimping an aluminum cap over the stopper and the neck of the vial. Afterwards, the samples were stored at 25° C./60% relative humidity (r.H.) and 40° C./75% r.H. and analyzed for relative integrity after 5, 8, 13, 24 and 40 weeks (3 samples each). The relative integrity of the mRNA comprised in the lyophilized compositions was determined via agarose gel electrophoresis. Specifically, the relative integrity was determined by measuring the signal intensities corresponding to full-length mRNA and all other signals, respectively, in a lane of the agarose gel (i.e. in a given sample) and calculating the ratio of the signal intensity for full-length mRNA related to all other signals in that lane.

Results

TABLE 2

| Storage time (weeks) | +25° C./60% r.H. Rel. integrity (%) | +40° C./75% r.H. Rel. integrity (%) |
|---|---|---|
| 0 | 75 | 75 |
| 5 | 84 | 71 |
| 8 | 79 | 52 |
| 13 | 79 | 40 |
| 24 | 76 | 1 |
| 40 | 80 | 1 |

Figure 5:
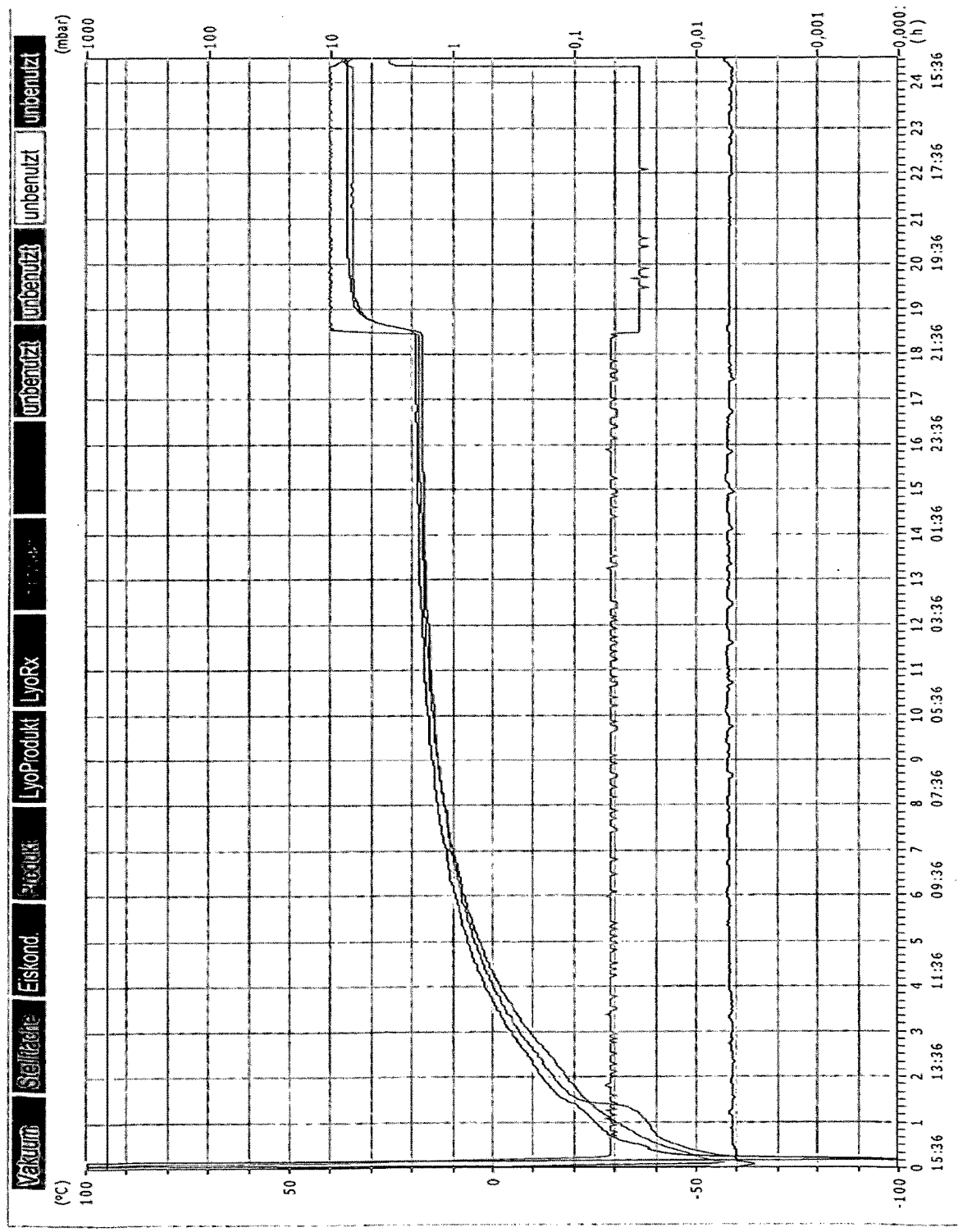
FIG. 5: A. Temperature profile and pressure profile of a standard lyophilization cycle. B. Relative integrity of mRNA lyophilized under standard conditions stored at 25° C./60% r.H. or at 40° C./75% r.H., respectively, for 40 weeks (Example 3).
Figure 5:
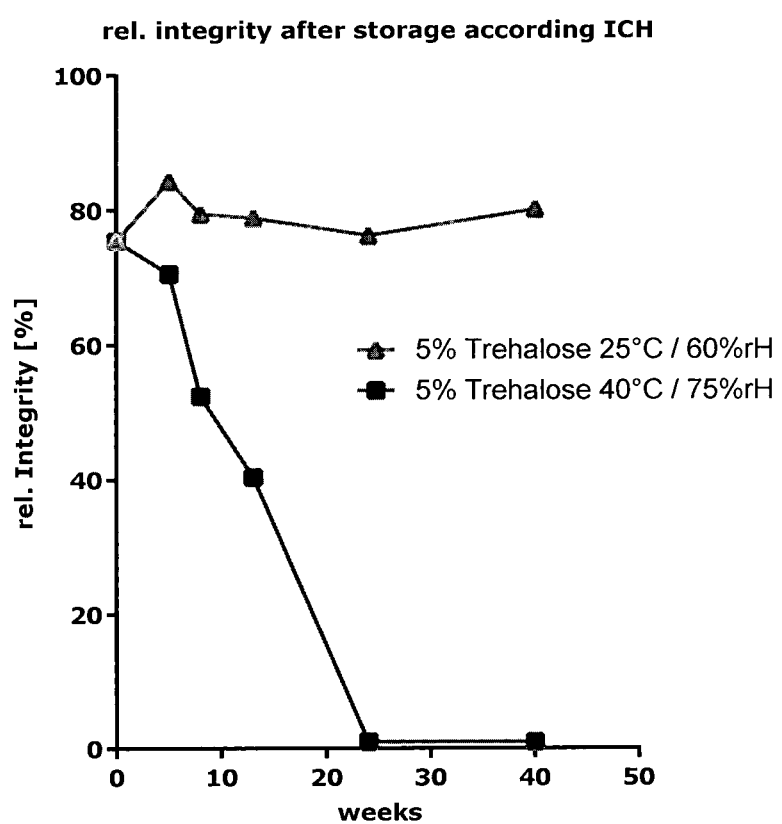

The storage of the mRNA/trehalose formulations dried under standard lyophilization conditions resulted in decreased integrity (relative integrity <80%) at 40° C./75% rH over time (see FIG. 5B), indicating that the compositions were not storage-stable.

Example 4: Optimization of a Lyophilization Cycle Under Controlled Freezing Conditions mRNA encoding hemagglutinin (HA) of A/Netherlands/602/09 (SEQ ID NO: 2) was formulated with protamine according to Example 2 in order to obtain a final mRNA concentration of 0.8 g/l and different trehalose concentrations of 2.5%, 5% and 10% (w/w), respectively. The glass transition temperature Tg' was determined by DSC (differential scanning calorimetry) and formulations were grouped into two classes on the basis of their Tg'. Group I comprises formulations having a Tg' between −30 and −32.5° C. (i.e. the mRNA formulation containing 5% and 10% trehalose); group II comprises formulations having a Tg' between −32.5 and −35° C. (i.e. the mRNA formulation containing 2.5% trehalose).

500 µl of each formulation were transferred into sterile glass vials (Type 1). The vials were half-closed with a freeze drying rubber stopper and were loaded onto the shelves of a freeze drier (Alpha 2-4; Christ Gefriertrocknungsanlagen) at 15° C. The controlled freezing to −40° C. was performed under controlled conditions for 02:55 h at a linear cooling rate of 0.31° C./min.

Lyophilization Cycle

TABLE 3

Group I

| Step | Description | Temperature (shelf temp, if not indicated otherwise) | Coolingrate/ Heating rate | Pressure Pirani | Duration (hh:mm) |
|---|---|---|---|---|---|
| 1 | Loading | 15° C. | | atm | 00:00 |
| 1a | Pre-cooling | 15° C. | | atm | 02:05 |
| 2 | Cooling down/Freezing | 15° C. → −40° C. (shelf) | 0.31° C./min | atm | 02:55 |
| 3 | Freezing | −40° C. | | atm | 07:20 |
| 4 | Evacuation | −40° C. | | 100 µbar | 00:20 |
| 5 | Primary drying (1) | −40° C. → −15° C. (shelf) | 4.2° C./h | 100 µbar | 06:00 |
| 6 | Primary drying (2) | −15° C. | | 100 µbar | 11:00 |
| 7 | Secondary drying (1) | −15° C. | | 45 µbar | 00:20 |
| 8 | Secondary drying (2) | −15° C. → 20° C. (product) 40° C. (shelf) | Not controlled | 45 µbar | 03:00 |
| 9 | Secondary drying (3) | 20° C. (product) 40° C. (shelf) | | 45 µbar | 07:00 |
| 10 | Nitrogen back-fill | 20° C. (product) 40° C. (shelf) | | n.a | — |
| 11 | Vial closure | 20° C. (product) 40° C. (shelf) | | n.a. | — |
| 12 | Aeration | 20° C. (product) 40° C. (shelf) | | atm | — |

TABLE 4

Group II

| Step | Description | Temperature (shelf temp, if not indicated otherwise) | Coolingrate/ Heating rate | Pressure Pirani | Duration (hh:mm) |
|---|---|---|---|---|---|
| 1 | Loading | 15° C. | | atm | 00:00 |
| 1a | Pre-cooling | 15° C. | | atm | 02:05 |
| 2 | Freezing | 15° C. → −40° C. (shelf) | 0.31° C./min | atm | 02:55 |
| 3 | Freezing | −40° C. | | atm | 07:20 |
| 4 | Evacuation | −40° C. | | 100 µbar | 00:20 |
| 5 | Primary drying | −40° C. → −17° C. (shelf) | 2.6° C./h | 100 µbar | 09:00 |

TABLE 4-continued

| | | Group II | | | |
|---|---|---|---|---|---|
| Step | Description | Temperature (shelf temp, if not indicated otherwise) | Coolingrate/ Heating rate | Pressure Pirani | Duration (hh:mm) |
| 6 | Primary drying | −17° C. | | 100 µbar | 16:00 |
| 7 | Secondary drying | −17° C. | | 45 µbar | 00:20 |
| 8 | Secondary drying | −17° C. → 20° C. (product) 40° C. (shelf) | Not controlled | 45 µbar | 03:00 |
| 9 | Secondary drying | 20° C. (product) 40° C. (shelf) | | 45 µbar | 07:00 |
| 10 | Nitrogen back-fill | 20° C. (product) 40° C. (shelf) | | n.a. | — |
| 11 | Vial closure | 20° C. (product) 40° C. (shelf) | | n.a. | — |
| 12 | Aeration | 20° C. (product) 40° C. (shelf) | | atm | — |

Due to the functionality of the freeze dryer only shelf temperatures between about −40° C. and 0° C. can be controlled. Higher temperatures can be reached, but are not associated with a constant heating rate. Therefore, only a heating rate for the primary drying can be specified.

After secondary drying (Step 9), the freeze drying chamber was flooded with nitrogen (step 10) and the vials were manually closed by lowering the shelves above (step 11). The chamber was finally vented to atmospheric pressure (atm, step 12) and the vials were removed from the freeze dryer.

The vials were sealed by crimping an aluminum cap over the stopper and the neck of the vial. The residual moisture content was determined by Karl-Fischer titration. Afterwards, the samples were stored at +50° C. (without controlling the relative humidity) and analyzed with respect to residual moisture content of the formulation and the relative integrity of the RNA (see Example 3) after 2 weeks (relative integrity only), 1, 2 and 3 months.

Results

TABLE 5

| | 2.5% Trehalose | | 5% Trehalose | | 10% Trehalose | |
|---|---|---|---|---|---|---|
| Storage Time (months) | Residual moisture (%) | Rel. integrity (%) | Residual moisture (%) | Rel. integrity (%) | Residual moisture (%) | Rel. integrity (%) |
| 0 | 2.7 | 96 | 1.3 | 98 | 1.5 | 98 |
| 0.5 | | 94 | | 95 | | 95 |
| 1 | 3.9 | 95 | 2.4 | 93 | 1.8 | 96 |
| 2 | | 89 | | 90 | | 93 |
| 3 | 2.7 | 80 | 2.0 | 83 | 1.9 | 89 |

All samples have a residual moisture content of <4%. Nevertheless, higher concentrations of lyoprotectant result in a reduced residual moisture content (see FIG. 6A). All samples show an integrity >80% after storage at +50° C. for 3 months (see FIG. 6B). Lyophilization of RNA under controlled freezing conditions thus results in increased integrity of the lyophilized RNA product over time and outstanding storage stability.

Example 5: Optimization of a Lyophilization Cycle Under Controlled Freezing and Controlled Drying Conditions The integrity of lyophilized compositions, in particular the integrity of the mRNA comprised in those compositions, after storage under conditions with controlled relative humidity (40° C./75% r.H.) was analyzed. To this end, an mRNA encoding HsFOHL1 (SEQ ID NO: 3) was formulated with protamine according to Example 2 with a final mRNA concentration of 0.8 g/l in the presence of 5% (w/w) trehalose and filled into sterile glass (Type1) vials (600 µl per vial). The vials were half-closed with a freeze drying rubber stopper and loaded onto the shelves of the freeze drier at 20° C. Lyophilization was performed using the freeze-drier Epsilon 2-12D (Martin Christ, Osterrode, Germany). The vacuum during the freeze-drying process was controlled by a MKS Capacitance Manometer. The process parameters of the cycle are detailed in the table below.

TABLE 6

| Step | Description | Shelf temperature | Cooling/ heating rate | Pressure MKS (mbar) | Duration (hh:mm) |
|---|---|---|---|---|---|
| 1 | Load | 20° C. | | 1000 | 00:00 |
| 2 | Freezing | 20° C. → −40° C. | 0.5° C./min | 1000 | 02:00 |
| 3 | Freezing | −40° C. | | 1000 | 02:00 |
| 4 | Evacuation | −40° C. | | 0.1 | 00:33 |

TABLE 6-continued

| Step | Description | Shelf temperature | Cooling/ heating rate | Pressure MKS (mbar) | Duration (hh:mm) |
|---|---|---|---|---|---|
| 5 | Primary drying | −40° C. → −10° C. | 5° C./h | 0.1 | 06:00 |
| 6 | Primary drying | −10° C. | | 0.1 | 11:00 |
| 7 | Secondary drying | −10° C. | | 0.045 | 00:33 |
| 8 | Secondary drying | −10° C. → 20° C. | 10° C./h | 0.045 | 03:00 |
| 9 | Secondary drying | 20° C. | | 0.045 | 07:00 |
| 10 | Nitrogen back-fill | 20° C. | | n.a | — |
| 11 | Vial closure | 20° C. | | n.a. | — |
| 12 | Aeration | 20° C. | | atm | — |

The residual moisture content of the obtained samples was determined by Karl-Fischer titration. The samples were stored at 40° C./75% r.H. and analyzed after 2, 4, 6, 12 and 24 weeks. The relative integrity (see Example 3) of the lyophilized mRNA was used as a measure of storage stability of the lyophilized composition under the specific storage conditions in this experiment, i.e. at 40° C./75% r.H.

Results

The residual moisture content of the lyophilized mRNA/trehalose formulations increased over time if stored at +40° C./75% r.H., but remained well below 2.5% (see FIG. 7B). Nevertheless, a relative integrity of the lyophilized RNA of above 80% could be obtained for the samples stored for up to 12 weeks (see FIG. 7C). After storage for 24 weeks, the relative integrity of the RNA was still 79.1%. These results demonstrate that lyophilization under controlled freezing and controlled drying conditions results in increased relative integrity of the lyophilized RNA product and further results in improved storage stability of the lyophilized RNA as compared to the relative integrity of an RNA lyophilized under non-controlled conditions and its storage stability, respectively (Example 3).

Example 6: Optimization of a Lyophilization Cycle Under Controlled Freezing and Controlled Drying Conditions; Biological Activity of Lyophilized mRNA mRNA encoding hemagglutinin (HA) of A/Netherlands/602/09 (SEQ ID NO: 2) was formulated with protamine in a weight ratio of 4:1 according to Example 2 with a final mRNA concentration of 0.8 g/l in the presence of 5% (w/w) trehalose. The formulation was cooled to −80° C. Prior to filling of 600 µl formulation per sterile 2R glass (type 1) vials, the formulation was allowed to thaw at room temperature (20-25° C.). The vials were half-closed with freeze drying rubber stoppers and loaded onto the shelves of the freeze drier at 20° C. Lyophilization was performed on a BOC Edwards Lyoflex 04 freeze-drier and included a freeze drying cycle with the following conditions:

TABLE 7

| Step | Description | Shelf Temperature | Cooling/ heating rate | Pressure Pirani | Duration (hh:mm) |
|---|---|---|---|---|---|
| 1 | Load | 20 C. | | atm | 00:00 |
| 2 | Freezing | 20° C. → −40° C. | 0.5° C./min | atm | 02:00 |
| 3 | Freezing | −40° C. | | atm | 02:00 |
| 4 | Evacuation | −40° C. | | 160 µbar | 00:20 |
| 5 | Primary drying | −40° C. → −10° C. | 5° C./h | 160 µbar | 06:00 |
| 6 | Primary drying | −10° C. | | 160 µbar | 11:00 |
| 7 | Secondary drying | −10° C. | | 68 µbar | 00:20 |
| 8 | Secondary drying | −10° C. → 20° C. | 10° C./h | 68 µbar | 03:00 |
| 9 | Secondary drying | 20° C. | | 68 µbar | 07:00 |
| 10 | Nitrogen back-fill | 20° C. | | 0.8 bar | — |
| 11 | Vial closure | 20° C. | | 0.8 bar | — |
| 12 | Aeration | 20° C. | | atm | — |

The vacuum was controlled by a Pirani manometer. After the secondary drying (Step 9), the freeze drying chamber was flooded with nitrogen up to a pressure of 0.8 bar (Step 10) and the vials were automatically closed by lowering the shelves above (Step 11). The chamber was finally vented to atmospheric pressure (Step 12) and the vials were removed from the freeze dryer. The vials were sealed by crimping an aluminum cap over the rubber stopper and the neck of the vial. After determination of the residual moisture content of each sample, the samples were stored at −80° C., +5° C., +25° C./60% r.H. or +40° C./75% r.H. for 1, 2, 3, 6, 9 and 12 months, respectively. After that storage period, the samples were analyzed with respect to their residual moisture content and with respect to the relative integrity of the lyophilized mRNA.

Results

TABLE 8

| Storage | −80° C. | | +5° C. | | +25° C./ 60% r.H. | | +40° C./ 75% r.H. | |
|---|---|---|---|---|---|---|---|---|
| Time (months) | r.M. (%) | r.I. (%) | r.M. (%) | r.I. (%) | r.M. (%) | r.I. (%) | r.M. (%) | r.I. (%) |
| 0 | 0.875 | 99 | 0.875 | 99 | 0.875 | 99 | 0.875 | 99 |
| 1 | 0.93 | 97 | 1.015 | 97 | 1.185 | 96 | 1.55 | 95 |
| 2 | 0.975 | 97 | 0.995 | 99 | 1.275 | 97 | 2.005 | 95 |
| 3 | 1.015 | 98 | 1.08 | 99 | 1.62 | 97 | 2.43 | 92 |
| 6 | 1.25 | 97 | 1.555 | 95 | 1.92 | 96 | 4.36 | 86.2 |
| 9 | 0.415 | 98 | 0.605 | 97 | 1.605 | 96 | 5.595 | 83 |
| 12 | 0.18 | 99 | 0.525 | n.d. | 1.53 | 97 | 6.41 | 80 |

(r.M.: residual moisture content; r.I.: residual integrity)

The residual moisture content of the lyophilized mRNA/trehalose formulations increased over time if stored at +40° C./75% r.H. (see FIG. 8A). The increase of residual moisture above 4% after 6 months in mRNA/trehalose formulations correlated with a decreased relative integrity of the lyophilized RNA of below 90% (see FIG. 8B).

Nevertheless, a relative integrity of the lyophilized RNA of above 80% was obtained for all samples, even in the samples stored at +40° C./75% r.H. over 12 months. Lyophilization under controlled freezing and controlled drying conditions results in improved stability of the lyophilized RNA compared to lyophilization under non-controlled conditions (Example 3).

Biological Activity

The biological activity of the mRNA was measured after storage of the lyophilized samples for 6 months at −80° C. and +25° C./60% r.H. To this end, the lyophilized mRNA was reconstituted subsequent to the storage period and used for vaccination of mice. The presence of functional antibodies was subsequently determined by using a hemagglutinin inhibition assay and a virus neutralization assay.

Vaccination

Lyophilized mRNA was reconstituted in Ringer-Lactate solution. Female BALB/c mice were immunized in a prime/boost scenario using 80 pg mRNA coding for hemagglutinin (HA) of A/Netherlands/602/09 (SEQ ID NO: 2) complexed with protamine prepared according to Example 2, lyophilized as described above and stored at +25° C. or at −80° C. Blood was collected 34 days after last vaccination and analyzed for the presence of functional antibodies by hemagglutinin inhibition assay and virus neutralization assay.

Hemagglutination Inhibition (HI) Assay

For the hemagglutination inhibition (HI) assays, mouse sera was heat inactivated (56° C., 30 min), incubated with kaolin and pre-adsorbed to chicken red blood cells (CRBC) (both Labor Dr. Merck & Kollegen, Ochsenhausen, Germany). For the HI assay, 50 µl each of two-fold dilutions of pre-treated sera were incubated for 45 min with 4 HAU (units of HA) of inactivated A/California/07/2009 virus and 50 µl 0.5% CRBC were added. The highest dilution of serum that prevents hemagglutination is referred to as the HI titer of the serum.

Virus-Neutralizing Titers

Virus-neutralizing titers were determined in sera pre-treated by heat inactivation (56° C., 30 min). Serially diluted sera were incubated for 2 hours with 100×TCID50 (tissue culture 50% infectious dose) of virus and subsequently transferred to monolayers of MDCK cells. Presence or absence of virus was determined after 3 days by performing a hemagglutination assay of supernatants using inactivated A/California/04/09 virus.

Results

No difference in biological activity of the lyophilized mRNA could be seen after storage of the formulations at −80° C. and +25° C./60% r.H. It can be concluded that storage at higher temperatures does not affect the biological activity of mRNA lyophilized by an optimized lyophilization cycle. (see FIG. 8C)

Example 7: Optimization of a Lyophilization Cycle Under Controlled Freezing and Controlled Drying Conditions; Long-Term Stability and Safety of Lyophilized mRNA mRNA encoding RAV-G (SEQ ID NO: 9) was formulated with protamine in a weight ratio of 4:1 according to Example 2 with a final mRNA concentration of 0.8 g/l in the presence of 5% (w/w) trehalose. The formulation was cooled to −80° C. Prior to filling of 600 µl formulation per sterile 2R glass (type 1) vials, the formulation was allowed to thaw at room temperature (20-25° C.). The vials were half-closed with freeze drying rubber stoppers and loaded onto the shelves of the freeze drier at 20° C. Lyophilization was performed on a BOC Edwards Lyoflex 04 freeze-drier and included a freeze drying cycle with the conditions provided in Table 9.

TABLE 9

| Step | Description | Shelf temperature | Cooling/ heating rate | Pressure MKS (mbar) | Duration (hh:mm) |
|---|---|---|---|---|---|
| 1 | Load | 20° C. | | 1000 | 00:00 |
| 2 | Freezing | 20° C. → −40° C. | 0.5° C./min | 1000 | 02:00 |
| 3 | Freezing | −40° C. | | 1000 | 02:00 |
| 4 | Evacuation | −40° C. | | 0.1 | 00:33 |
| 5 | Primary drying | −40° C. → −10° C. | 5° C./h | 0.1 | 06:00 |
| 6 | Primary drying | −10° C. | | 0.1 | 11:00 |
| 7 | Secondary drying | −10° C. | | 0.045 | 00:20 |
| 8 | Secondary drying | −10° C. → 20° C. | 10° C./h | 0.045 | 03:00 |
| 9 | Secondary drying | 20° C. | | 0.045 | 07:00 |

TABLE 9-continued

| Step | Description | Shelf temperature | Cooling/ heating rate | Pressure MKS (mbar) | Duration (hh:mm) |
|---|---|---|---|---|---|
| 10 | Nitrogen back-fill | 20° C. | | n.a | — |
| 11 | Vial closure | 20° C. | | n.a. | — |
| 12 | Aeration | 20° C. | | atm | — |

Long-Term Stability and Safety of Lyophilized mRNA

In order to assess long term stability and safety of the lyophilized RAV-G mRNA under different temperature conditions, certain quality attributes of stored RAV-G RNA were analyzed including appearance, RNA integrity, RNA content, pH value, and osmolarity. These quality attributes are discussed in further detail below.

Appearance:

The visual appearance of the lyophilisate cake is an indicator for the stability of the RNA. RNA lyophilisates should be white to yellowish in colour to meet that stability specification.

RNA Integrity:

Degradation of RNA over time leads to a loss of RNA integrity. The integrity of the RNA was analyzed after re-constitution of the RNA in water via RNA gelelectrophoresis. RNA gelelectrophoresis was performed according to methods commonly known in the art. Band sharpness was analyzed to determine the integrity of the RNA. Moreover, the gel was analyzed for the presence of additional undesired bands or artefacts.

RNA Content:

Increasing RNA content over time is an indicator for an evaporation of solvent. Therefore, the RNA content of the stored RNA lyophilisate was analyzed. A dried RNA sample was re-suspended in 10 ml WFI. The RNA concentration of the sample was determined photometrically.

pH Value:

A change in pH over time may be an indicator for undesired chemical reactions of the product components. Potentiometric determination of the pH content was performed using a commercially available volt-meter according to the European pharmacopedia (PhEur) 2.2.3.

Osmolarity:

Changes in osmolarity over time may be an indicator for undesired chemical reactions of the product components. The measurement of the osmolality was performed according to European pharmacopedia (PhEur) 2.2.35, using a commercially available osmometer.

One stability study was conducted that analyzed long term stability (up to 36 months) under controlled conditions at 5° C. (results are shown in Table 10). Moreover, one stability study at higher temperatures (25° C.) over 36 months has been performed (see Table 11).

Results:

TABLE 10

Results of the stability analysis; up to 36 months; 5° C.

| Attribute | Analysis of time points [months] | | | | | | | |
|---|---|---|---|---|---|---|---|---|
| | 0 | 3 | 6 | 9 | 12 | 18 | 24 | 36 |
| Appearance | conform | conform | conform | conform | conform | conform | conform | conform |
| Integrity [%] | 100 | 100 | 97 | 88 | 95 | 82 | 87 | 87 |
| Content [g/l] | 0.69 | 0.72 | 0.71 | 0.70 | 0.72 | 0.75 | 0.65 | 0.74 |
| pH value | 6.6 | 6.6 | 6.5 | 6.3 | 6.6 | 6.5 | 6.2 | 6.3 |
| Osmolarity [mOsmol/kg] | 150 | 145 | 148 | 142 | 154 | 141 | 144 | 144 |

TABLE 11

Results of the stability analysis; up to 36 months; 25° C.

| Attribute | Analysis of time points [months] | | | | | | | |
|---|---|---|---|---|---|---|---|---|
| | 0 | 3 | 6 | 9 | 12 | 18 | 24 | 36 |
| Appearance | conform | conform | conform | conform | conform | conform | conform | conform |
| Integrity [%] | 100 | 95 | 93 | 83 | 84 | 77 | 80 | 75 |
| Content [g/l] | 0.69 | 0.70 | 0.67 | 0.70 | 0.67 | 0.75 | 0.69 | 0.72 |
| pH value | 6.6 | 6.6 | 6.5 | 6.3 | 6.6 | 6.5 | 6.0 | 6.4 |
| Osmolarity [mOsmol/kg] | 150 | 150 | 150 | 144 | 150 | 145 | 143 | 144 |

The results show that the inventive lyophilisation method according to the present invention is particularly suitable to produce stable RNA lyophilisates for long-term storage. The results shown in Table 10 and 11 show that all quality attributes analysed during the experimental period (up to 36 months) meet the stability specifications of a stable and safe RNA medicament. Notably, even at higher temperatures (25° C., see Table 11) these stability specifications were met, showing that the inventive lyophilisation method is particularly suitable to produce long term stable and temperature resistant RNA lyophilisates.

The invention claimed is:

1. A method for lyophilizing long-chain RNA, wherein the method comprises the following steps:
a) providing a liquid having a glass transition temperature comprising at least one long-chain RNA and at least one lyoprotectant, wherein the glass transition temperature of the liquid is in a range from −15° C. to −50° C.;
b) introducing the liquid provided into a freeze drying chamber of a freeze dryer;
c) cooling the liquid to a freezing temperature, wherein the cooling is performed at a defined cooling rate;
d) freezing the liquid having the glass transition temperature at the freezing temperature in order to obtain a frozen liquid, wherein the freezing temperature is in a range from 0.5° C. to 25° C. below the glass transition temperature of the liquid provided in step a);
e) reducing the pressure in the freeze drying chamber to a pressure below atmospheric pressure;
f) drying the frozen liquid obtained in step d) in order to obtain a lyophilized composition comprising the at least one long-chain RNA and at least one lyoprotectant, wherein drying comprises heating the frozen liquid obtained in step d) to a drying temperature, wherein the heating is performed at a defined heating rate, wherein the defined heating rate is in a range from 0.1° C./h to 20° C./h; and
g) equilibrating the pressure in the freeze drying chamber to atmospheric pressure and removing the lyophilized composition comprising the at least one long-chain RNA and the at least one lyoprotectant obtained in step f) from the freeze drying chamber.

2. The method of claim 1, wherein the at least one long-chain RNA comprises from 100 to 50,000 nucleotides.

3. The method of claim 1, wherein the at least one long-chain RNA is not a viral RNA or an RNA that is derived from a viral RNA.

4. The method of claim 1, wherein the drying temperature is lower than the glass transition temperature of the liquid.

5. The method of claim 1, wherein the drying temperature is in a range from −40° C. to 40° C.

6. The method of claim 1, wherein the liquid further comprises at least one cationic or polycationic compound.

7. The method of claim 6, wherein the cationic or polycationic compound is a cationic or polycationic peptide or protein.

8. The method of claim 6, wherein the at least one long-chain RNA and the at least one cationic or polycationic compound are present in a complex.

9. The method of claim 1, wherein the at least one long-chain RNA comprises at least one coding region.

10. The method of claim 1, wherein the at least one long-chain RNA is an mRNA.

11. The method of claim 1, wherein the lyoprotectant is a carbohydrate compound, preferably selected from the group consisting of mannitol, sucrose, glucose, mannose, trehalose.

12. The method of claim 1, wherein the concentration of the lyoprotectant in the liquid provided in step a) is in a range from 1 to 20% (w/w).

13. The method of claim 1, wherein the concentration of the at least one long-chain RNA in the liquid provided in step a) is in a range from 0.1 to 10 g/l.

14. The method according to claim 1, wherein the glass transition temperature of the liquid is in a range from −25° C. to −40° C.

15. The method according to claim 1, wherein the freezing temperature is in a range from −50° C. to −35° C.

16. The method of claim 1, wherein the cooling rate in step c) is in a range from 0.1° C./min to 2° C./min.

17. A method for lyophilizing single-stranded RNA, wherein the method comprises the following steps:
  a) providing a liquid having a glass transition temperature comprising at least one single-stranded RNA and at least one lyoprotectant, wherein the glass transition temperature of the liquid is in a range from −15° C. to −50° C.;
  b) introducing the liquid provided into a freeze drying chamber of a freeze dryer;
  c) cooling the liquid to a freezing temperature, wherein the cooling is performed at a defined cooling rate;
  d) freezing the liquid having the glass transition temperature at the freezing temperature in order to obtain a frozen liquid having the glass transition temperature, wherein the freezing temperature is in a range from 0.5° C. to 25° C. below the glass transition temperature of the liquid provided in step a);
  e) reducing the pressure in the freeze drying chamber to a pressure below atmospheric pressure;
  f) drying the frozen liquid obtained in step d) in order to obtain a lyophilized composition comprising the at least one single-stranded RNA and at least one lyoprotectant, wherein drying comprises heating the frozen liquid obtained in step d) to a drying temperature, wherein the heating is performed at a defined heating rate, wherein the defined heating rate is in a range from 0.1° C./h to 20° C./h; and
  g) equilibrating the pressure in the freeze drying chamber to atmospheric pressure and removing the lyophilized composition comprising the at least one single-stranded RNA and the at least one lyoprotectant obtained in step f) from the freeze drying chamber.

\* \* \* \* \*